(12) United States Patent
Tang et al.

(10) Patent No.: US 8,999,990 B2
(45) Date of Patent: Apr. 7, 2015

(54) INHIBITORS OF THE RENAL OUTER MEDULLARY POTASSIUM CHANNEL

(71) Applicants: Haifeng Tang, Metuchen, NJ (US); Barbara Pio, West Orange, NJ (US); Nardos Teumelsan, Rahway, NJ (US); Alexander Pasternak, Princeton, NJ (US); Reynalda DeJesus, East Brunswick, NJ (US)

(72) Inventors: Haifeng Tang, Metuchen, NJ (US); Barbara Pio, West Orange, NJ (US); Nardos Teumelsan, Rahway, NJ (US); Alexander Pasternak, Princeton, NJ (US); Reynalda DeJesus, East Brunswick, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 14/353,410

(22) PCT Filed: Oct. 22, 2012

(86) PCT No.: PCT/US2012/061274
§ 371 (c)(1),
(2) Date: Apr. 22, 2014

(87) PCT Pub. No.: WO2013/062892
PCT Pub. Date: May 2, 2013

(65) Prior Publication Data
US 2014/0296225 A1    Oct. 2, 2014

Related U.S. Application Data

(60) Provisional application No. 61/550,950, filed on Oct. 25, 2011.

(51) Int. Cl.

| | | |
|---|---|---|
| A61K 31/495 | (2006.01) |
| A61K 31/496 | (2006.01) |
| C07D 295/22 | (2006.01) |
| C07D 401/06 | (2006.01) |
| C07D 403/10 | (2006.01) |
| C07D 407/10 | (2006.01) |
| C07D 413/10 | (2006.01) |
| C07D 405/14 | (2006.01) |
| C07D 413/14 | (2006.01) |
| C07D 403/06 | (2006.01) |
| C07D 405/06 | (2006.01) |
| C07D 413/06 | (2006.01) |
| C07D 241/08 | (2006.01) |
| A61K 45/06 | (2006.01) |
| C07D 241/04 | (2006.01) |

(52) U.S. Cl.
CPC ........... *C07D 413/10* (2013.01); *C07D 405/14* (2013.01); *C07D 413/14* (2013.01); *C07D 403/06* (2013.01); *C07D 405/06* (2013.01); *C07D 413/06* (2013.01); *C07D 241/08* (2013.01); *A61K 31/495* (2013.01); *A61K 31/496* (2013.01); *A61K 45/06* (2013.01); *C07D 241/04* (2013.01); *C07D 401/06* (2013.01); *C07D 403/10* (2013.01); *C07D 407/10* (2013.01)

(58) Field of Classification Search
None
See application file for complete search history.

(56) References Cited

U.S. PATENT DOCUMENTS

| | | |
|---|---|---|
| 2,988,551 A | 6/1961 | Morren |
| 3,435,002 A | 3/1969 | Holub |
| 3,632,608 A | 1/1972 | Holub |
| 3,749,722 A | 7/1973 | Holub |
| 4,579,863 A | 4/1986 | Horwell et al. |
| 4,806,536 A | 2/1989 | Cross et al. |
| 4,992,547 A | 2/1991 | Berner et al. |
| 5,145,885 A | 9/1992 | Berner et al. |
| 5,215,989 A | 6/1993 | Baldwin et al. |
| 5,614,526 A | 3/1997 | Godel et al. |
| 5,736,546 A | 4/1998 | Kawashima et al. |
| 6,258,813 B1 | 7/2001 | Arlt et al. |
| 6,787,543 B2 | 9/2004 | Take et al. |
| 2004/0204404 A1 | 10/2004 | Zelle et al. |
| 2005/0215526 A1 | 9/2005 | Hulme et al. |
| 2005/0267121 A1 | 12/2005 | Li et al. |
| 2006/0183739 A1 | 8/2006 | Tsaklakidis et al. |

(Continued)

FOREIGN PATENT DOCUMENTS

| | | |
|---|---|---|
| EP | 0099148 B1 | 2/1988 |
| EP | 0175376 B1 | 4/1991 |

(Continued)

OTHER PUBLICATIONS

Felix et al. Assay and Drug Development Technologies, 10(5), pp. 417-431 (2012).*

(Continued)

*Primary Examiner* — Emily Bernhardt
(74) *Attorney, Agent, or Firm* — Nicole M. Beeler; Catherine D. Fitch

(57) ABSTRACT

The present invention provides compounds of Formula I

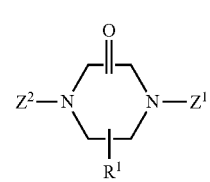

and the pharmaceutically acceptable salts thereof, which are inhibitors of the ROMK (Kir1.1) channel. The compounds act as diuretics and natriuretics and are valuable pharmaceutically active compounds for the therapy and prophylaxis of medical conditions including cardiovascular diseases such as hypertension and conditions resulting from excessive salt and water retention.

12 Claims, No Drawings

(56) References Cited

U.S. PATENT DOCUMENTS

| | | |
|---|---|---|
| 2006/0183742 A1 | 8/2006 | Mederski et al. |
| 2006/0211692 A1 | 9/2006 | Mederski et al. |
| 2007/0004750 A1 | 1/2007 | Lorsbach et al. |
| 2007/0093472 A1 | 4/2007 | Mederski et al. |
| 2007/0232546 A1 | 10/2007 | Sharma et al. |
| 2008/0003214 A1 | 1/2008 | Cezanne et al. |
| 2010/0286123 A1 | 11/2010 | Pasternak et al. |

FOREIGN PATENT DOCUMENTS

| | | |
|---|---|---|
| EP | 1094063 A1 | 4/2001 |
| EP | 1939175 A1 | 7/2009 |
| FR | 2673182 | 8/1992 |
| GB | 949088 A | 2/1964 |
| GB | 1575310 A | 9/1980 |
| GB | 2116967 | 7/1986 |
| JP | 10203986 | 8/1998 |
| WO | 9744329 | 11/1997 |
| WO | 0051611 A1 | 9/2000 |
| WO | 0204314 A1 | 6/2002 |
| WO | 0250061 A1 | 6/2002 |
| WO | 02032874 | 11/2003 |
| WO | 2004020422 A1 | 3/2004 |
| WO | 2004037817 A1 | 5/2004 |
| WO | 2004046110 | 6/2004 |
| WO | 2005037843 | 4/2005 |
| WO | 2005044797 | 5/2005 |
| WO | 2006034341 A2 | 3/2006 |
| WO | 2006034769 A1 | 4/2006 |
| WO | 2006098342 A1 | 9/2006 |
| WO | 2007075629 A2 | 7/2007 |
| WO | 2008147864 | 12/2008 |
| WO | 2008147864 A2 | 12/2008 |
| WO | 2009149508 | 11/2009 |
| WO | 2010129379 A1 | 11/2010 |
| WO | 2012058116 A1 | 5/2012 |
| WO | 2012058134 A1 | 5/2012 |
| WO | 2006129199 A1 | 12/2012 |
| WO | 2013028474 A1 | 2/2013 |
| WO | 2013039802 A1 | 3/2013 |
| WO | 2013062900 A1 | 5/2013 |
| WO | 2013066714 A1 | 5/2013 |
| WO | 2013066717 A1 | 5/2013 |
| WO | 2013066718 A2 | 5/2013 |
| WO | 2013090271 A1 | 6/2013 |
| WO | 2014015495 A1 | 1/2014 |
| WO | 2014018764 A1 | 1/2014 |

OTHER PUBLICATIONS

ACCF/AHA Practice Guideline, 2009 Focused update incorporated into the ACC/AHA 2005 guidelines . . . , Circulation, 2009, e391-e436, 119.

Baltzly, R., The preparation of N-mono-substituted and unsymmetrically disubstituted piperazines, J. Am. Chemoc., 1944, 263-266, 66.

Bhave, G., Small-molecule modulators of inward rectifier K+ channels: recent advances and future possibilities, Future Med Chem, 2010, 757-774, 2(5).

Bhave,G., Development of a selective small-molecule inhibitor Kir1.1, the renal outer medullary potassium channel, Mol. Pharmacol., 2011, 42-50, 79.

Brater et al., Diuretic Therapy, Drug Therapy, 1998, 387-395, 339.

Brewster et al., Antihypertensive 1,4-bis (2-indol-3-ylethyl)piperazines, Chimie Ther., 1973, 169-172 (English trans.), 2.

Cerkvenik-Flajs V, Determination of residues of azaperone in the kidneys by liquid chromatography with fluorescence, Anal. Chim. Acta., 2007, 374-382, 586.

Chemical Abstracts (2004), Abstract No. 697771-49-6, "1,3-Isobenzofurandione 5-[[4-[(5-chloro-2-methoxyphenyl) sulfonyl]-1-...".

Cheymol et al., Increase in the effects of epinephrine and acetylcholine . . . , Comptes Rendus des seances de la Societe de Biologie, 1951, 496-499 (English trans.), 145.

Fallen, K., The Kir channel immunoglobuling domain is essential for Kir1.1 (ROMK) thermodynamic stability, trafficing and gating, Channels, 2009, 57-66, 3.

Felker et al, Diuretic strategies in patients with acute decompensated heart failure, New Eng. J. Med., 2011, 797-805, 364.

Frank, Managing hypertension using combination therapy, Am. Fam. Physician, 2008, 1279-1286, 77.

International Search Report and Written Opinion for PCT/US2012/61274, 7 pages, mailed Feb. 6, 2013.

Kulkarni, Yd, Possible antifertility agents, part III. Synthesis of 4-(substituted aminomethyl)-5,6,7-trimethoxy phthalid . . . (abstract)), Biol. Mem., 1987, 141-144, 13.

Lanyi et al., Piperazine-Derivatives II, Res. Lab. of Chinoin-Fabrik Chemisch-Pharma. Prod., 1968, 1431-1435 (English trans.), 18.

Lee et al, Functional and structural characterization of Pka-mediated pHi gating of ROMK1 channels, Journal of Molecular Graphics and Modelling, 2008, 332-341, 27.

Lewis, L. M., High-throughput screening reveals a small-molecule inhibitor of the Renal Outer Medullary Potassium Channel and Kir7.1, Mol. Pharncol., 2009, 1094-1103, 76.

Lutz, R. E., Antimalarials. Some Piperazine Derivatives, J. Org. Chem., 1947, 771-775, 12, BO.

Miyake et al., Synthesis of 1-substituted isochroman . . . , Takeda Res. Lab., 1982, 24-40 (English trans.), 41.

Sica, D. A., Diuretic use in renal disease, Nature, 2012, 100-109, 8.

Zejc et al., Piperazine derivative of dimethylxanthines, Polish J. Pharmacol. & Pharm., 1975, 311-316 (English trans.), 27.

* cited by examiner

INHIBITORS OF THE RENAL OUTER MEDULLARY POTASSIUM CHANNEL

CROSS REFERENCE TO RELATED APPLICATIONS

This application is a U.S. National Phase application under 35 U.S.C. §371 of PCT Application No. PCT/US12/061,274 filed Oct. 22, 2012, which claims priority from U.S. Provisional Application Ser. No. 61/550,950, filed Oct. 25, 2011.

BACKGROUND OF THE INVENTION

The Renal Outer Medullary Potassium (ROMK) channel (Kir1.1) (see e.g., Ho, K., et al., *Cloning and expression of an inwardly rectifying ATP-regulated potassium channel*, Nature, 1993, 362(6415): p. 31-8.1, 2; and Shuck, M. E., et al., *Cloning and characterization of multiple forms of the human kidney ROM-K potassium channel*, J Biol Chem, 1994, 269(39): p. 24261-70) is a member of the inward rectifier family of potassium channels expressed in two regions of the kidney: thick ascending loop of Henle (TALH) and cortical collecting duct (CCD) (see Hebert, S. C., et al., *Molecular diversity and regulation of renal potassium channels*, Physiol Rev, 2005, 85(1): p. 319-713). At the TALH, ROMK participates in potassium recycling across the luminal membrane which is critical for the function of the $Na^+/K^+/2Cl^-$ co-transporter, the rate-determining step for salt reuptake in this part of the nephron. At the CCD, ROMK provides a pathway for potassium secretion that is tightly coupled to sodium uptake through the amiloride-sensitive sodium channel (see Reinalter, S. C., et al., *Pharmacotyping of hypokalaemic salt-losing tubular disorders*, Acta Physiol Scand, 2004, 181(4): p. 513-21; and Wang, W., *Renal potassium channels: recent developments*, Curr Opin Nephrol Hypertens, 2004, 13(5): p. 549-55). Selective inhibitors of the ROMK channel (also referred to herein as inhibitors of ROMK or ROMK inhibitors) are predicted to represent novel diuretics for the treatment of hypertension and other conditions where treatment with a diuretic would be beneficial with potentially reduced liabilities (i.e., hypo- or hyperkalemia, new onset of diabetes, dyslipidemia) over the currently used clinical agents (see Lifton, R. P., A. G. Gharavi, and D. S. Geller, *Molecular mechanisms of human hypertension*, Cell, 2001, 104(4): p. 545-56). Human genetics (Ji, W., et al., *Rare independent mutations in renal salt handling genes contribute to blood pressure variation*, Nat Genet, 2008, 40(5): p. 592-9; and Tobin, M. D., et al., *Common variants in genes underlying monogenic hypertension and hypotension and blood pressure in the general population*, Hypertension, 2008, 51(6): p. 1658-64) and genetic ablation of ROMK in rodents (see Lorenz, J. N., et al., *Impaired renal NaCl absorption in mice lacking the ROMK potassium channel, a model for type II Bartter's syndrome*, J Biol Chem, 2002, 277(40): p. 37871-80 and Lu, M., et al., *Absence of small conductance K+ channel (SK) activity in apical membranes of thick ascending limb and cortical collecting duct in ROMK (Bartter's) knockout mice*, J Biol Chem, 2002, 277(40): p. 37881-7) support these expectations. To our knowledge, the first publicly disclosed small molecule selective inhibitors of ROMK, including VU590, were reported from work done at Vanderbilt University as described in Lewis, L. M., et al., *High-Throughput Screening Reveals a Small-Molecule Inhibitor of the Renal Outer Medullary Potassium Channel and Kir7.1*, Mol Pharmacol, 2009, 76(5): p. 1094-1103. The compound VU591 was later reported in Bhave, G. et al., *Development of a Selective Small-Molecule Inhibitor of Kir1.1, the Renal Outer Medullary Potassium Channel*, Mol Pharmacol, 2011, 79(1), p. 42-50, the text of which states that "ROMK (Kir1.1), is a putative drug target for a novel class of loop diuretics that would lower blood pressure without causing hypokalemia."

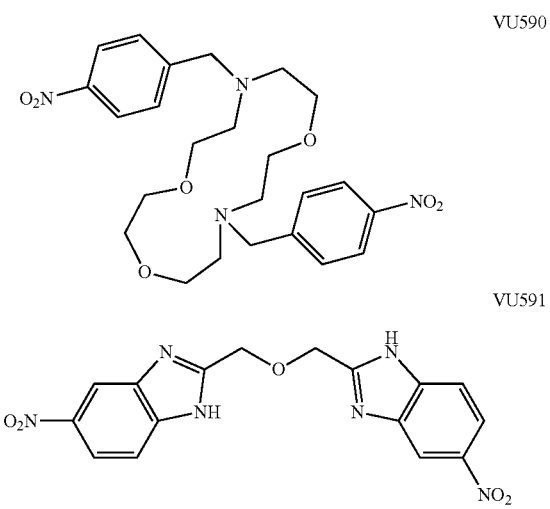

Patent application publication number WO2010/129379, published Nov. 11, 2010 having common representative Merck Sharp & Dohme Corp., (also published as US2010/0286123 on same date), describes ROMK inhibitors having the generic formula:

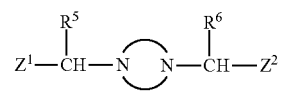

and, e.g., an embodiment

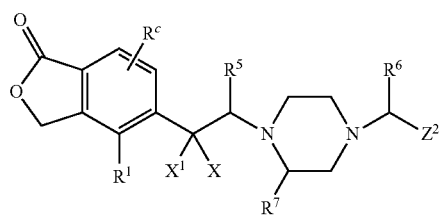

wherein $R^5$ and $R^6$ are independently —H, —$C_{1-6}$ alkyl, —$C_{3-6}$ cycloalkyl, —$CF_3$, —$CHF_2$, —$CH_2F$ or —$CH_2OH$; X is —H, —OH, —$OC_{1-3}$alkyl, —F, oxo, $NH_2$ or —$CH_3$; and $X^1$ is —H or —$CH_3$.

Patent application publication number WO2012/058134, published May 3, 2012, having common representative Merck Sharp & Dohme Corp., describes ROMK inhibitors having the generic formula:

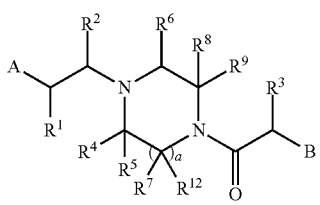

wherein A and B are mono and/or bicyclic aromatic groups; $R^2$ is —H, —$C_{1-6}$ alkyl, —$C_{3-6}$ cycloalkyl, $CF_3$, —$CH_2OH$, or —$CO_2R$, or $R^2$ can be joined to $R^1$ or $R^{10a}$ to form a ring; $R^3$ is —H, —$C_{1-6}$ alkyl, —$C_{3-6}$ cycloalkyl, —OH, —F, —$OC_{1-3}$ alkyl, or —$CH_2OH$, or $R^3$ can be joined to $R^{10b}$ to form a ring.

Patent application publication number WO2012/058116, published May 3, 2012, having common representative Merck Sharp & Dohme Corp., describes ROMK inhibitors having the generic formula:

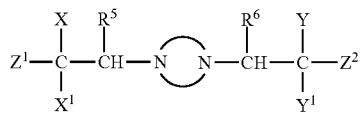

and, e.g., an embodiment

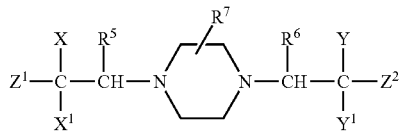

wherein $R^5$ and $R^6$ are independently —H, —$C_{1-6}$ alkyl or —$C(O)OC_{1-3}$alkyl; and X, $X^1$, Y and $Y^1$ are independently —H or —$C_{1-6}$alkyl; or $Y^1$ can be joined together with $Z^2$ to form a fused ring system.

However, continuing discovery of selective small molecule inhibitors of ROMK is still needed for the development of new treatments for hypertension and related disorders. The compounds of Formula I and salts thereof of this invention are selective inhibitors of the ROMK channel and could be used for the treatment of hypertension, heart failure and other conditions where treatment with a diuretic or natriuretic would be beneficial.

SUMMARY OF THE INVENTION

The present invention provides compounds of Formula I, defined herein, and the pharmaceutically acceptable salts thereof. The compounds of Formula I are inhibitors of the ROMK (Kir1.1) channel. As a result, the compounds of Formula I could be used in methods of treatment, inhibition or amelioration of one or more disease states that could benefit from inhibition of ROMK. The compounds of this invention could be used in methods of treatment which comprise administering a therapeutically or prophylactically effective amount of a compound of Formula I to a patient in need of a diuretic and/or natriuretic agent. Therefore, the compounds of Formula I could be valuable pharmaceutically active compounds for the therapy, prophylaxis or both of medical conditions, including, but not limited to, cardiovascular diseases such as hypertension and heart failure, and conditions associated with excessive salt and water retention. The compounds of this invention could further be used in combination with other therapeutically effective agents, including but not limited to, other drugs which are useful for the treatment of hypertension, heart failure and conditions associated with excessive salt and water retention. The invention furthermore relates to processes for preparing compounds of Formula I, and pharmaceutical compositions which comprise compounds of Formula I. These and other aspects of the invention will be evident from the description contained herein.

DETAILED DESCRIPTION OF THE INVENTION

The present invention is directed to compounds having structural Formula I:

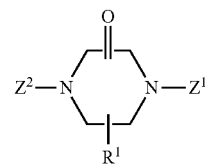

I and the pharmaceutically acceptable salts thereof wherein:

$Z^1$ is

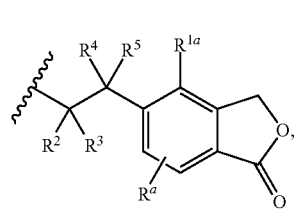

z1-a

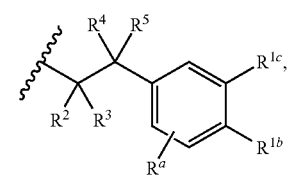

z1-b

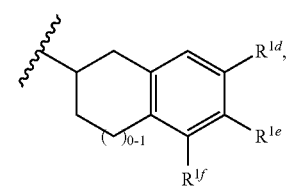

z1-c

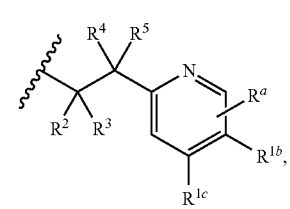

z1-d

-continued

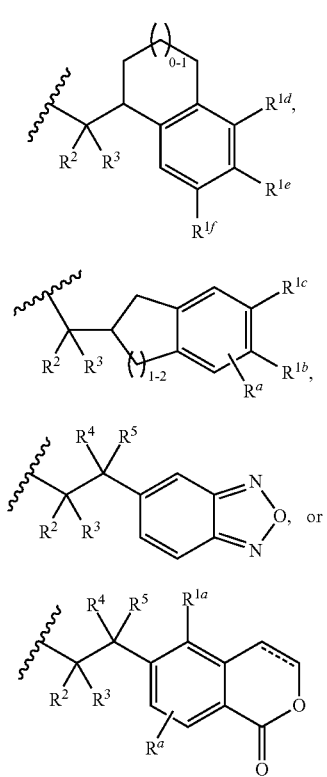

wherein the dashed line represents an optional double bond; $Z^2$ is

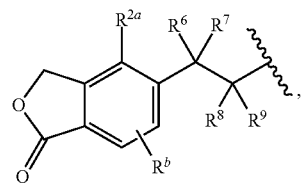

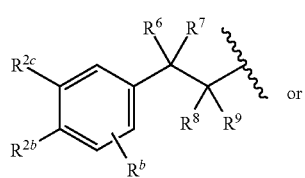

$R^1$ is —H, —CH$_3$, —CF$_3$, —CHF$_2$, —CH$_2$F or —CH$_2$OH;
$R^2$ is —H, oxo (=O) or —C$_{1-6}$alkyl;
$R^4$ is —H, —OH, oxo, —F or —C$_{1-6}$alkyl;
   provided that when $R^4$ is —OH, oxo or —F, then $R^2$ is not oxo;
$R^6$ is —H, —OH, oxo, —F or —C$_{1-6}$alkyl;
$R^8$ is —H, oxo or —C$_{1-6}$alkyl;
   provided that when $R^6$ is —OH, oxo or —F, then $R^8$ is not oxo;
$R^3$, $R^5$, $R^7$, and $R^9$ are each independently —H or —C$_{1-6}$alkyl;
   provided that $R^3$ is absent when $R^2$ is oxo, $R^5$ is absent when $R^4$ is oxo, $R^7$ is absent when $R^6$ is oxo, and $R^9$ is absent when $R^8$ is oxo;
$R^{1a}$ is —H, halo or —C$_{1-3}$alkyl optionally substituted with one to three of —F;
one of $R^{1b}$ and $R^{1c}$ is —CN, —NO$_2$ or tetrazolyl, and the other is —H, halo, —O—C$_{1-3}$alkyl, —COOC$_{1-3}$alkyl or —C$_{1-3}$alkyl optionally substituted with one to three of —F;
one of $R^{1d}$, $R^{1e}$ and $R^{1f}$ is —CN, —NO$_2$ or tetrazolyl, and each of the others is independently —H, halo, —O—C$_{1-3}$alkyl, —COOC$_{1-3}$alkyl or —C$_{1-3}$alkyl optionally substituted with one to three of —F;
$R^{2a}$ is —H, halo or —C$_{1-3}$alkyl optionally substituted with one to three of —F;
one of $R^{2b}$ and $R^{2c}$ is —CN, —NO$_2$ or tetrazolyl, and the other is —H, halo, —O—C$_{1-3}$alkyl, —COOC$_{1-3}$alkyl or —C$_{1-3}$alkyl optionally substituted with one to three of —F;
one of $R^{2d}$, $R^{2e}$ and $R^{2f}$ is —CN, —NO$_2$ or tetrazolyl, and each of the others is independently —H, halo, —O—C$_{1-3}$alkyl, —COOC$_{1-3}$alkyl or —C$_{1-3}$alkyl optionally substituted with one to three of —F; and
$R^a$ and $R^b$ are each independently —H, halo, —O—C$_{1-3}$alkyl, —COOC$_{1-3}$alkyl or —C$_{1-3}$alkyl optionally substituted with one to three of —F.

In one embodiment of this invention are compounds of Formula I having structural Formula II:

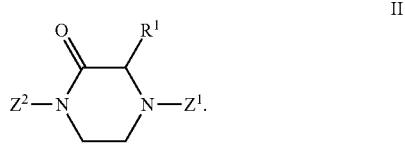

In another embodiment of this invention are compounds of Formula I or II wherein $Z^1$ is z1-a, z1-b, z1-d, z1-g or z1-h. In another embodiment are compounds of Formula I or II wherein $Z^1$ is z1-c, z1-e or z1-f.

In another embodiment of this invention are compounds of Formula I or II wherein $Z^2$ is

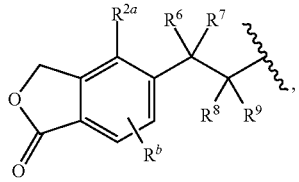

or more particularly z2-a wherein $R^{2a}$ is —H or —CH$_3$.

In another embodiment of this invention are compounds of Formula I or II wherein $Z^2$ is

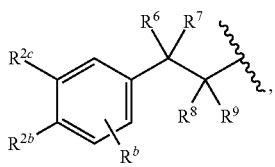

z2-b or more particularly z2-b wherein one of $R^{2b}$ and $R^{2c}$ is —CN or —NO$_2$ and the other is —H, halo, —O—C$_{1-3}$alkyl, —COOC$_{1-3}$alkyl or —C$_{1-3}$alkyl optionally substituted with one to three of —F.

In another embodiment of this invention are compounds of Formula I or II wherein $Z^2$ is

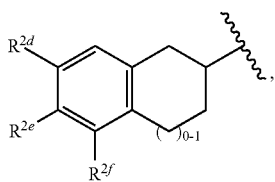

z2-c or more particularly it is

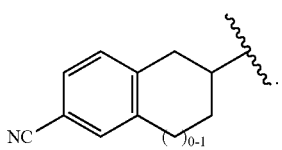

In another embodiment of this invention are compounds of Formula I having structural Formula III:

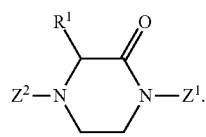

III

In a class of this embodiment are compounds of Formula III wherein $Z^2$ is z2-a, or more particularly z2-a wherein $R^{2a}$ is —H or —CH$_3$. In a further class of this embodiment are compounds wherein $Z^1$ is z1-d.

In another embodiment of this invention are compounds of Formula I or II or any one of the above embodiments wherein:
  a) $Z^1$ is z1-a, z1-b, z1-d, z1-g or z1-h and $Z^2$ is z2-a or z2-b, and
    (1) $R^2$, $R^3$, $R^4$, $R^5$, $R^6$, $R^7$, $R^8$ and $R^9$ are each —H; or
    (2) one or both of $R^4$ and $R^6$ are independently —OH, oxo or —F (or preferably —OH or oxo), and $R^1$, $R^2$, $R^3$, $R^5$, $R^7$ and $R^8$ are each —H; or
  b) $Z^1$ is z1-e or z1-f and $R^2$ is —H, or oxo and $R^3$ is —H; or
  c) $Z^1$ is z1-a, z1-b, z1-d, z1-g or z1-h and $Z^2$ is z2-c, and
    (1) $R^2$, $R^3$, $R^4$ and $R^5$ are each —H; or
    (2) $R^4$ is —OH, oxo or —F (or preferably —OH or oxo), and $R^2$, $R^3$ and $R^5$ are each —H.

All structural Formulas and embodiments described herein include the pharmaceutically acceptable salts of the compounds defined therein.

As used herein except if noted otherwise, "alkyl" is intended to include both branched- and straight-chain saturated aliphatic hydrocarbon groups having the specified number of carbon atoms. Commonly used abbreviations for alkyl groups are used throughout the specification. For example the term "C$_{1-6}$ alkyl" (or "C$_1$-C$_6$ alkyl"), means linear or branched chain alkyl groups, including all isomers, having the specified number of carbon atoms and includes all of the hexyl and pentyl isomers as well as n-, iso-, sec- and tert-butyl (butyl, s-butyl, i-butyl, t-butyl; Bu=butyl), n- and i-propyl (Pr=propyl), ethyl (Et) and methyl (Me). Halo means —F, —Cl, —Br and —I. In the Formula I, preferred halos are —F and —Cl.

Unless expressly depicted or described otherwise, variables depicted in a structural formula with a "floating" bond, such as $R^1$, are permitted on any available carbon atom in the ring to which the variable is attached.

Optional substitution on a chemical moiety encompasses the presence or absence of substituents on the specified moeity. For example, "—C$_{1-3}$alkyl optionally substituted with one to three of fluoro," describes unsubstituted C$_{1-3}$alkyl (e.g, —CH$_3$, —CH$_2$CH$_3$, —(CH$_2$)$_2$CH$_3$, or —CH(CH$_3$)$_2$), or fluoro-substituted C$_{1-3}$alkyl including but not limited to —CH$_2$F, —CHF$_2$, —CF$_3$ or —CH$_2$CF$_3$, etc. Tri-fluoromethyl is preferred.

The present invention encompasses all stereoisomeric forms of the compounds of Formula I. Centers of asymmetry that are present in the compounds of Formula I can all independently of one another have (R) or (S) configuration. When bonds to the chiral carbon are depicted as straight lines in the structural Formulas of the invention, or when a compound name is recited without a chiral designation for a chiral carbon, it is understood that both the (R) and (S) configurations of the chiral carbon and hence both enantiomers and mixtures thereof, are embraced within the Formula or by the name. The production of specific stereoisomers or mixtures thereof may be identified in the Examples where such stereoisomers or mixtures were obtained, but this in no way limits the inclusion of all stereoisomers and mixtures thereof from being within the scope of this invention.

The invention includes all possible enantiomers and diastereomers and mixtures of two or more stereoisomers, for example mixtures of enantiomers and/or diastereomers, in all ratios. Thus, enantiomers are a subject of the invention in enantiomerically pure form, both as levorotatory and as dextrorotatory antipodes, in the form of racemates and in the form of mixtures of the two enantiomers in all ratios. In the case of a cis/trans isomerism the invention includes both the cis form and the trans form as well as mixtures of these forms in all ratios. The preparation of individual stereoisomers can be carried out, if desired, by separation of a mixture by customary methods, for example by chromatography or crystallization, by the use of stereochemically uniform starting materials for the synthesis or by stereoselective synthesis. Optionally a derivatization can be carried out before a separation of stereoisomers. The separation of a mixture of stereoisomers can be carried out at an intermediate step during the synthesis of a compound of Formula I or it can be done on a final racemic product. Absolute stereochemistry may be determined by X-ray crystallography of crystalline products or crystalline intermediates which are derivatized, if necessary, with a reagent containing a stereogenic center of known configuration. Where compounds of this invention are capable of tautomerization, all individual tautomers as well as mixtures thereof are included in the scope of this invention. The present invention includes all such isomers, as well as salts, solvates (which includes hydrates) and solvated salts of such racemates, enantiomers, diastereomers and tautomers and mixtures thereof.

Reference to the compounds of Formula I herein encompasses the compounds of Formula II and all embodiments thereof. Reference to the compounds of this invention as those of a specific formula or embodiment or any other generic structural formula or specific compound described or claimed herein, is intended to encompass the specific compound or compounds falling within the scope of the Formula or embodiment, including salts thereof, particularly pharmaceutically acceptable salts, solvates (including hydrates) of such compounds and solvated (or hydrated) salt forms thereof, where such forms are possible unless specified otherwise.

In the compounds of Formula I, the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of Formula I. For example, different isotopic forms of hydrogen (H) include protium ($^1$H) and deuterium ($^2$H). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds within Formula I can be prepared without undue experimentation by conventional techniques well known to those skilled in the art or by processes analogous to those described in the Schemes and Examples herein using appropriate isotopically-enriched reagents and/or intermediates.

When the compounds of Formula I contain one or more acidic or basic groups the invention also includes the corresponding pharmaceutically acceptable salts. Thus, the compounds of Formula I which contain acidic groups can be used according to the invention, for example, as alkali metal salts, alkaline earth metal salts or as ammonium salts. Examples of such salts include but are not limited to sodium salts, potassium salts, calcium salts, magnesium salts or salts with ammonia or organic amines such as, for example, ethylamine, ethanolamine, triethanolamine or amino acids. Compounds of Formula I which contain one or more basic groups, i.e. groups which can be protonated, can be used according to the invention in the form of their acid addition salts with inorganic or organic acids as, for example but not limited to, salts with hydrogen chloride, hydrogen bromide, phosphoric acid, sulfuric acid, nitric acid, benzenesulfonic acid, methanesulfonic acid, p-toluenesulfonic acid, naphthalenedisulfonic acids, oxalic acid, acetic acid, trifluoroacetic acid, tartaric acid, lactic acid, salicylic acid, benzoic acid, formic acid, propionic acid, pivalic acid, diethylacetic acid, malonic acid, succinic acid, pimelic acid, fumaric acid, maleic acid, malic acid, sulfaminic acid, phenylpropionic acid, gluconic acid, ascorbic acid, isonicotinic acid, citric acid, adipic acid, etc. If the compounds of Formula I simultaneously contain acidic and basic groups in the molecule the invention also includes, in addition to the salt forms mentioned, inner salts or betaines (zwitterions). Salts can be obtained from the compounds of Formula I by customary methods which are known to the person skilled in the art, for example by combination with an organic or inorganic acid or base in a solvent or dispersant, or by anion exchange or cation exchange from other salts. The present invention also includes all salts of the compounds of Formula I which, owing to low physiological compatibility, are not directly suitable for use in pharmaceuticals but which can be used, for example, as intermediates for chemical reactions or for the preparation of pharmaceutically acceptable salts.

Furthermore, compounds of the present invention may exist in amorphous form and/or one or more crystalline forms, and as such all amorphous and crystalline forms and mixtures thereof of the compounds of Formula I are intended to be included within the scope of the present invention. In addition, some of the compounds of the instant invention may form solvates with water (i.e., a hydrate) or common organic solvents. Such solvates and hydrates, particularly the pharmaceutically acceptable solvates and hydrates, of the instant compounds are likewise encompassed within the scope of this invention, along with un-solvated and anhydrous forms.

Any pharmaceutically acceptable pro-drug modification of a compound of this invention which results in conversion in vivo to a compound within the scope of this invention is also within the scope of this invention. For example, esters can optionally be made by esterification of an available carboxylic acid group or by formation of an ester on an available hydroxy group in a compound. Similarly, labile amides can be made. Pharmaceutically acceptable esters or amides of the compounds of this invention may be prepared to act as pro-drugs which can be hydrolyzed back to an acid (or —COO— depending on the pH of the fluid or tissue where conversion takes place) or hydroxy form particularly in vivo and as such are encompassed within the scope of this invention. Examples of pharmaceutically acceptable pro-drug modifications include, but are not limited to, —$C_{1-6}$alkyl esters and —$C_{1-6}$alkyl substituted with phenyl esters.

Accordingly, the compounds within the generic structural formulas, embodiments and specific compounds described and claimed herein encompass salts, all possible stereoisomers and tautomers, physical forms (e.g., amorphous and crystalline forms), solvate and hydrate forms thereof and any combination of these forms, as well as the salts thereof, pro-drug forms thereof, and salts of pro-drug forms thereof, where such forms are possible unless specified otherwise.

The compounds of Formula I according to the invention are inhibitors of ROMK, and therefore could be used as diuretic and/or natriuretic agents. ROMK inhibitors may be used to help to increase urination and increase urine volume and also to prevent or reduce reabsorption of sodium in the kidneys leading to increased excretion of sodium and water. Therefore, the compounds could be used for treatment or prophylaxis or both of disorders that benefit from increased excretion of water and sodium from the body. Accordingly, the compounds of this invention could be used in a method for inhibiting ROMK comprising administering a compound of Formula I in a ROMK-inhibitory effective amount to a patient in need thereof. The inhibition of ROMK by the compounds of Formula I can be examined, for example, in the Thallium Flux Assay and/or $^{86}$Rb$^+$ Efflux Assay described below. Moreover, this invention also relates to the use of the compounds of Formula I or salts thereof to validate in vitro assays, for example but not limited to the Thallium Flux and $^{86}$Rb$^+$ Efflux Assays described herein.

The compounds of this invention could be used in a method for causing diuresis, natriuresis or both, comprising administering a compound of Formula I in a therapeutically effective amount to a patient in need thereof. Therefore, the compounds of Formula I of this invention could be used in methods for treatment of, prevention of or reduction of risk for developing medical conditions that benefit from increased excretion of water and sodium, such as but not limited to one or more of hypertension, heart failure (both acute and chronic, the latter also known as congestive heart failure) and/or other conditions associated with excessive salt and water retention. Furthermore, the compounds of Formula I could be used in methods for treatment of, prevention of or reduction of risk for developing one or more disorders such as pulmonary arterial hypertension (PAH), cardiovascular disease, diabetes mellitus, diabetes insipidus, post-operative volume overload, endothelial dysfunction, diastolic dysfunction, systolic dysfunction, stable and unstable angina pectoris, thromboses, restenosis, myocardial infarction, stroke, cardiac insufficiency, pulmonary hypertonia, atherosclerosis, hepatic cirrhosis, ascites, pre-eclampsia, cerebral edema, nephropathy, glomerulonephritis, nephrotic syndrome, acute and chronic kidney insufficiency (also referred to as chronic kidney disease, or more generally as renal impairment), acute tubular necrosis, hypercalcemia, idiopathic edema, Dent's disease, Meniere's disease, edematous states, glaucoma, benign intracranial hypertension, and other conditions for which a diuretic or natriuretic or both would have therapeutic or prophylactic benefit. The compounds of the invention may be administered to a patient having, or at risk of having, one or more conditions for which a diuretic or natriuretic or both would have therapeutic or prophylactic benefit such as those described herein.

The compounds of Formula I may potentially have reduced liabilities (for example, hypo- or hyperkalemia, new onset of diabetes, dyslipidemia, etc.) over currently used clinical agents. Also the compounds may have reduced risk for diuretic tolerance, which can be a problem with long-term use of loop diuretics.

In general, compounds that are ROMK inhibitors can be identified as those compounds which, when tested, have an $IC_{50}$ of 5 µM or less, preferably 1 µM or less, and more preferably 0.25 µM or less, in at least one of the following assays: 1) Thallium Flux Assay, 2) $^{86}Rb^+$ Efflux Assay. These assays are described in more detail further below.

The dosage amount of the compound to be administered depends on the individual case and is, as is customary, to be adapted to the individual circumstances to achieve an optimum effect. Thus, it depends on the nature and the severity of the disorder to be treated, and also on the sex, age, weight and individual responsiveness of the human or animal to be treated, on the efficacy and duration of action of the compounds used, on whether the therapy is acute or chronic or prophylactic, or on whether other active compounds are administered in addition to compounds of Formula I. A consideration of these factors is well within the purview of the ordinarily skilled clinician for the purpose of determining the therapeutically effective or prophylactically effective dosage amount needed to prevent, counter, or arrest the progress of the condition. It is expected that the compound will be administered chronically on a daily basis for a length of time appropriate to treat or prevent the medical condition relevant to the patient, including a course of therapy lasting days, months, years or the life of the patient.

In general, a daily dose of approximately 0.001 to 100 mg/kg, preferably 0.001 to 30 mg/kg, in particular 0.001 to 10 mg/kg (in each case mg per kg of bodyweight) is appropriate for administration to an adult weighing approximately 75 kg in order to obtain the desired results. The daily dose is preferably administered in a single dose or can be divided into several, for example two, three or four individual doses, and may be, for example but not limited to, 0.1 mg, 0.25 mg, 0.5 mg, 0.75 mg, 1 mg, 1.25 mg, 2 mg, 2.5 mg, 5 mg, 10 mg, 20 mg, 40 mg, 50 mg, 75 mg, 100 mg, 125 mg, 150 mg, 175 mg, 200 mg, etc., on a daily basis. In some cases, depending on the individual response, it may be necessary to deviate upwards or downwards from the given daily dose. Furthermore, the compound may be formulated for immediate or modified release such as extended or controlled release.

The term "patient" includes animals, preferably mammals and especially humans, who use the instant active agents for the prophylaxis or treatment of a medical condition. Administering of the drug to the patient includes both self-administration and administration to the patient by another person. The patient may be in need of treatment for an existing disease or medical condition, or may desire prophylactic treatment to prevent or reduce the risk for developing said disease or medical condition or developing long-term complications from a disease or medical condition.

The term therapeutically effective amount is intended to mean that amount of a drug or pharmaceutical agent that will elicit the biological or medical response of a tissue, a system, animal or human that is being sought by a researcher, veterinarian, medical doctor or other clinician. A prophylactically effective amount is intended to mean that amount of a pharmaceutical drug that will prevent or reduce the risk of occurrence of the biological or medical event that is sought to be prevented in a tissue, a system, animal or human by a researcher, veterinarian, medical doctor or other clinician. It is understood that a specific daily dosage amount can simultaneously be both a therapeutically effective amount, e.g., for treatment of hypertension, and a prophylactically effective amount, e.g., for prevention or reduction of risk of myocardial infarction or prevention and reduction of risk for complications related to hypertension.

In the methods of treatment of this invention, the ROMK inhibitors may be administered via any suitable route of administration such as, for example, orally, parenterally, or rectally in dosage unit formulations containing conventional non-toxic pharmaceutically acceptable carriers, adjuvants and vehicles. The term parenteral as used herein includes subcutaneous injections, intravenous (IV), intramuscular, intrasternal injection or infusion techniques. Oral formulations are preferred for treatment of chronic indications such as hypertension or chronic heart failure, particularly solid oral dosage units such as pills, tablets or capsules, and more particularly tablets. IV dosing is preferred for acute treatment, for example for the treatment of acute heart failure.

This invention also provides pharmaceutical compositions comprised of a compound of Formula I and a pharmaceutically acceptable carrier which is comprised of one or more excipients or additives. An excipient or additive is an inert substance used to formulate the active drug ingredient. For oral use, the pharmaceutical compositions of this invention containing the active ingredient may be in forms such as pills, tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions. Tablets contain the active ingredient in admixture with non-toxic pharmaceutically acceptable excipients which are suitable for the manufacture of tablets. The excipients may be for example, inert diluents, such as calcium carbonate, sodium carbonate, lactose, mannitol, calcium phosphate or sodium phosphate; granulating and disintegrating agents, for example, corn starch, or alginic acid; binding agents, for example starch, gelatin or acacia, and lubricating agents, for example, magnesium stearate, stearic acid or talc.

Pharmaceutical compositions may also contain other customary additives, for example but not limited to, wetting agents, stabilizers, emulsifiers, dispersants, preservatives, sweeteners, colorants, flavorings, aromatizers, thickeners, buffer substances, solvents, solubilizers, agents for achieving a depot effect, salts for altering the osmotic pressure, coating agents or antioxidants.

Oral immediate-release and time-controlled release dosage forms may be employed, as well as enterically coated oral dosage forms. Tablets may be uncoated or they may be coated by known techniques for aesthetic purposes, to mask taste or for other reasons. Coatings can also be used to delay disintegration and absorption in the gastrointestinal tract and thereby provide a sustained action over a longer period. For example, a time delay material such as glyceryl monostearate or glyceryl distearate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredients is mixed with water or miscible solvents such as propylene glycol, PEGs and ethanol, or an oil medium, for example peanut oil, liquid paraffin, or olive oil.

Aqueous suspensions contain the active material in admixture with excipients suitable for the manufacture of aqueous suspensions. Oily suspensions may be formulated by suspending the active ingredient in a vegetable oil, for example arachis oil, olive oil, sesame oil or coconut oil, or in mineral oil such as liquid paraffin. The oily suspensions may contain a thickening agent, for example beeswax, hard paraffin or cetyl alcohol. Sweetening agents and flavoring agents may be added to provide a palatable oral preparation. These compositions may be preserved by the addition of an anti-oxidant such as ascorbic acid. Syrups and elixirs may be formulated with sweetening agents, for example glycerol, propylene glycol, sorbitol or sucrose.

The instant invention also encompasses a process for preparing a pharmaceutical composition comprising combining a compound of Formula I with a pharmaceutically acceptable carrier. Also encompassed is the pharmaceutical composition which is made by combining a compound of Formula I with a pharmaceutically acceptable carrier. Furthermore, a therapeutically effective amount of a compound of this invention can be used for the preparation of a medicament useful for inhibiting ROMK, for causing diuresis and/or natriuresis, and/or for treating, preventing or reducing the risk for any of the medical conditions described herein, in dosage amounts described herein.

The amount of active compound of Formula I and/or its pharmaceutically acceptable salts in the pharmaceutical composition may be, for example but not limited to, from 0.1 to 200 mg, particularly from 0.1 to 100 mg, and more particularly from 0.1 to 50 mg, per dose on a free acid/free base weight basis, but depending on the type of the pharmaceutical composition, potency of the active ingredient and/or the medical condition being treated, it could also be lower or higher. Pharmaceutical compositions usually comprise 0.5 to 90 percent by weight of the active compound on a free acid/free base weight basis.

The compounds of Formula I inhibit ROMK. On account of this property, apart from use as pharmaceutically active compounds in human medicine and veterinary medicine, they can also be employed as a scientific tool or as aid for biochemical investigations in which such an effect on ROMK is intended, and also for diagnostic purposes, for example in the in vitro diagnosis of cell samples or tissue samples. The compounds of Formula I can also be employed as intermediates for the preparation of other pharmaceutically active compounds.

One or more additional pharmacologically active agents may be administered in combination with a compound of Formula I. The additional active agent (or agents) is intended to mean a medicinal compound that is different from the compound of Formula I, and which is a pharmaceutically active agent (or agents) that is active in the body, including pro-drugs, for example esterified forms, that convert to pharmaceutically active form after administration, and also includes free-acid, free-base and pharmaceutically acceptable salts of said additional active agents when such forms are sold commercially or are otherwise chemically possible. Generally, any suitable additional active agent or agents, including but not limited to anti-hypertensive agents, additional diuretics, anti-atherosclerotic agents such as a lipid modifying compound, anti-diabetic agents and/or anti-obesity agents may be used in any combination with the compound of Formula I in a single dosage formulation (a fixed dose drug combination), or may be administered to the patient in one or more separate dosage formulations which allows for concurrent or sequential administration of the active agents (co-administration of the separate active agents). Examples of the one or more additional active agents which may be employed include but are not limited to thiazide-like diuretics, e.g., hydrochlorothiazide (HCTZ or HCT); angiotensin converting enzyme inhibitors (e.g, alacepril, benazepril, captopril, ceronapril, cilazapril, delapril, enalapril, enalaprilat, fosinopril, imidapril, lisinopril, moveltipril, perindopril, quinapril, ramipril, spirapril, temocapril, or trandolapril); dual inhibitors of angiotensin converting enzyme (ACE) and neutral endopeptidase (NEP) such as omapatrilat, sampatrilat and fasidotril; angiotensin II receptor antagonists, also known as angiotensin receptor blockers or ARBs, which may be in free-base, free-acid, salt or pro-drug form, such as azilsartan, e.g., azilsartan medoxomil potassium (EDARBI®), candesartan, e.g., candesartan cilexetil (ATACAND®), eprosartan, e.g., eprosartan mesylate (TEVETAN®), irbesartan (AVAPRO®), losartan, e.g., losartan potassium (COZAAR®), olmesartan, e.g, olmesartan medoximil (BENICAR®), telmisartan (MICARDIS®), valsartan (DIOVAN®), and any of these drugs used in combination with a thiazide-like diuretic such as hydrochlorothiazide (e.g., HYZAAR®, DIOVAN HCT®, ATACAND HCT®), etc.); potassium sparing diuretics such as amiloride HCl, spironolactone, epleranone, triamterene, each with or without HCTZ; carbonic anhydrase inhibitors, such as acetazolamide, neutral endopeptidase inhibitors (e.g., thiorphan and phosphoramidon); aldosterone antagonists; aldosterone synthase inhibitors; renin inhibitors (e.g. urea derivatives of di- and tri-peptides (See U.S. Pat. No. 5,116,835), amino acids and derivatives (U.S. Pat. Nos. 5,095,119 and 5,104,869), amino acid chains linked by non-peptidic bonds (U.S. Pat. No. 5,114,937), di- and tri-peptide derivatives (U.S. Pat. No. 5,106,835), peptidyl amino diols (U.S. Pat. Nos. 5,063,208 and 4,845,079) and peptidyl beta-aminoacyl aminodiol carbamates (U.S. Pat. No. 5,089,471); also, a variety of other peptide analogs as disclosed in the following U.S. Pat. Nos. 5,071,837; 5,064,965; 5,063,207; 5,036,054; 5,036,053; 5,034,512 and 4,894,437, and small molecule renin inhibitors (including diol sulfonamides and sulfinyls (U.S. Pat. No. 5,098,924), N-morpholino derivatives (U.S. Pat. No. 5,055, 466), N-heterocyclic alcohols (U.S. Pat. No. 4,885,292) and pyrolimidazolones (U.S. Pat. No. 5,075,451); also, pepstatin derivatives (U.S. Pat. No. 4,980,283) and fluoro- and chloro-derivatives of statone-containing peptides (U.S. Pat. No. 5,066,643); enalkrein; RO 42-5892; A 65317; CP 80794; ES 1005; ES 8891; SQ 34017; aliskiren (2(S),4(S),5(S),7(S)—N-(2-carbamoyl-2-methylpropyl)-5-amino-4-hydroxy-2,7-diisopropyl-8-[4-methoxy-3-(3-methoxypropoxy)-phenyl]-octanamid hemifumarate) SPP600, SPP630 and SPP635;

endothelin receptor antagonists; vasodilators (e.g. nitroprusside); calcium channel blockers (e.g., amlodipine, nifedipine, verapamil, diltiazem, felodipine, gallopamil, niludipine, nimodipine, nicardipine, bepridil, nisoldipine); potassium channel activators (e.g., nicorandil, pinacidil, cromakalim, minoxidil, aprilkalim, loprazolam); sympatholitics; beta-adrenergic blocking drugs (e.g., acebutolol, atenolol, betaxolol, bisoprolol, carvedilol, metoprolol, metoprolol tartate, nadolol, propranolol, sotalol, timolol); alpha adrenergic blocking drugs (e.g., doxazocin, prazocin or alpha methyldopa); central alpha adrenergic agonists; peripheral vasodilators (e.g. hydralazine); nitrates or nitric oxide donating compounds eg isosorbide mononitrate, lipid lowering agents, e.g., HMG-CoA reductase inhibitors such as simvastatin and lovastatin which are marketed as ZOCOR® and MEVACOR® in lactone pro-drug form and function as inhibitors after administration, and pharmaceutically acceptable salts of dihydroxy open ring acid HMG-CoA reductase inhibitors such as atorvastatin (particularly the calcium salt sold in LIPITOR®), rosuvastatin (particularly the calcium salt sold in CRESTOR®), pravastatin (particularly the sodium salt sold in PRAVACHOL®), and fluvastatin (particularly the sodium salt sold in LESCOL®); a cholesterol absorption inhibitor such as ezetimibe (ZETIA®), and ezetimibe in combination with any other lipid lowering agents such as the HMG-CoA reductase inhibitors noted above and particularly with simvastatin (VYTORIN®) or with atorvastatin calcium; niacin in immediate-release or controlled release forms, and particularly niacin in combination with a DP antagonist such as laropiprant (TREDAPTIVE®) and/or with an HMG-CoA reductase inhibitor; niacin in immediate-release or controlled release forms, and particularly niacin in combination with a DP antagonist such as laropiprant (TREDAPTIVE®) and/or with an HMG-CoA reductase inhibitor; niacin receptor agonists such as acipimox and acifran, as well as niacin receptor partial agonists; metabolic altering agents including insulin sensitizing agents and related compounds for the treatment of diabetes such as biguanides (e.g., metformin), meglitinides (e.g., repaglinide, nateglinide), sulfonylureas (e.g., chlorpropamide, glimepiride, glipizide, glyburide, tolazamide, tolbutamide), thiazolidinediones also referred to as glitazones (e.g., pioglitazone, rosiglitazone), alpha glucosidase inhibitors (e.g., acarbose, miglitol), dipeptidyl peptidase inhibitors, (e.g., sitagliptin (JANUVIA®), alogliptin, vildagliptin, saxagliptin, linagliptin, dutogliptin, gemigliptin), ergot alkaloids (e.g., bromocriptine), combination medications such as JANUMET® (sitagliptin with metformin), and injectable diabetes medications such as exenatide and pramlintide acetate; or with other drugs beneficial for the prevention or the treatment of the above-mentioned diseases including but not limited to diazoxide; and including the free-acid, free-base, and pharmaceutically acceptable salt forms, pro-drug forms including but not limited to esters, and salts of pro-drugs of the above medicinal agents where chemically possible. Trademark names of pharmaceutical drugs noted above are provided for exemplification of the marketed form of the active agent(s); such pharmaceutical drugs could be used in a separate dosage form for concurrent or sequential administration with a compound of Formula I, or the active agent(s) therein could be used in a fixed dose drug combination including a compound of Formula I.

Several methods for preparing the compounds of this invention are described in the examples. Starting materials and intermediates are purchased, made from known procedures, or as otherwise illustrated. Some frequently applied routes to the compounds of Formula I are also described by the Schemes as follows. In some cases the order of carrying out the steps of reaction schemes may be varied to facilitate the reaction or to avoid unwanted reaction products. The Ar group shown in the below Schemes can represent any of the mono- or bi-cyclic rings at the terminal end of $Z^1$ or $Z^2$ as defined previously.

As shown in Scheme 1, synthesis of intermediates of formula 1-9 started with treating allylamine (1-2) with the corresponding aldehyde/ketone (1-1, W=C(O)R) under standard reductive amination conditions with a suitable reducing agent such as sodium cyanoborohydride or sodium triacetoxyborohydride, or with alkyl halide (W=C(R)(R)-Hal; Hal=Br or I) under standard alkylation conditions in the presence of a suitable base (triethylamine or sodium carbonate). The resulting amine 1-3 was then protected with the Boc group to afford 1-4 (Greene, T.; Wuts, P. G. M. *protective Groups in Organic Synthesis*, John Wiley and Sons, Inc., New York, N.Y. 1991), which was further subjected to oxidation conditions to furnish aldehyde 1-5. Aldehyde 1-5 was next reacted with glycine ethyl ester (1-6) under reductive amination conditions to furnish 1-7. Subsequent removal of the Boc group with trifluoroacetic acid or HCl gave rise to 1-8, which can be cyclized to form the keto-piperazine 1-9 at elevated temperatures in the presence of base.

SCHEME 1

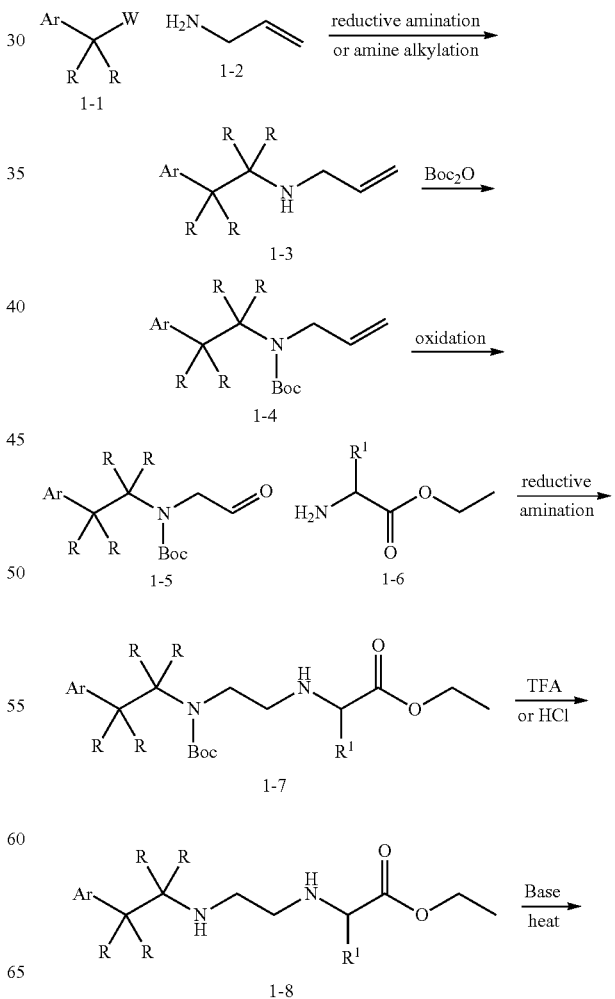

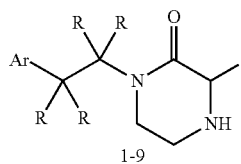

1-9

SCHEME 3

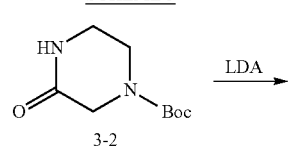

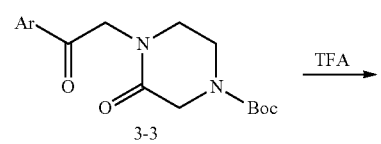

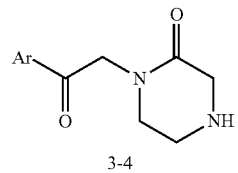

3-4

Keto-piperazine intermediate 2-6 can also be formed via the sequence described in Scheme 2. Alkylation of 1-1 with tert-butyl(2-aminoethyl)carbamate (2-1) gave rise to 2-2, which was then reacted with chloroacetyl chloride (2-3) to furnish 2-4. The Boc group of 2-4 was removed under acidic conditions, and subsequent treatment of 2-5 with base produced keto-piperazine 2-6.

SCHEME 2

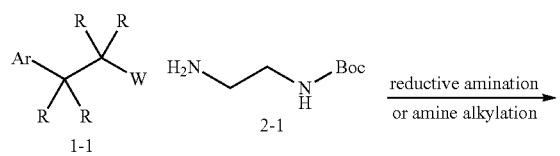

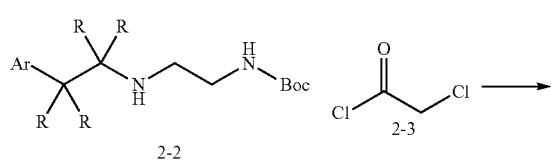

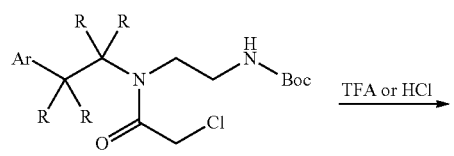

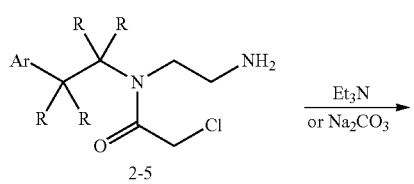

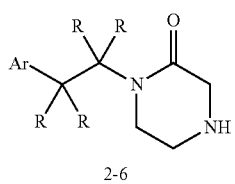

2-6

For compounds 3-4 with a carbonyl at the benzylic position, synthesis started with the corresponding bromo-ketone 3-1, which was accessed from the corresponding Aryl halide (for a related reference, see: *Bioorganic & Medicinal Chemistry Letters* 2003, 13(12), 2059-2063). Alkylation of 3-1 with N-Boc keto-piperazine 3-2 gave rise to 3-3, which upon removal of the Boc group provides keto-piperazine 3-4.

With the keto-piperazine intermediates in hand, compounds of formula II-1 can be obtained via reductive amination with the corresponding aldehyde/ketone (4-1, W═C(O)R), or alkylation with the corresponding alkyl halide (4-1, W═C(R)(H)-Hal; Hal=Br or I), as shown in Scheme 4. Compounds of formula II-2 were prepared by opening of epoxide 4-2 (Nomura, Y. et al. *Chemical & Pharmaceutical Bulletin*, 1995, 43(2), 241-6). Compounds of formula II-3 were prepared by EDC coupling of keto-piperazine 2-6 with the corresponding acid.

SCHEME 4

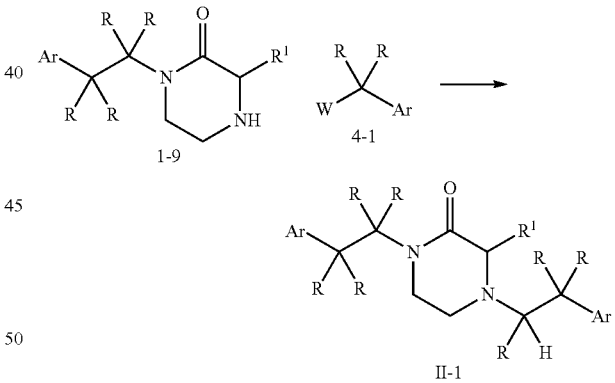

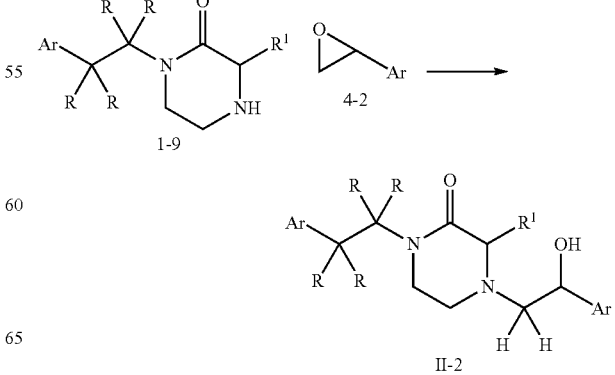

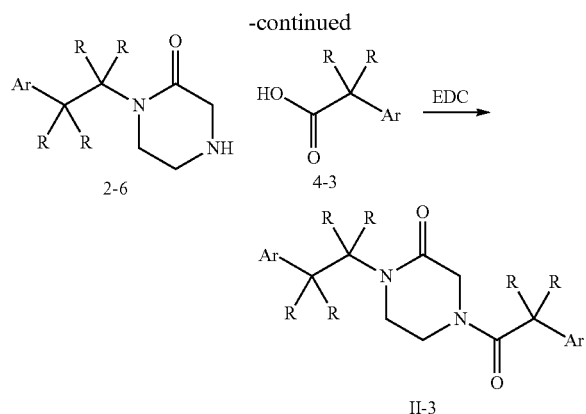

The independent synthesis of diastereomers and enantiomers or their chromatographic separations may be achieved as known in the art by appropriate modification of the methodology disclosed herein. Their absolute stereochemistry may be determined by x-ray crystallography of crystalline products or crystalline intermediates which are derivatized, if necessary, with a reagent containing an asymmetric center of known absolute stereochemistry.

The subject compounds may be prepared by modification of the procedures disclosed in the Examples as appropriate. Starting materials are commercially available or made by known procedures or as illustrated. The following examples are provided for the purpose of further illustration only and are not intended to be limitations on the disclosed invention.

Reactions sensitive to moisture or air were performed under nitrogen or argon using anhydrous solvents and reagents. The progress of reactions was determined by either analytical thin layer chromatography (TLC) usually performed with E. Merck precoated TLC plates, silica gel 60F-254, layer thickness 0.25 mm or liquid chromatography-mass spectrometry (LC-MS; also referred to as "LC" in the experimental procedures herein). Typically the analytical LC-MS system used consisted of a Waters ZQ platform with electrospray ionization in positive ion detection mode with an Agilent 1100 series HPLC with autosampler. The column was usually a Water Xterra MS C18, 3.0×50 example 49 mm, 5 µm. The flow rate was 1 mL/min, and the injection volume was 10 µL. UV detection was in the range 210-400 nm. The mobile phase consisted of solvent A (water plus 0.06% TFA) and solvent B (acetonitrile plus 0.05% TFA) with a gradient of 100% solvent A for 0.7 min changing to 100% solvent B over 3.75 min, maintained for 1.1 min, then reverting to 100% solvent A over 0.2 min.

Preparative HPLC purifications were usually performed using a mass spectrometry directed system. Usually they were performed on a Waters Chromatography Workstation configured with LC-MS System Consisting of: Waters ZQ single quad MS system with Electrospray Ionization, Waters 2525 Gradient Pump, Waters 2767 Injector/Collector, Waters 996 PDA Detector, the MS Conditions of: 150-750 amu, Positive Electrospray, Collection Triggered by MS, and a Waters Sunfire C-18 5 micron, 30 mm (id)×100 mm column. The mobile phases consisted of mixtures of acetonitrile (10-100%) in water containing 0.1% TFA. Flow rates were maintained at 50 mL/min, the injection volume was 1800 µL, and the UV detection range was 210-400 nm. Mobile phase gradients were optimized for the individual compounds.

Reactions performed using microwave irradiation were normally carried out using an Emrys Optimizer manufactured by Personal Chemistry, or an Initiator manufactured by Biotage. Concentration of solutions was carried out on a rotary evaporator under reduced pressure. Flash chromatography was usually performed using a Biotage Flash Chromatography apparatus (Dyax Corp.) on silica gel (32-63 mM, 60 Å pore size) in pre-packed cartridges of the size noted. $^1$H NMR spectra were acquired at 500 MHz spectrometers in CDCl$_3$ solutions unless otherwise noted. Chemical shifts were reported in parts per million (ppm). Tetramethylsilane (TMS) was used as internal reference in CD$_3$Cl solutions, and residual CH$_3$OH peak or TMS was used as internal reference in CD$_3$OD solutions. Coupling constants (J) were reported in hertz (Hz). Chiral analytical chromatography was performed on one of Chiralpak AS, Chiralpak AD, Chiralcel OD, Chiralcel IA, or Chiralcel OJ columns (250×4.6 mm) (Daicel Chemical Industries, Ltd.) with noted percentage of either ethanol in hexane (% Et/Hex) or isopropanol in heptane (% IPA/Hep) as isocratic solvent systems. Chiral preparative chromatography was conducted on one of Chiralpak AS, Chiralpak AD, Chiralcel OD, Ciralcel IA, or Chiralcel OJ columns (20×250 mm) (Daicel Chemical Industries, Ltd.) with desired isocratic solvent systems identified on chiral analytical chromatography or by supercritical fluid chromatography (SFC) conditions.

In the Examples, when a compound is obtained via chromatography (e.g., MPLC, HPLC, silica gel), it means that the solvent was removed (generally under vacuum) after the chromatography step to obtain the isolated product.

Abbreviations used herein include: —C(O)CH$_3$ (Ac); acetic acid (AcOH); —OC(O)CH$_3$ (OAc); aqueous (aq); Cbz (benzyloxycarbonyl); N,N-diisopropylethylamine (DIEA); N;N-dimethylformamide (DMF); ethyl acetate (EtOAc; EA); diethyl ether (ether or Et$_2$O); petroleum ether (Pet Ether; PE); 2-propanol (IPA); methyl t-butylether (MTBE); (benzotriazol-1-yloxy)tripyrrolidino-phosphonium hexafluorophosphate (PyBOP); saturated aq sodium chloride solution (brine); trifluoroacetic acid (TFA); tetrahydrofuran (THF); t-butyloxycarbonyl (Boc or BOC); Diethylaminosulfur trifluoride (DAST); dichloromethane (DCM); dimethylacetamide (DMA; DMAC); dimethylsulfoxide (DMSO); 1,3-Bis(diphenylphosphino)propane (DPPP); acetic acid (HOAc); 3-chloroperoxybenzoic acid (m-CPBA); methyl (Me); methanol (MeOH); N-bromosuccinamide (NBS); N-methylmorpholine N-oxide (NMO); 1-hydroxybenzotriazole (HOBt); N-(3-dimethylaminopropyl)-N'-ethylcarbodiimide hydrochloride (EDC); diisopropyl azodicarboxylate (DIAD); lithium diisopropylamide (LDA); triethyl amine (TEA); di-tert-butydicarboxylate (BOC$_2$O); glycine methyl ester (Gly-OMe); dimethyl sulfide (DMS); dichloroethane (DCE); N-iodosuccinamide (NIS); triflic acid or trifluoromethanesulfonic acid (TfOH); N-methyl morpholine (NMP); methanesulfonyl chloride (MsCl); 1,8-diazabicyclo[5.4.0]-undec-7-ene (DUB); p-toulenesulfonylmethyl isocyanide (TosMIC); dimethoxyethane (DME); tetramethyl ethylene diamine (TMEDA); 4-dimethylamino pyridine (DMAP); Pd$_2$dba$_3$ (Tris(dibenzylideneacetone)dipalladium(0)); Xantphos (4,5-Bis(diphenylphosphino)-9,9-dimethylxanthene); gram(s) (g); milligram(s) (mg); microliter(s) (µL); milliliter(s) (mL); millimole (mmol); minute(s) (min, mins); hour(s) (h, hr or hrs); retention time (R$_t$); room temperature (rt, r.t. or RT); round bottom (RB); thin layer chromatography (TLC); flash chromatography (FC); liquid chromatography-mass spectrometry (LCMS or LC-MS); supercritical fluid chromatography (SFC); Medium Pressure Liquid Chromatography (MPLC); High Pressure Liquid Chromatography (HPLC); mass spectrum (ms or MS). Celite is the tradename for diatomaceous earth filter aid.

The following are representative procedures for the preparation of the compounds used in the following Examples, or which can be substituted for the compounds used in the following Examples which may not be commercially available.

Intermediate 1

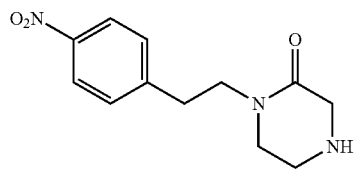 [SMILES: O=C1CNCCN1CCc1ccc([N+](=O)[O-])cc1]

1-[2-(4-Nitrophenyl)ethyl]piperazin-2-one

Step A: tert-Butyl allyl[2-(4-nitrophenyl)ethyl]carbamate

A solution of 1-(2-bromoethyl)-4-nitrobenzene (1.0 g, 4.4 mmol), allylamine (300 mg, 5.2 mmol) was heated with triethylamine (1.1 mL, 11 mmol) to 50° C. for 16 hours. LC showed formation of the desired product. After the solution was cooled, BOC anhydride (1.9 g, 8.7 mmol) was added to the reaction. After stirring the mixture for another 30 minutes, the reaction was diluted with EtOAc, washed with brine, dried over sodium sulfate, concentrated and purified by silica gel chromatography (Hexane:EtOAc) to furnish the tiel compound. LC-MS (IE, m/z): 307 [M+1]$^+$.

Step B: tert-Butyl [2-(4-nitrophenyl)ethyl](2-oxoethyl)carbamate

To a solution of 1-(2-Bromoethyl)-4-nitrobenzene (550 mg, 1.8 mmol) was added Osmium Tetraoxide (0.028 mL, 0.090 mmol) and NMO (320 mg, 2.7 mmol). The mixture was allowed to stir at 25° C. for 16 hours. LC showed quite clean reaction at that point. The reaction was diluted with EtOAc (100 mL), washed with aq. NH$_4$Cl and brine, dried over sodium sulfate, and concentrated. The residue was dissolved in methanol and water (20 mL, 1:1). To that solution was added sodium periodate (770 mg, 3.6 mmol in 5 mL of water) at 0° C. The reaction went completion within 2 hours. The crude product was extracted with EtOAc (50 mL×3). The extractions were combined, washed with brine, dried over sodium sulfate, and purified by MPLC to afford tert-Butyl [2-(4-nitrophenyl)ethyl](2-oxoethyl)carbamate. LC-MS (IE, m/z): 209 [M−Boc+1]$^+$.

Step C: Ethyl [(2-{(tert-butoxycarbonyl)[2-(4-nitrophenyl)ethyl]amino}ethyl)amino]acetate To a solution of tert-Butyl [2-(4-nitrophenyl)ethyl](2-oxoethyl)carbamate (0.52 g, 1.7 mmol) in MeOH (10 mL) was added ethyl aminoacetate hydrochloride (0.31 g, 2.2 mmol), sodium cyanoborohydride (1.1 g, 5.1 mmol), and a few drops of acetic acid. The mixture was allowed to stir at 25° C. for 16 hours. LC showed clean reaction. The product was purified by silica gel chromatography (Hexane:EtOAc) to deliver Ethyl [(2-{(tert-butoxycarbonyl) [2-(4-nitrophenyl)ethyl] amino}ethyl)amino]acetate. LC-MS (IE, m/z): 396 [M+1]$^+$.

Step D: 1-[2-(4-nitrophenyl)ethyl]piperazin-2-one

To a solution of Ethyl [(2-{(tert-butoxycarbonyl) [2-(4-nitrophenyl)ethyl]amino}ethyl)amino]acetate (0.50 g, 1.3 mmol) in dioxane (4 mL) was added 4N HCl in dioxane (3.2 mL, 13 mmol). The solution was stirred at 25° C. for 2 hours. LC showed complete removal of the Boc group. The volatiles were removed under vacuum, and the residue was redissolved in toluene and ethanol. To that solution was added triethylamine (0.73 mL, 5.2 mmol). The mixture was heated to reflux for 48 hours. LC at that point showed mostly product. The product was purified by silica gel chromatography (DCM: MeOH) to afford 1-[2-(4-nitrophenyl)ethyl]piperazin-2-one. LC-MS (IE, m/z): 250 [M+1]$^+$.

Intermediate 2

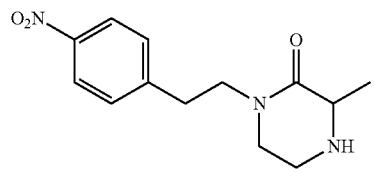 [SMILES: CC1NCCN(CCc2ccc([N+](=O)[O-])cc2)C1=O]

3-Methyl-1-[2-(4-nitrophenyl)ethyl]piperazin-2-one

Step A: 2-{[2-(4-nitrophenyl)ethyl]amino}ethanol

A mixture of 1-(2-Bromoethyl)-4-nitrobenzene (5.0 g, 22 mmol), 2-aminoethanol (1.7 g, 28 mmol), and triethylamine (6.6 mL, 48 mmol) was heated to 60° C. for 16 hours in DMF. LC showed formation of the desired product. DMF was removed under reduced pressure, and the residue was dissolved in EtOAc. The desired product was precipitated out with hexanes. LC-MS (IE, m/z): 211 [M+1]$^+$.

Step B: tert-butyl (2-{(2-hydroxyethyl)[2-(4-nitrophenyl)ethyl]amino}-1-methyl-2-oxoethyl) carbamate A mixture of 2-{[2-(4-nitrophenyl)ethyl]amino}ethanol (1.0 g, 4.8 mmol), 2-[(tert-butoxycarbonyl)amino]propanoic acid (0.9 g, 4.8 mmol), HOBt (0.87 g, 5.7 mmol), Hunig's base (2.5 mL, 14 mmol), and EDC (1.1 g, 5.7 mmol) in DCM was allowed to stir at RT for 16 hours. LC showed formation of the desired product. The product was purified by silica gel chromatography (0-100% EtOAc in hexanes). LC-MS (IE, m/z): 382 [M+1]$^+$.

Step C: 3-Methyl-1-[2-(4-nitrophenyl)ethyl]piperazin-2-one

A solution of tert-butyl (2-{(2-hydroxyethyl)[2-(4-nitrophenyl)ethyl]amino}-1-methyl-2-oxoethyl) carbamate (1.0 g, 2.6 mmol) was first treated with TFA (2.0 mL) to remove the BOC group. LC showed complete reaction within 1 hour. The volatiles were removed under vacuum. The residue was dissolved in NaHCO$_3$, extracted with DCM, dried over Na$_2$SO$_4$, and concentrated to deliver an oil. LC-MS (IE, m/z): 282 [M+1]$^+$. The oil was redissolved in THF (10 mL). To that solution was added triphenylphosphine (820 mg, 3.1 mmol), which was followed by addition of DIAD (0.52 mL, 2.7 mmol). The mixture was allowed to stir for another hour after the addition was over. LC showed formation of the desired product. The reaction was diluted with EtOAc, washed with brine, dried over sodium sulfate, and purified by silica gel chromatography to furnish the title compound. LC-MS (IE, m/z): 264 [M+1]⁺.

Intermediate 3

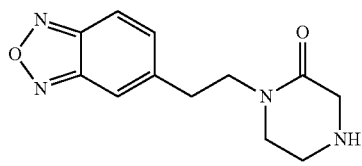 [SMILES: O=C1CNCCN1CCc1ccc2nonc2c1]

1-[2-(2,1,3-Benzoxadiazol-5-yl)ethyl]piperazin-2-one

Step A: 5-Allyl-2,1,3-benzoxadiazole

To a 250 mL flask charged with 5-Bromo-2,1,3-benzoxadiazole (5.0 g, 25 mmol), Palladium Tetrakis (0.87 g, 0.75 mmol), and lithium chloride (2.1 g, 50 mmol) was added Allyl Tri-n-butyltin (10 g, 30 mmol) and toluene (100 mL). The mixture was attached to a reflux condenser, sealed and purged with nitrogen. The reaction was heated to 110° C. for 2 hours. TLC showed good and complete reaction. The reaction was diluted with EtOAc, washed with brine, concentrated and purified by silica gel chromatography.

Step B: 2,1,3-Benzoxadiazol-5-ylacetaldehyde

To a solution of 5-Allyl-2,1,3-benzoxadiazole (4.1 g, 26 mmol) in a solution of MeOH (30 mL), THF (50 mL), and water (20 mL) was added Osium Tetraoxide (6.0 mL 4% aq. solution, 0.77 mmol) and NMO (4.5 g, 38 mmol). The mixture was allowed to stir at 25° C. for 16 hours. TLC showed complete reaction. The reaction was diluted with water (200 mL) and extracted with EtOAc (200 mL×2). The extractions were combined, washed with brine, dried over sodium sulfate, and concentrated. The resulting product was redissolved in water and methanol (50 mL each), and cooled to 0° C. To that solution was added an aqueous solution of sodium periodate (7.2 g, 33 mmol). TLC showed complete reaction within 15 minutes. The reaction was diluted with water (100 mL) and extracted with EtOAc (100 mL×2). The extractions were combined, washed with brine, dried over sodium sulfate, and concentrated to obtain the product which was used in the next step without further purification.

Step C: tert-Butyl allyl[2-(2,1,3-benzoxadiazol-5-yl)ethyl]carbamate

To a solution of 2,1,3-Benzoxadiazol-5-ylacetaldehyde (2.0 g, 12 mmol) and allylamine (0.84 g, 15 mmol) in MeOH (40 mL) was added sodium cyanoborohydride (1.9 g, 31 mmol). The mixture was allowed to stir at RT for 4 hours. LC showed formation of the desired product. Boc-anhydride (5.4 g, 25 mmol) was added to the reaction at that point. The mixture was stirred for another 30 minutes. The crude reaction was diluted with EtOAc, washed with sodium bicarbonate, dried over sodium sulfate, and concentrated. Purification with silica gel flash chromatography to give the title compound. LC-MS (IE, m/z): 204 [M–Boc+1]⁺.

Step D: tert-Butyl [2-(4-nitrophenyl)ethyl](2-oxoethyl)carbamate

Ozone was bubbled into a solution of tert-Butyl allyl[2-(2,1,3-benzoxadiazol-5-yl)ethyl]carbamate (1.1 g, 3.6 mmol) in methanol (100 mL) at −78° C. until it turned blue. Nitrogen was bubbled into the solution to remove excess ozone, which was followed by addition of dimethyl sulfide (2.7 mL, 36 mmol). The reaction was allowed to warm up slowly. LC showed quite clean reaction. The mixture was diluted with EtOAc (300 mL), washed with brine, dried over sodium sulfate, dried and purified by silica gel chromatography to afford the title compound. LC-MS (IE, m/z): 206 [M–Boc+1]⁺.

Step E: Ethyl [(2-{(tert-butoxycarbonyl)[2-(4-nitrophenyl)ethyl]amino}ethyl)amino]acetate To a solution of tert-Butyl [2-(4-nitrophenyl)ethyl](2-oxoethyl)carbamate (0.95 g, 3.1 mmol) in MeOH (20 mL) was added ethyl aminoacetate hydrochloride (480 mg, 3.4 mmol), sodium cyanoborohydride (590 mg, 9.3 mmol) and a drop of acetic acid. The mixture was allowed to stir at RT for 16 hours. LC showed good reaction. The reaction was diluted with EtOAc, washed with aqueous sodium carbonate, dried over sodium sulfate, and purified by silica gel chromatography to furnish the title compound. LC-MS (IE, m/z): 393 [M+1]⁺.

Step F: 1-[2-(2,1,3-Benzoxadiazol-5-yl)ethyl]piperazin-2-one

To a flask charged with ethyl [(2-{(tert-butoxycarbonyl)[2-(4-nitrophenyl)ethyl]amino}ethyl)amino]acetate (500 mg, 1.3 mmol) and a stir bar was added 4N HCl in dioxane (3.2 mL, 13 mmol). When LC indicated the reaction was done, solvents were removed under reduced pressure. The resulting residue was dissolved in ethanol (20 mL), and Hunig's base (1.1 mL, 6.4 mmol) was added to the solution. The reaction was heated to 120° C. for 16 hours. LC showed formation of the desired product, which was purified by silica gel chromatography to provide 1-[2-(2,1,3-Benzoxadiazol-5-yl)ethyl]piperazin-2-one. LC-MS (IE, m/z): 247 [M+1]⁺.

Intermediate 4

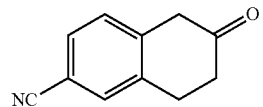

6-Oxo-5,6,7,8-tetrahydronaphthalene-2-carbonitrile

To a 20 mL microwave tube was added 5-bromo-2-tetralone (2.0 g, 8.9 mmol) and Palladium(0) Tetrakis (0.616 g, 0.533 mmol), zinc cyanide (1.0 g, 8.9 mmol), and DMF (8 mL). The tube was sealed, degassed and microwaved at 80° C. for 1.0 hour. TLC showed no starting material left. The mixture was diluted with ethyl acetate, washed with ammonium hydroxide (2M, 2 x), dried with sodium sulfate, filtered and evaporated under reduced pressure. The product was purified by silica gel chromatography with isocratic 30% ethyl acetate-hexane to furnish the title compound. ¹H-NMR (500

MHz, CDCl₃) δ ppm 7.57 (s, 1H), 7.55 (d, J=7.8 Hz, 1H), 7.28 (d, J=7.8 Hz, 1H), 3.67 (s, 2H), 3.14 (t, J=7.0 Hz, 2H), 2.60 (t, J=7.0 Hz, 2H).

Intermediate 5

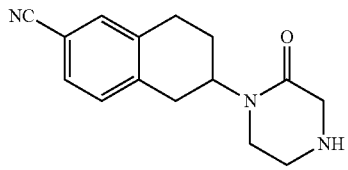 [SMILES: N#Cc1ccc2c(c1)CCC(N1CCNCC1=O)C2]

6-(2-Oxopiperazin-1-yl)-5,6,7,8-tetrahydronaphtha-lene-2-carbonitrile

Step A: Methyl [allyl(tert-butoxycarbonyl)amino]acetate

To a solution of tert-Butyl allylcarbamate (7.2 g, 46 mmol) in THF at −78° C. was added LDA (31 mL, 1.5 M in cyclohexane) by syringe. The reaction was allowed to stir for 10 minutes before methyl bromoacetate (7.0 g, 46 mmol) was added. The reaction was then allowed to warm to RT. The reaction was quenched with water, extracted with EtOAc, dried over magnesium sulfate, and purified by silica gel chromatography (with 15% EtOAc-Hexanes). Removal of solvents provided the title compound. LC-MS (IE, m/z): 130 [M−Boc+1]⁺.

Step B: tert-Butyl 4-(6-cyano-1,2,3,4-tetrahydronaphthalen-2-yl)-3-oxopiperazine-1-carboxylate Ozone was bubbled into a solution of methyl [allyl(tert-butoxycarbonyl)amino]acetate (3.6 g, 16 mmol) in DCM at −78° C. until it turned pale blue. Nitrogen was then bubbled into the solution to remove excess ozone. When the blue color was gone, 6-amino-5,6,7,8-tetrahydronaphthalene-2-carbonitrile (2.7 g, 16 mmol) and sodium triacetoxyborohydride (20 g, 95 mmol) was added to the reaction, and the mixture was allowed to warm to RT. The reaction was diluted with DCM, washed with aqueous sodium bicarbonate and brine, dried over magnesium sulfate, and purified by preparative TLC to afford the title compound. LC-MS (IE, m/z): 256 [M−Boc+1]⁺.

Step C: 6-(2-oxopiperazin-1-yl)-5,6,7,8-tetrahydronaphthalene-2-carbonitrile

To a flask charged with tert-Butyl 4-(6-cyano-1,2,3,4-tetrahydronaphthalen-2-yl)-3-oxopiperazine-1-carboxylate (450 mg, 1.3 mmol) was added 4N HCl in dioxane. The mixture was allowed to stir at RT for 1 hour. LC showed complete reaction. The volatiles were removed under reduced pressure, and the resulting solids were used without further purification. LC-MS (IE, m/z): 256 [M+1]⁺.

Intermediate 6A and 6B

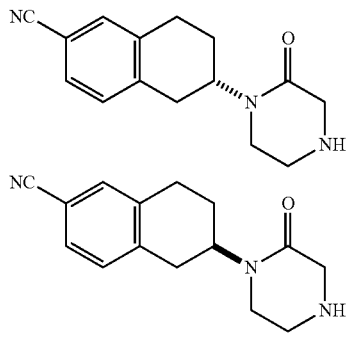

(6S)-6-(2-Oxopiperazin-1-yl)-5,6,7,8-tetrahydronaphthalene-2-carbonitrile (6A) and (6R)-6-(2-oxopiperazin-1-yl)-5,6,7,8-tetrahydronaphthalene-2-carbonitrile (6B)

tert-Butyl 4-(6-cyano-1,2,3,4-tetrahydronaphthalen-2-yl)-3-oxopiperazine-1-carboxylate was resolved on the OD column with 20% Ethanol and Heptane. The faster eluting isomer was tentatively assigned as the (S)-isomer, and the slower isomer as the (R)-isomer. Treating the (S)-isomer with 4N HCl gave rise to (6S)-6-(2-Oxopiperazin-1-yl)-5,6,7,8-tetrahydronaphthalene-2-carbonitrile, and the (R)-isomer gave rise to (6R)-6-(2-oxopiperazin-1-yl)-5,6,7,8-tetrahydronaphthalene-2-carbonitrile.

Intermediate 7

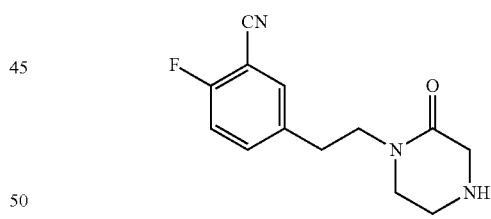

2-Fluoro-5-[2-(2-oxopiperazin-1-yl)ethyl]benzonitrile

Step A: tert-butyl (2-{[2-(3-cyano-4-fluorophenyl)ethyl]amino}ethyl)carbamate

A mixture of 2-fluoro-5-(2-oxoethyl)benzonitrile (1.5 g, 9.2 mmol), tert-butyl(2-aminoethyl)carbamate (1.5 g, 9.2 mmol), NaCNBH₃ (1.2 g, 18.4 mmol) and acetic acid (1.6 g, 27.6 mmol) in methanol (20 mL) was stirred at ambient temperature overnight. The solvents were evaporated, and the residue was basified with saturated NaHCO₃ to pH=7-8, and extracted with EtOAc. The organic layer was separated, dried over anhydrous sodium sulfate and evaporated. The residue was purified with silica gel column chromatography to give tert-Butyl (2-{[2-(3-cyano-4-fluorophenyl)ethyl]amino}ethyl)carbamate.

Step B: tert-Butyl (2-{(chloroacetyl)[2-(3-cyano-4-fluorophenyl)ethyl]amino}ethyl)carbamate A solution of tert-Butyl (2-{[2-(3-cyano-4-fluorophenyl)ethyl]amino}ethyl)carbamate (0.9 g, 3.1 mmol) and TEA (0.4 g, 3.7 mmol) in 10 mL of anhydrous DCM was added chloroacetyl chloride (0.4 g, 3.7 mmol) dropwise at 0° C. The mixture was stirred at 0° C. for 1 h, and then the solvent was evaporated. The residue was partitioned between EtOAc and water. The organic layer was dried and evaporated. The residue was purified with prep-TLC to give tert-Butyl (2-{(chloroacetyl) [2-(3-cyano-4-fluorophenyl)ethyl]amino}ethyl)carbamate.

Step C: 2-Fluoro-5-[2-(2-oxopiperazin-1-yl)ethyl]benzonitrile

A solution of (2-{(chloroacetyl) [2-(3-cyano-4-fluorophenyl)ethyl]amino}ethyl)carbamate (0.12 g, 0.31 mmol) and TFA in 5 mL of DCM was stirred at room temperature for 1 h. The solvent was evaporated. The residue was dissolved in 40 mL of ethanol and $K_2CO_3$ (0.13 g, 0.93 mmol) was added. The resulting mixture was refluxed under $N_2$ overnight, cooled to room temperature, and filtered. The filtrate was evaporated and the residue was purified with preprep-HPLC to give 2-Fluoro-5-[2-(2-oxopiperazin-1-yl)ethyl]benzonitrile. $^1$H-NMR (400 MHz, CDCl$_3$) δ: 7.41~7.44 (m, 2H), 7.07~7.12 (m, 1H), 3.51~3.53 (m, 4H), 3.18~3.22 (m, 2H), 2.99~3.04 (m, 2H), 2.75~2.86 (m, 2H).

Intermediate 8

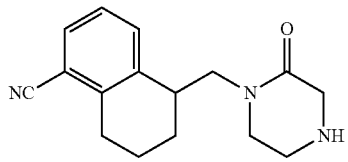 [SMILES: N#Cc1cccc2c1CCCC2CN1CCNCC1=O]

5-[(2-oxopiperazin-1-yl)methyl]-5,6,7,8-tetrahydronaphthalene-1-carbonitrile

Step A: 5-(Methoxymethylene)-5,6,7,8-tetrahydronaphthalene-1-carbonitrile

Sodium bis(trimethylsilyl)amide (2 mL, 4 mmol, 2M in THF) was added to a stirred suspension of (methoxymethyl)triphenylphosphonium chloride (1.47 g, 4.3 mmol) in dry THF (20 mL) at 0° C. for 35 min and a solution of 5-Oxo-5,6,7,8-tetrahydronaphthalene-1-carbonitrile [prepared from 5-bromo-tetralone following the procedure described in PCT publication WO2004/071389A2, Intermediate 41](490 mg, 2.86 mmol) in THF (10 mL) added over 10 min. The mixture was stirred at 0° C. for 2 h and at room temperature for 1 h. Water was added and the mixture was partitioned between EtOAc and brine. The organic layer was dried and concentrated. The crude product was purified via preparative-TLC (PE:EtOAc=10:1) to afford the title compound.

Step B: 5-Formyl-5,6,7,8-tetrahydronaphthalene-1-carbonitrile

A solution of 5-(methoxymethylene)-5,6,7,8-tetrahydronaphthalene-1-carbonitrile (320 mg, 1.61 mmol) in DCM (7 mL) was added BBr$_3$ (1.2 g, 4.8 mmol) dropwise at −78° C. under $N_2$, then the mixture was stirred at this temperature for 3 h. It was poured into ice-saturated NaHCO$_3$ solution, and extracted with DCM. The organic layer was washed with brine and dried over Na$_2$SO$_4$. The solvent was removed in vacuo to give crude title compound, which was used for next step.

Step C: tert-butyl (2-{[(5-cyano-1,2,3,4-tetrahydronaphthalen-1-yl)methyl]amino}ethyl)carbamate A solution of 5-Formyl-5,6,7,8-tetrahydronaphthalene-1-carbonitrile (0.30 g, 1.6 mmol) in MeOH (8 mL) was added (2-amino-ethyl)-carbamic acid tert-butyl ester (0.26 g, 1.6 mol) in MeOH (8 mL), followed by AcOH (0.29 g, 4.8 mmol) and NaBH$_3$CN (0.20 g, 3.2 mmol). The reaction mixture was stirred 2-3 h, and then water (20 mL) and DCM (20 mL) was added. Extracted with DCM, and the organic layers were dried over anhydrous Na$_2$SO$_4$, evaporate to give the crude product, which was purified by column to give the title compound. MS m/z: 330 [M+1]$^+$.

Step D: tert-Butyl (2-{(chloroacetyl)[(5-cyano-1,2,3,4-tetrahydronaphthalen-1-yl)methyl]amino}ethyl)carbamate A solution of tert-Butyl (2-{[(5-cyano-1,2,3,4-tetrahydronaphthalen-1-yl)methyl]amino}ethyl)carbamate (0.20 g, 0.61 mmol) in DCM (5 mL) was added Et$_3$N (74 mg, 7.2 mmol), followed by chloro-acetyl chloride (81 mg, 7.2 mmol). The reaction mixture was stirred overnight. The product was purified by prep-TLC (Pet Ether:EtOAc=1:1) to give the title product. MS m/z: 406 [M+1]$^+$.

Step E: 5-[(2-Oxopiperazin-1-yl)methyl]-5,6,7,8-tetrahydronaphthalene-1-carbonitrile A solution of tert-Butyl (2-{(chloroacetyl)[(5-cyano-1,2,3,4-tetrahydronaphthalen-1-yl)methyl]amino}ethyl)carbamate (120 mg, 0.29 mmol) in DCM (5 mL) was added TFA (0.5 mL) and stirred at ambient temperature for 2 h until TLC indicated the starting material was consumed completely. The solvent was evaporated in vacuum. The residue was dissolved in ethanol (10 mL) and K$_2$CO$_3$ (120 mg, 0.9 mmol) and catalytic NaI was added. The reaction mixture was refluxed overnight, then the salt was removed by filtration. The filtrate was evaporated under vacuum, and then water (10 mL) and DCM (10 mL) was added. The mixture was extracted with DCM (10 mL×3), dried over anhydrous Na$_2$SO$_4$, and evaporated to give the title compound. $^1$H-NMR (400 MHz, CDCl$_3$) δ ppm 7.42 (d, J=7.6 Hz, 1H), 7.33 (d, J=7.6 Hz, 1H), 7.15 (t, J=7.6 Hz, 1H), 3.66-3.72 (m, 1H), 3.54 (s, 2H), 3.21-3.32 (m, 4H), 2.98-3.11 (m, 3H), 2.75-2.85 (m, 1H), 1.78-1.94 (m, 2H), 1.71-1.75 (m, 2H).

Intermediate 9

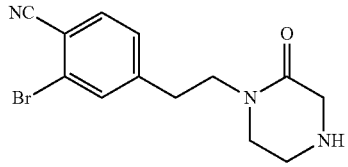 [SMILES: N#Cc1ccc(CCN2CCNCC2=O)cc1Br]

2-Bromo-4-[2-(2-oxopiperazin-1-yl)ethyl]benzonitrile

Step A: 2-(4-Amino-3-bromophenyl)ethanol

A solution of 4-aminophenyl ethanol (34 g, 0.25 mol) and NBS (35 g, 0.20 mol) in DMF (660 mL) was stirred at RT overnight. Then the mixture was diluted with ethyl acetate (2 L), washed with water (300 mL×4), dried over Na$_2$SO$_4$, concentrated in vacuo to give the crude product 2-(4-Amino-3-bromophenyl)ethanol. $^1$H NMR (400 MHz, CDCl$_3$) δ 7.26 (d, J=1.6 Hz, 1H), 6.93 (d, J=1.6 Hz, 1H), 6.70 (s, 1H), 4.44 (br, 1H), 3.76 (t, J=6.4 Hz, 2H), 2.71 (t, J=6.4 Hz, 2H).

Step B: 2-Bromo-4-(2-hydroxyethyl)benzonitrile

A solution of 2-(4-Amino-3-bromophenyl)ethanol (10 g, 0.047 mmol) in water (100 mL) and conc. HCl (32 mL, 0.38 mol) was added a solution of NaNO$_2$ (3.3 g, 0.048 mol) at 0-5° C. Then the mixture was neutralized to pH=6 with aq. NaHCO$_3$. The residue was added to a solution of cuprous cyanide (prepared from 14 g KCN and 14 g CuSO$_4$.5H$_2$O in 120 mL water) at 60° C., and the mixture was stirred at 70° C. for another 2 hours, and then cooled to RT. Filtered through celite, the mixture was extracted with ethyl acetate (200 mL×3), washed with H$_2$O, dried over Na$_2$SO$_4$, concentrated in vacuo to give the title product.

Step C: 2-Bromo-4-(2-oxoethyl)benzonitrile

A solution of 2-Bromo-4-(2-hydroxyethyl)benzonitrile (220 mg, 1.0 mmol) in DCM (15 mL) was added Dess-Martin reagent (1.2 g, 2.8 mmol) and the mixture was stirred at RT for 4 hours. The mixture was washed with water, dried over Na$_2$SO$_4$, and concentrated in vacuo to give the title product. $^1$H NMR (400 MHz, CDCl$_3$) δ 9.77 (t, J=1.6 Hz, 1H), 7.63 (d, J=8.0 Hz, 1H), 7.55 (d, J=1.6 Hz, 1H), 7.25 (dd, J=7.8, 1.6 Hz, 1H), 3.78 (d, J=1.6 Hz, 2H).

Step D: tert-Butyl (2-{[2-(3-bromo-4-cyanophenyl)ethyl]amino}ethyl)carbamate

A mixture of 2-Bromo-4-(2-oxoethyl)benzonitrile (125 mg, 0.54 mmol), N-Boc-Ethyldiamine (257 mg, 1.6 mmol), NaCNBH$_3$ (51 mg, 0.84 mmol) and AcOH (32 mg, 0.53 mmol) was dissolved in DCM and Methanol (6 mL), stirred at RT for 3 hours. Then the mixture was purified by column chromatography to give the title compound.

Step E: tert-Butyl (2-{[2-(3-bromo-4-cyanophenyl)ethyl](chloroacetyl)amino}ethyl)carbamate A solution of tert-Butyl (2-{[2-(3-bromo-4-cyanophenyl)ethyl]amino}ethyl)carbamate (30 mg, 0.081 mmol) and TEA (30 mg, 0.30 mmol) in DCM (1 mL) was added chloroacetyl chloride (10 mg, 0.089 mmol) to the mixture at 0° C. The mixture was stirred at RT for 0.5 hour. Then the residue was diluted with DCM (20 mL) washed with water (5 mL×2) dried over Na$_2$SO$_4$ and concentrated in vacuo to give the desired product. MS m/z: 444 [M+1]$^+$.

Step F: 2-Bromo-4-[2-(2-oxopiperazin-1-yl)ethyl]benzonitrile

A solution of tert-Butyl (2-{[2-(3-bromo-4-cyanophenyl)ethyl](chloroacetyl)amino}ethyl)carbamate (530 mg, 1.2 mmol) in 5 mL of DCM was added 2 mL of TFA and the mixture was stirred at RT for 3 hours, then concentrated in vacuo. The residue was redissolved in ethanol (2 mL) and added K$_2$CO$_3$ (169 mg, 1.22 mmol). The mixture was stirred at reflux for 1.5 hours. Then water (10 ml) was added, and the mixture was extracted with ethyl acetate (5 mL×3), dried over Na$_2$SO$_4$ and concentrated in vacuo to give the title product. $^1$H-NMR (400 MHz, CD$_3$CN) δ 7.68-7.70 (m, 2H), 7.39 (dd, J=1.6, 7.6 Hz, 1H), 3.55 (t, J=5.6 Hz, 2H), 3.27 (s, 2H), 3.18 (t, J=5.6 Hz, 2H), 2.88-2.92 (m, 4H). MS m/z: 308 [M+1]$^+$.

Intermediate 10

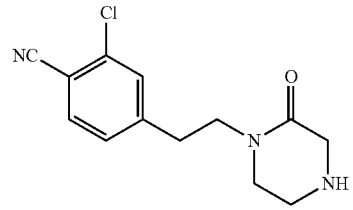

2-Chloro-4-[2-(2-oxopiperazin-1-yl)ethyl]benzonitrile

Step A: 4-Allyl-2-chlorobenzonitrile

A mixture of 4-bromo-2-chlorobenzonitrile (22 mg, 1.0 mmol), allyl tri-n-butylstannane (400 mg, 1.2 mmol), lithium chloride (126 mg, 3.0 mmol), and Pd(PPh$_3$)$_4$, (18 mg, 0.04 mmol) in toluene (10 mL), was refluxed overnight. Then the reaction was quenched with aq. KF (10 mL), extracted with ethyl acetate (10 mL×3), dried over Na$_2$SO$_4$, concentrated in vacuo. The residue was purified by chromatography to give the title product.

Step B: 2-Chloro-4-(2-oxoethyl)benzonitrile

A solution of 4-Allyl-2-chlorobenzonitrile (265 mg, 1.5 mmol) in DCM (2 mL) and methanol (2 mL) was cooled to −78° C. Then O$_3$ was bubbled into for 10 minutes. Then dimethylsulfide (1 mL) was added and the mixture was stirred at RT for 5 hours. The mixture was concentrated in vacuo to give the title product.

Step C: tert-Butyl (2-{[2-(3-chloro-4-cyanophenyl) ethyl]amino}ethyl)carbamate A mixture of 2-chloro-4-(2-oxoethyl)benzonitrile (250 mg, 1.42 mmol), N-Boc-Ethyldiamine (680 mg, 4.26 mmol), NaBH$_3$CN (134 mg, 2.13 mmol), acetic acid (85 mg, 0.71 mmol) was dissolved in DCM (3 mL) and methanol (3 mL), and then the mixture was stirred at RT for 3 hours. Then water (20 mL) was added to the mixture and extracted with DCM (15 mL*3). The organic layers were dried over Na$_2$SO$_4$ and concentrated in vacuo. The residue was purified by chromatography to give the title product. MS m/z: 324 [M+1]$^+$.

Step D: tert-Butyl (2-{(chloroacetyl) [2-(3-chloro-4-cyanophenyl)ethyl]amino}ethyl) carbamate A mixture of tert-Butyl (2-{[2-(3-chloro-4-cyanophenyl) ethyl]amino}ethyl)carbamate (150 mg, 0.463 mmol) and TEA (140 mg, 1.4 mmol) was dissolved in DCM (5 mL), and chloroacetyl chloride (57 mg, 0.51 mmol) was added at 0° C. Then the mixture was stirred at RT for 0.5 hour. Then the mixture was washed with water and dried over Na$_2$SO$_4$, concentrated in vacuo to give the title tert-Butyl (2-{(chloroacetyl)[2-(3-chloro-4-cyanophenyl)ethyl]amino}ethyl) carbamate.

Step E: 2-chloro-4-[2-(2-oxopiperazin-1-yl)ethyl]benzonitrile

A solution of tert-Butyl (2-{(chloroacetyl)[2-(3-chloro-4-cyanophenyl)ethyl]amino}ethyl) carbamate (150 mg, 0.38 mmol) in 5 mL of DCM was added 2 mL of TFA, and then the mixture was stirred at RT for 3 hours. The residue was concentrated in vacuo to give the title product. MS m/z: 300 [M+1]$^+$. The product obtained above (100 mg, 0.33 mmol) was dissolved in ethanol (2 mL) and added K$_2$CO$_3$ (104 mg, 0.75 mmol). The mixture was stirred at reflux for 1.5 hours, then water (15 mL) was added. The mixture was extracted with ethyl acetate (20 mL×3), washed with brine, dried over Na$_2$SO$_4$ and concentrated in vacuo to give the title compound. $^1$H-NMR (CDCl$_3$, 400 MHz) δ 7.55-7.57 (m 1H), 7.33-7.34 (m, 1H), 7.16-7.19 (m, 1H), 3.71-3.74 (m, 2H), 3.51-3.61 (m, 4H), 3.27-3.32 (m, 2H), 2.87-2.90 (m, 2H). MS m/z: 264 [M+1]$^+$.

Intermediate 11

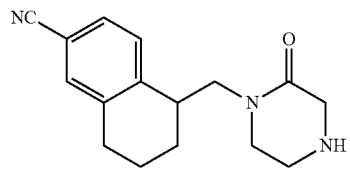 [SMILES: N#Cc1ccc2c(c1)CCCC2CN1CCNCC1=O]

5-[(2-Oxopiperazin-1-yl)methyl]-5,6,7,8-tetrahydronaphthalene-2-carbonitrile

Step A: 5-(Methoxymethylidene)-5,6,7,8-tetrahydronaphthalene-2-carbonitrile

In a 250 mL round bottom flask, (methoxymethyl) (triphenyl)phosphonium chloride (4.0 g, 12 mmol) was dissolved in THF (20 mL). The solution was cooled to −78° C. To above solution was added n-butyl lithium (3.50 mL, 2.50 M in Hexane, 8.8 mmol) dropwise. The mixture was cooled to −78° C. and to it was added 5-oxo-5,6,7,8-tetrahydronaphthalene-2-carbonitrile [prepared from 6-bromo-tetralone following the procedure described in PCT Publication WO2004/071389A2, Intermediate 32](1 g, 5.77 mmol). The reaction was let warm to RT and stirred at r.t for 18 hours. The reaction was then quenched with addition of saturated ammonium chloride (5 mL) and extracted with dichloromethane. The organic phase was washed with brine (5 mL), dried over anhydrous Na$_2$SO$_4$, filtered, concentrated and purified by flash column chromatography (Hexane/EtOAc 0-50%) to obtain the title compound.

Step B: 5-Formyl-5,6,7,8-tetrahydronaphthalene-2-carbonitrile 5-(Methoxymethylidene)-5,6,7,8-tetrahydronaphthalene-2-carbonitrile (800 mg, 4.02 mmol) was dissolved in dichloromethane (6 mL). The solution was cooled to −78° C. To above solution was added tribromoborane (6.0 mL, 1 M, 6.0 mmol) dropwise over the course of 5 min and subsequently stirred for 30 min at −78° C. Saturated sodium bicarbonate was added to the reaction mixture, then the mixture was extracted with DCM (2×20 mL). The organic phase was washed with brine (5 mL), dried over anhydrous Na$_2$SO$_4$, filtered, concentrated and purified by flash column chromatography to provide the title compound.

Step C: tert-Butyl (2-{[(6-cyano-1,2,3,4-tetrahydronaphthalen-1-yl)methyl]amino}ethyl)carbamate To a mixture of N-Boc-ethyldiamine (346 mg, 2.16 mmol), NaBH$_3$CN (136 mg, 2.16 mmol) and HOAc (130 mg, 2.16 mmol) in 10 mL MeOH was added 5-formyl-5,6,7,8-tetrahydronaphthalene-2-carbonitrile (200 mg, 1.08 mmol). The mixture was stirred at RT overnight, and then sat. Na$_2$CO$_3$ (50 mL) was added and stirred for 30 min. The mixture was extracted with EtOAc (3×50 mL) and the combined organic layers were washed with water and brine, dried over anhydrous sodium sulfate and concentrated. The residue was purified by preparative-TLC to give the title compound. MS m/z: 330 [M+1]$^+$.

Step D: tert-Butyl (2-{(chloroacetyl)[(6-cyano-1,2,3,4-tetrahydronaphthalen-1-yl)methyl]amino}ethyl) carbamate A mixture of tert-Butyl (2-{[(6-cyano-1,2,3,4-tetrahydronaphthalen-1-yl)methyl]amino}ethyl)carbamate (110 mg, 0.334 mmol), chloroacetyl chloride (42 mg, 0.37 mmol) and TEA (135 mg, 1.34 mmol) in 20 mL DCM was stirred at RT for 12 hours. The mixture was diluted with 50 mL DCM and then washed with water and brine, dried over anhydrous Na$_2$SO$_4$ and concentrated. The residue was purified via prep-TLC (EtOAc/Petroleum Ether=1:1) to give the title compound. MS m/z: 406 [M+1]$^+$.

Step E: 5-[(2-Oxopiperazin-1-yl)methyl]-5,6,7,8-tetrahydronaphthalene-2-carbonitrile A mixture of tert-Butyl (2-{(chloroacetyl)[(6-cyano-1,2,3,4-tetrahydronaphthalen-1-yl)methyl]amino}ethyl)carbamate (140 mg, 0.35 mmol) in HCl/dioxane (20 mL) was stirred at RT for 12 hours and then concentrated to dryness. To the residue was added 2 mL EtOH and K$_2$CO$_3$ (143 mg, 1.04 mmol). The resulting mixture was heated to reflux for 4 hours before cooled to RT and filtered. The filtrate was concentrate and the residue was partitioned between EtOAc and water. The organic layer was washed with brine, dried over anhydrous Na$_2$SO$_4$ and concentrated to dryness to give the title compound. MS m/z: 270 [M+1]$^+$.

Intermediate 12

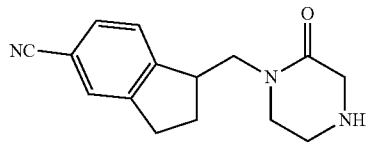 [SMILES: N#Cc1ccc2c(c1)CCC2CN1CCNCC1=O]

1-[(2-oxopiperazin-1-yl)methyl]indane-5-carbonitrile

Step A: 1-(Methoxymethylene)indane-5-carbonitrile

To a mixture of CH$_3$OCH$_2$PPh$_3$I (8.9 g, 26 mmol) in THF (80 mL) was added a solution of NaHMDS in THF (2.0M, 13 mL, 26 mmol)) at 0° C. The mixture was stirred 1 hour at 0° C. Then a solution of 1-Oxoindane-5-carbonitrile (2.0 g, 13 mmol) in THF (10 mL) was added. The mixture was stirred for 2 hours at 0° C. The reaction was quenched with water and extracted with EtOAc. The combined organic phase was washed with brine, dried over anhydrous Na$_2$SO$_4$ and concentrated. The residue was purified by silica gel column chromatograph to give the title compound. MS m/z: 186 [M+1]$^+$.

Step B: 1-Formylindane-5-carbonitrile

To a solution of 1-(Methoxymethylene)indane-5-carbonitrile (1.5 g, 8.1 mmol) in DCM (40 mL) was added BBr$_3$ (6 g, 24 mmol) at −78° C. The mixture was stirred for 3 hours at −78° C. Then water was added. The mixture was extracted with DCM. The combined organic layer was washed with brine, dried over anhydrous Na$_2$SO$_4$ and concentrated to give the crude 1-Formylindane-5-carbonitrile, which was used for next step without further purification. MS m/z: 172 [M+1]$^+$.

Step C: tert-Butyl (2-{[(5-cyano-2,3-dihydro-1H-inden-1-yl)methyl]amino}ethyl)carbamate To a mixture of N-Boc-Ethyldiamine (470 mg, 2.9 mmol), NaBH$_3$CN (360 mg, 5.8 mmol) and HOAc (348 mg, 5.8 mmol) in 20 mL MeOH was added 1-formylindane-5-carbonitrile (500 mg, 2.9 mmol). The mixture was stirred at RT overnight, and then sat. Na$_2$CO$_3$ (50 mL) was added and stirred for 30 min. The mixture was extracted with EtOAc (3×50 mL) and the combined organic layers were washed with water and brine, dried over anhydrous sodium sulfate and concentrated. The residue was purified by prep-TLC to give the title compound. MS m/z: 316 [M+1]$^+$.

Step D: tert-butyl (2-{(chloroacetyl)[(5-cyano-2,3-dihydro-1H-inden-1-yl)methyl]amino}ethyl)carbamate A mixture of tert-Butyl (2-{[(5-cyano-2,3-dihydro-1H-inden-1-yl)methyl]amino}ethyl)carbamate (184 mg, 0.58 mmol), chloro-acetyl chloride (85 mg, 0.76 mmol) and TEA (135 mg, 1.3 mmol) in 20 mL DCM was stirred at RT for 12 hours. The mixture was diluted with 50 mL DCM and then washed with water and brine, dried over anhydrous Na$_2$SO$_4$ and concentrated. The residue was purified via prep-TLC (EA/PE=1:1) to give the title compound. MS m/z: 392 [M+1]$^+$.

Step E: 1-[(2-Oxopiperazin-1-yl)methyl]indane-5-carbonitrile

A mixture of tert-Butyl (2-{(chloroacetyl)[(5-cyano-2,3-dihydro-1H-inden-1-yl)methyl]amino}ethyl)carbamate (125 mg, 0.32 mmol) in HCl/dioxane (20 mL) was stirred at RT for 12 hours and then concentrated to dryness. To the residue was added 2 mL EtOH and K$_2$CO$_3$ (300 mg, 2.0 mmol). The resulting mixture was heated to reflux for 4 hours before cooled to RT and filtered. The filtrate was concentrate and the residue was partitioned between EtOAc and water. The organic layer was washed with brine, dried over anhydrous Na$_2$SO$_4$ and concentrated to dryness to give 1-[(2-Oxopiperazin-1-yl)methyl]indane-5-carbonitrile. MS m/z: 256 [M+1]$^+$.

Intermediate 13

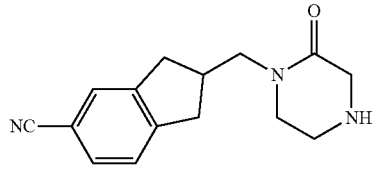 [SMILES: N#Cc1ccc2c(c1)CC(CN1CCNCC1=O)C2]

2-[(2-Oxopiperazin-1-yl)methyl]indane-5-carbonitrile

Step A: (5-Bromo-2,3-dihydro-1H-inden-2-yl)methanol

A solution of Ethyl 5-bromo-2,3-dihydro-1H-indene-2-carboxylate (prepared from 5-Bromo-2,3-dihydro-1H-inden-1-one, following similar procedure of US2005/0075366, compound 148) in 100 mL of anhydrous THF was added LiAlH$_4$ (4.94 g, 130 mmol) portionwise at 0° C. The mixture was warmed slowly to RT and stirred overnight. The reaction mixture was quenched with water (5 mL) and diluted with EtOAc (200 mL) and then filtered. The filtrate was washed with water (300 mL) and brine (300 mL), dried over Na$_2$SO$_4$ and concentrated to dryness to obtain the title compound. $^1$H-NMR (300 MHz, CDCl$_3$) δ 7.33 (s, 1H), 7.24 (d, J=7.9 Hz, 1H), 7.06 (d, J=7.9 Hz, 1H), 3.64 (d, J=6.4 Hz, 2H), 2.96-3.09 (m, 2H), 2.65-2.77 (m, 3H).

Step B: 2-(Hydroxymethyl)-2,3-dihydro-1H-indene-5-carbonitrile

A mixture of (5-Bromo-2,3-dihydro-1H-inden-2-yl)methanol (10 g, 44 mmol), Zn(CN)$_2$ (10.3 g, 88 mmol) and Pd(PPh$_3$)$_4$ (1 g, 0.88 mmol) in 100 mL of DMF was heated at 100-120° C. under N$_2$ atmosphere overnight. Most of the solvent was concentrated and the residue was partitioned between water (100 mL) and EtOAc (100 mL) and separated. The aqueous layer was extracted with EtOAc (50 mL×2). The combined organic layers were washed with brine (200 mL), dried over Na$_2$SO$_4$ and concentrated to dryness. The residue was purified with column chromatography (EtOAc/PE=1:20) to give the title compound. $^1$H-NMR (400 MHz, CDCl$_3$) δ 7.45 (s, 1H), 7.41 (d, J=7.6 Hz, 1H), 7.27 (d, J=8.0 Hz, 1H), 3.64 (d, J=6.6 Hz, 2H), 3.05-3.13 (m, 2H), 2.70-2.84 (m, 3H).

Step C:
2-Formyl-2,3-dihydro-1H-indene-5-carbonitrile

A solution of 2-(Hydroxymethyl)-2,3-dihydro-1H-indene-5-carbonitrile (3.7 g, 21 mmol) in 80 mL of DCM was added Dess-Martin reagent (18 g, 43 mmol) in one portion at 0° C. The mixture was stirred at 0° C. for 1 hour, and then stirred at rt. overnight. The reaction mixture was purified with column chromatography (EtOAc:PE=1:20) to obtain 2-Formyl-2,3-dihydro-1H-indene-5-carbonitrile. $^1$H-NMR (400 MHz, CDCl$_3$) δ 9.77 (d, J=1.2 Hz, 1H), 7.45-7.51 (m, 2H), 7.32 (d, J=7.6 Hz, 1H), 3.32-3.40 (m, 3H), 3.18-3.25 (m, 2H).

Step D: tert-Butyl (2-{[(5-cyano-2,3-dihydro-1H-inden-2-yl)methyl]amino}ethyl)carbamate To a mixture of (2-amino-ethyl)-carbamic acid tert-butyl ester (400 mg, 2.5 mmol), NaBH$_3$CN (315 mg, 5.0 mmol) and HOAc (300 mg, 5.0 mmol) in 30 mL MeOH was added 2-formyl-2,3-dihydro-1H-indene-5-carbonitrile (430 mg, 2.5 mmol). The mixture was stirred at RT overnight, and then sat. Na$_2$CO$_3$ (50 mL) was added and stirred for 30 min. The mixture was extracted with EtOAc (3×50 mL) and the combined organic layers were washed with water and brine, dried over anhydrous sodium sulfate and concentrated. The residue was purified by prep-TLC to give the title compound.

Step E: tert-Butyl (2-{(chloroacetyl)[(5-cyano-2,3-dihydro-1H-inden-2-yl)methyl]amino}ethyl)carbamate A mixture of tert-Butyl (2-{[(5-cyano-2,3-dihydro-1H-inden-2-yl)methyl]amino}ethyl)carbamate (460 mg, 1.5 mmol), chloro-acetyl chloride (180 mg, 1.6 mmol) and TEA (590 mg, 5.8 mmol) in 30 mL DCM was stirred at RT for 12 hours. The mixture was diluted with 50 mL DCM and then washed with water and brine, dried over anhydrous Na$_2$SO$_4$ and concentrated. The residue was purified via prep-TLC (EA/PE=1:1) to give the title compound. MS m/z: 392 [M+1]$^+$.

Step F: 2-[(2-Oxopiperazin-1-yl)methyl]indane-5-carbonitrile

A mixture of tert-Butyl (2-{(chloroacetyl)[(5-cyano-2,3-dihydro-1H-inden-2-yl)methyl]amino}ethyl)carbamate (350 mg, 0.9 mmol) in HCl/dioxane (20 mL) was stirred at RT for 12 hours and then concentrated to dryness. To the residue was added 20 mL EtOH and K$_2$CO$_3$ (500 mg, 3.7 mmol). The resulting mixture was heated to reflux for 4 hrs before cooled to RT and filtered. The filtrate was concentrate and the residue was partitioned between EtOAc and water. The organic layer was washed with brine, dried over anhydrous Na$_2$SO$_4$ and concentrated to dryness to give 2-[(2-Oxopiperazin-1-yl)methyl]indane-5-carbonitrile. MS m/z: 256 [M+1]$^+$.

Intermediate 14

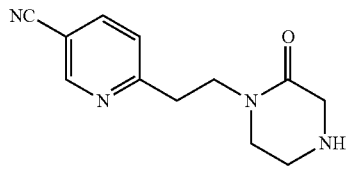 [SMILES: N#Cc1ccc(CCN2CCNCC2=O)nc1]

6-[2-(2-Oxopiperazin-1-yl)ethyl]pyridine-3-carbonitrile

Step A: 6-Chloropyridine-3-carbonitrile

Oxalyl chloride (40 mL) was added dropwise at 0° C. to a suspension of 6-chloropyridine-3-carboxylic acid (18 g, 114 mmol) in 300 mL of DCM with 3 mL of DMF. The mixture was stirred at 25° C. for 2 hours and the clear solution was concentrated to dryness under reduced pressure. The residue was dissolved in 100 mL of anhydrous acetonitrile and then added to 500 mL of diluted aqueous NH$_3$.H$_2$O at 0° C. The mixture was stirred for 30 minutes then extracted with EtOAc twice. The combined EtOAc layers were washed with water and brine, dried over anhydrous Na$_2$SO$_4$ and concentrated. The residue was dissolved in 100 mL of DMF and cooled to 0° C. with ice/water bath. Cyanuric chloride (21.2 g, 114.9 mmol) was added and the mixture was stirred for 2 hours at 0° C. and then poured into ice/water. The resulting solid was collected by filtration, washed with water, dissolved in DCM, dried over anhydrous Na$_2$SO$_4$ and concentrated to afford 6-Chloropyridine-3-carbonitrile.

Step B: 6-(Prop-2-en-1-yl)pyridine-3-carbonitrile

A mixture of 6-chloropyridine-3-carbonitrile (7.0 g, 50 mmol), allyl tri-n-butyltin (18.2 g, 55.0 mmol) and Pd(PPh$_3$)$_2$Cl$_2$ (1 g) in 80 mL DMF was stirred at 90° C. for 3 hours. The mixture was cooled down and diluted with 1 L of EtOAc, washed with water (100 mL×2) and brine (100 mL), then concentrated. The residue was purified by column chromatography (PE:EtOAc=10:1) to afford the title compound.

Step C: 6-(2-Oxoethyl)pyridine-3-carbonitrile

A mixture of 6-(Prop-2-en-1-yl)pyridine-3-carbonitrile (4.8 g, 33 mmol) in 80 mL of DCM and 20 mL of MeOH was cooled to −70° C. Ozone was bubbled through the mixture until the mixture turned blue (about 20 minutes). The excess of ozone was removed by flush with N$_2$ flow until the mixture turned colorless. 5 mL of Me$_2$S was added to the mixture which was then warmed slowly to room temperature and stirred for 2 hours. The solvent was removed under vacuum below 30° C. to afford the title compound which was used without further purification.

Step D: 2-(5-Cyanopyridin-2-yl)ethyl methanesulfonate

NaBH$_4$ (2.5 g, 67 mmol) was added in small portions to a solution of 6-(2-oxoethyl)pyridine-3-carbonitrile (5.0 g, crude) in 80 mL of MeOH at 0° C. The mixture was stirred at room temperature for 30 minutes and poured to 50 mL of water. The mixture was extracted with EtOAc (100 mL×5) and the combined organic layer was condensed. The residue was purified by flash chromatography to afford 6-(2-hydroxyethyl)pyridine-3-carbonitrile. TEA (2.1 g, 21 mmol) was added drop wise to a solution of 6-(2-hydroxyethyl)pyridine-3-carbonitrile (3.0 g, 20 mmol) and MsCl (2.3 g, 20 mmol) in 200 mL of DCM at 0° C. The mixture was stirred at RT for 30 minutes and washed with water and brine, dried over anhydrous Na$_2$SO$_4$ and condensed under vacuum below 30° C. to afford the title compound which was used immediately without further purification.

Step E: tert-Butyl (2-{[2-(5-cyanopyridin-2-yl)ethyl]amino}ethyl)carbamate

A mixture of 2-(5-cyanopyridin-2-yl)ethyl methanesulfonate (4.0 g, crude), tert-butyl(2-aminoethyl)carbamate (4.8 g, 30 mmol) and K$_2$CO$_3$ (3.2 g, 30 mmol) in 40 mL of DMF was stirred overnight at room temperature. The reaction mixture was poured into ice water and extracted with EtOAc (100 mL×3). The combined EtOAc layer was washed with brine and concentrated. The residue was purified by silica gel column (DCM:MeOH=10:1) to afford the title compound.

Step F: 6-[2-(2-Oxopiperazin-1-yl)ethyl]pyridine-3-carbonitrile

TEA (1 eq) was added dropwise to a solution of tert-Butyl (2-{[2-(5-cyanopyridin-2-yl)ethyl]amino}ethyl)carbamate (1 eq) and chloroacetyl chloride (1 eq) in 200 mL of DCM at 0° C. The mixture was stirred at room temperature for 30 minutes and washed with water and brine, dried over anhydrous Na$_2$SO$_4$ and condensed under vacuum. The resulting solid (1.0 g, 2.7 mmol) was added to the mixture of 10 mL TFA and 10 mL of DCM and stirred at RT for 1 hour then concentrated by vacuum. The residue was re-dissolved in CH$_3$CN, K$_2$CO$_3$ was added and the mixture was stirred at RT for 2 hours. The mixture was poured into water and extracted with EtOAc twice. The combined organic layers were concentrated and the residue was purified by flash chromatography (DCM:MeOH=10:1) to afford the title compound $^1$H-NMR (400 MHz, CDCl3) δ ppm 8.74 (d, J=1.6 Hz, 1H), 7.81-7.83 (m, 1H), 7.31 (d, J=8.0 Hz, 1H), 3.71 (t, J=7.2 Hz, 2H), 3.42 (d, J=7.2 Hz, 2H), 3.24 (t, J=5.6 Hz, 2H), 3.09 (t, J=7.2 Hz, 2H), 2.98 (t, J=5.6 Hz, 2H).

Intermediate 15

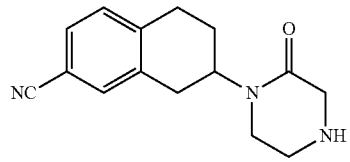 [SMILES: N#Cc1ccc2c(c1)CC(N1CCNCC1=O)CC2]

7-(2-oxopiperazin-1-yl)-5,6,7,8-tetrahydronaphthalene-2-carbonitrile

Step A: 7-(Allylamino)-5,6,7,8-tetrahydronaphthalene-2-carbonitrile

To a solution of 7-oxo-5,6,7,8-tetrahydronaphthalene-2-carbonitrile [prepared from commercially available 7-bromo-2-tetralone following a similar procedure as described in WO2004/071389A2](500 mg, 2.9 mmol) in 20 mL of anhydrous DCM was added 3 drops of HOAc, allylamine (330 mg, 5.8 mmol) and NaBH(OAc)$_3$ (2.46 g, 12 mmol), and the mixture was stirred at RT under nitrogen for 48 hours. DCM was added and the mixture was washed with saturated NaCO$_3$ and brine. The organic layer was dried over anhydrous Na$_2$SO$_4$ and concentrated. The residue was purified by prep-TLC to give 7-(Allylamino)-5,6,7,8-tetrahydronaphthalene-2-carbonitrile.

Step B: tert-Butyl allyl(7-cyano-1,2,3,4-tetrahydronaphthalen-2-yl)carbamate

A solution of 7-(Allylamino)-5,6,7,8-tetrahydronaphthalene-2-carbonitrile (300 mg, 1.4 mmol) in 20 mL of DCM was added TEA (430 mg, 4.26 mmol) and BOC$_2$O (460 mg, 2.1 mmol), and the mixture was stirred at room temperature overnight. The reaction was completed, and DCM was added. Then the mixture was washed with water and brine, and the organic layer was dried over anhydrous Na$_2$SO$_4$ and concentrated to give the title compound. MS m/z: 313 [M+1]$^+$.

Step C: tert-Butyl (7-cyano-1,2,3,4-tetrahydronaphthalen-2-yl)(2-oxoethyl)carbamate A solution of tert-butyl allyl(7-cyano-1,2,3,4-tetrahydronaphthalen-2-yl)carbamate (320 mg, 1.0 mmol) in 1:1 CH$_2$Cl$_2$/MeOH (20 mL) containing pyridine (0.16 mL, 2.0 mmol) was cooled to −78° C., and O$_3$ was passed through until a blue color was present. N$_2$ was then bubbled through to discharge the blue color and Me$_2$S (3 ml) was added. The reaction mixture was allowed to warm and left overnight. The mixture was washed with 1 N HCl and aqueous NaHCO$_3$ and then dried and concentrated to give the title compound. MS m/z: 315 [M+1]$^+$.

Step D: Methyl ({2-[(tert-butoxycarbonyl)(7-cyano-1,2,3,4-tetrahydronaphthalen-2-yl)amino]ethyl}amino)acetate To a solution of tert-Butyl (7-cyano-1,2,3,4-tetrahydronaphthalen-2-yl)(2-oxoethyl)carbamate (260 mg, 0.83 mmol) in 10 mL of anhydrous DCM was added Gly-OMe (150 mg, 1.7 mmol), 2 drops of HOAc and NaBH(OAc)$_3$ (180 mg, 0.83 mmol) and the mixture was stirred at ambient temperature overnight. Then DCM was added, and the mixture was washed with brine. The organic layer was dried over anhydrous Na$_2$SO$_4$ and concentrated. The residue was purified by prep-TLC to the title compound. MS m/z: 388 [M+1]$^+$.

Step E: 7-(2-Oxopiperazin-1-yl)-5,6,7,8-tetrahydronaphthalene-2-carbonitrile

A solution of Methyl ({2-[(tert-butoxycarbonyl)(7-cyano-1,2,3,4-tetrahydronaphthalen-2-yl)amino]ethyl}amino)acetate (145 mg, 0.37 mmol) in 15 mL of anhydrous DCM and 5 mL of TFA was stirred at room temperature for 2-3 hours. The reaction was concentrated. The residue was used directly in the next step. The residue was dissolved in 10 mL of EtOH, and was treated with TEA (5 mL). The mixture was heated to reflux overnight. The reaction was concentrated. The crude

Intermediate 16

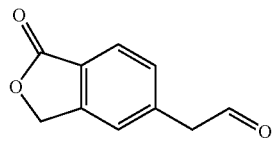 [SMILES: O=CCc1ccc2c(c1)COC2=O]

(1-Oxo-1,3-dihydro-2-benzofuran-5-yl)acetaldehyde

Step A: 5-(1,3-Dioxolan-2-ylmethyl)-2-benzofuran-1(3H)-one

A three-neck 5 L round bottomed flask equipped with a stir bar, firestone valve, thermocouple, condenser and heating mantle was charged with tri-t-butyl phosphonium tetrafluoroborate (500 mg, 1.72 mmol), palladium (II) acetate (250 mg, 1.1 mmol) and 5-bromo-2-benzofuran-1(3H)-one (100 g, 470 mmol). DMF (1.88 L) was added to the flask, and the mixture was degassed three times by alternating vacuum and nitrogen purge. Commercially available bromo(1,3-dioxolan-2-ylmethyl)zinc solution (1.03 L, 516 mmol) was added via canula and the mixture was again degassed three times. The mixture was then heated at 85° C. for 5 hours, checked by HPLC-MS, then stirred at 85° C. for 5 more hours. The mixture was then allowed to return to RT for overnight. 2-MethylTHF (2 L) and brine were added, and the mixture was stirred for 5 min. The layers were separated and the aqueous layer was extracted again with 2-methylTHF. The organic layers were combined, washed three times with brine (4 L each), dried over MgSO4, filtered and concentrated. The crude product was purified by flash chromatography (1.5 kg silica cartridge), eluting with 0-20% ethyl acetate in DCM to afford the title compound. LC-MS (IE, m/z): 221 [M+1]$^+$.

Step B: (1-Oxo-1,3-dihydro-2-benzofuran-5-yl)acetaldehyde 5-(1,3-Dioxolan-2-ylmethyl)-2-benzofuran-1(3H)-one (61 g, 280 mmol) was combined with water (2.2 L) in a 5 L round bottomed flask equipped with a Claisen adapter, thermocouple, stir bar and nitrogen bubbler. Aqueous HCl solution (2M, 1.14 L, 2.29 mol) was added and the resulting mixture was heated at 40° C. for 8 h. Then the mixture was stirred overnight at room temperature. The mixture was extracted three times with 2 L of ethyl acetate. The combined organic layers were concentrated to give (1-oxo-1,3-dihydro-2-benzofuran-5-yl)acetaldehyde. LC-MS (IE, m/z): 177 (M+1)$^+$.

Intermediate 17

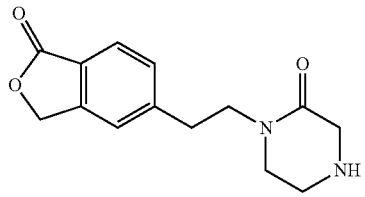 [SMILES: O=C1OCc2cc(CCN3CCNCC3=O)ccc21]

1-[2-(1-Oxo-1,3-dihydro-2-benzofuran-5-yl)ethyl]piperazin-2-one

Step A: tert-Butyl allyl[2-(1-oxo-1,3-dihydro-2-benzofuran-5-yl)ethyl]carbamate

To a solution of (1-oxo-1,3-dihydro-2-benzofuran-5-yl)acetaldehyde (2.1 g, 12 mmol) in MeOH (50 mL) was added allylamine (0.69 mL, 12 mmol), sodium cyanoborohydride (2.3 g, 36 mmol) and a drop of acetic acid. The mixture was allowed to stir at RT for 16 hours. When LC suggested complete reaction, aqueous NaHCO$_3$ solution (20 mL) was added into the reaction, followed by addition of Boc anhydride (2.6 g, 12 mmol). The mixture was allowed to stir for 30 minutes. The reaction was diluted with EtOAc, washed with brine, dried over sodium sulfate, concentrated and purified by silica gel chromatography to furnish the title compound. LC-MS (IE, m/z): 218 [M–Boc+1]$^+$.

Step B: tert-Butyl [2-(1-oxo-1,3-dihydro-2-benzofuran-5-yl)ethyl](2-oxoethyl)carbamate To a solution of tert-butyl allyl[2-(1-oxo-1,3-dihydro-2-benzofuran-5-yl)ethyl]carbamate (0.58 g, 1.8 mmol) in MeOH (50 mL) was bubbled ozone until it turned blue. Nitrogen was bubbled through the solution to remove excess ozone, which was followed by addition of dimethyl sulfide (1.4 mL, 18 mmol). The solution was allowed to warm up slowly. The mixture was diluted with EtOAc, washed with brine, dried over sodium sulfate, and concentrated to afford the product. The crude material was used directly in the next step without further purification.

Step C: Ethyl[(2-{(tert-butoxycarbonyl)[2-(1-oxo-1,3-dihydro-2-benzofuran-5-yl)ethyl]amino}ethyl)amino]acetate To a solution of tert-Butyl [2-(1-oxo-1,3-dihydro-2-benzofuran-5-yl)ethyl](2-oxoethyl)carbamate (580 mg, 1.8 mmol) in MeOH (50 mL) was added ethyl aminoacetate hydrochloride (380 mg, 2.7 mmol), sodium cyanoborohydride (340 mg, 5.4 mmol) and a drop of acetic acid. The reaction was allowed to stir at RT for 16 hours. LC showed the desired product, which was purified by silica gel chromatography. LC-MS (IE, m/z): 407 [M+1]$^+$.

Step D: 1-[2-(1-Oxo-1,3-dihydro-2-benzofuran-5-yl)ethyl]piperazin-2-one

To a flask charged with Ethyl[(2-{(tert-butoxycarbonyl)[2-(1-oxo-1,3-dihydro-2-benzofuran-5-yl)ethyl]amino}ethyl)amino]acetate (280 mg, 0.69 mmol) and a stir bar was added TFA (2 mL). The mixture was allowed to stir at RT for 1 hour. The solvent was removed under vacuum, and the residue was dissolved in EtOH (5 mL). To the solution was added Hunig's base (0.36 mL, 2.1 mmol), and the solution was heated to 150° C. in a microwave tube for 45 minutes. LC showed mostly product, which was purified by silica gel chromatography (MeOH-DCM). The adduct was treated with 4N HCl to remove the BOC group and provide the title compound. LC-MS (IE, m/z): 261 [M+1]$^+$.

(The starting material was adsorbed onto silica gel and purified by MPLC (DCM:MeOH) to afford the title compound. MS m/z: 256 [M+1]$^+$.)

Intermediate 18

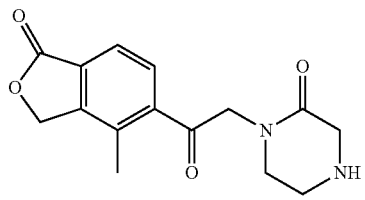 [SMILES: Cc1c(C(=O)CN2CCNCC2=O)ccc2c1COC2=O]

1-[2-(4-Methyl-1-oxo-1,3-dihydro-2-benzofuran-5-yl)-2-oxoethyl]piperazin-2-one

To a THF solution of tert-Butyl 3-oxopiperazine-1-carboxylate (164 mg, 0.82 mmol) was dropped LDA (0.37 ml, 0.74 mmol) at −78° C. After stirring the solution for 15 minutes, a THF solution of 5-(bromoacetyl)-4-methyl-2-benzofuran-1(3H)-one (200 mg, 0.74 mmol) was added into the reaction. TLC showed formation of a new spot right away. LC confirmed the desired alkylation product. The product was purified by MPLC to afford tert-Butyl 4-[2-(4-methyl-1-oxo-1,3-dihydro-2-benzofuran-5-yl)-2-oxoethyl]-3-oxopiperazine-1-carboxylate. LC-MS (IE, m/z): 389 [M+1]$^+$. The resulting solid was further treated with TFA to remove the BOC group. The crude material was dissolved in aqueous sodium bicarbonate, extracted with Chloroform-IPA (3:1) three times, dried over sodium sulfate, and concentrated to furnish the free base of 1-[2-(4-Methyl-1-oxo-1,3-dihydro-2-benzofuran-5-yl)-2-oxoethyl]piperazin-2-one.

Intermediate 19

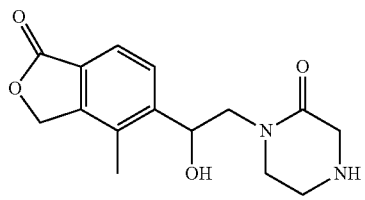 [SMILES: Cc1c(C(O)CN2CCNCC2=O)ccc2c1COC2=O]

1-[2-Hydroxy-2-(4-methyl-1-oxo-1,3-dihydro-2-benzofuran-5-yl)ethyl]piperazin-2-one Step A: tert-Butyl 4-[2-hydroxy-2-(4-methyl-1-oxo-1,3-dihydro-2-benzofuran-5-yl)ethyl]-3-oxopiperazine-1-carboxylate To a solution of tert-Butyl 4-[2-(4-methyl-1-oxo-1,3-dihydro-2-benzofuran-5-yl)-2-oxoethyl]-3-oxopiperazine-1-carboxylate (160 mg, 0.41 mmol) in MeOH (10 ml) was added NaBH$_4$ (31 mg, 0.82 mmol). The reaction was allowed to stir at RT for 2 hours. TLC showed clean conversion. The reaction was quenched by addition of water. The crude material was diluted with EtOAc, washed with water, dried over sodium sulfate, and concentrated to give the title compound. LC-MS (IE, m/z): 391 [M+1]$^+$.

Step B: 1-[2-Hydroxy-2-(4-methyl-1-oxo-1,3-dihydro-2-benzofuran-5-yl)ethyl]piperazin-2-one The product of Step A was treated with TFA to remove the Boc group. The crude material was dissolved in aqueous sodium bicarbonate, extracted with Chloroform-IPA (3:1) three times, dried over sodium sulfate and concentrated to furnish the title compound (free base). LC-MS (IE, m/z): 291 [M+1]$^+$.

Intermediate 20

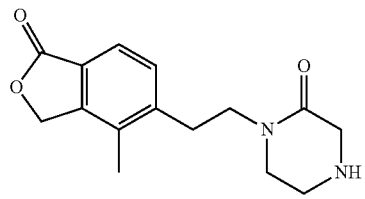 [SMILES: Cc1c(CCN2CCNCC2=O)ccc2c1COC2=O]

1-[2-(4-methyl-1-oxo-1,3-dihydro-2-benzofuran-5-yl)ethyl]piperazin-2-one

A solution of tert-butyl 4-[2-hydroxy-2-(4-methyl-1-oxo-1,3-dihydro-2-benzofuran-5-yl)ethyl]-3-oxopiperazine-1-carboxylate (160 mg, 0.41 mmol) in 20 mL of MeOH was treated with Pd(OH)$_2$ (120 mg, 0.21 mmol) was stirred under 40 psi atmosphere of H$_2$ at 60 C. After 18 hrs the solution was filtered through a pad of celite which was subsequently washed with EtOAc. The filtrate was concentrated and the residue was then redissolved in 2 mL of DCM was treated with 4 mL of 4N HCl in dioxane at room temperature. After 2 hours excess solvent was removed and the residue partitioned between 3 mL of 1N NaOH and 10 mL of 10% IPA/Chloroform. The organic layer was collected, dried over magnesium sulfate, filtered and concentrated to give the title product. The free amine was used without further purification. $^1$H NMR (500 MHz; CDCl$_3$): 7.82 (m, 2H), 5.40 (dd, J=2.3, 8.0 Hz, 1H), 5.27 (s, 1H), 3.74-3.70 (m, 1H), 3.61 (s, 2H), 3.45-3.41 (m, 1H), 3.38-3.34 (m, 1H), 3.26-3.22 (m, 1H), 3.04-3.01 (m, 2H), 2.06 (s, 3H).

Intermediate 21

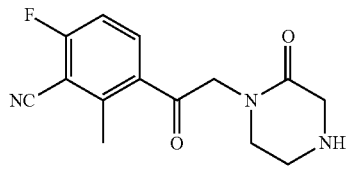

6-Fluoro-2-methyl-3-[{2-oxopiperazin-1-yl)acetyl]benzonitrile

Step A: 2-Fluoro-6-methylbenzonitrile

A 5 L round bottom flask equipped with adapter, thermocouple and stir bar was charged with DMA (2.4 L) and degassed under vacuum and purged with N$_2$ three times. Tetrakis was added to the mixture (35 g, 30.3 mmol) and the mixture was degassed under vacuum and purged with N₂ three times. The reaction was heated to 80° C. for 30 min. 3-Fluoro-2-iodotoluene (230 g, 974 mmol) and zinc cyanide (68.7 g, 585 mmol) were added and the mixture was degassed under vacuum and purged with N₂ three times. The mixture was heated to 80° C. for 16 hrs and allowed to cool to RT. The solution was added to 2.0 L aqueous solution of 1N NH₄OH, which was then extracted three times with 1.5 L EtOAc, washed with 2 L brine, dried over Na₂SO₄, filtered, concentrated and purified by silica chromatography (PE/EA=10:1) to give the title compound.

Step B: 3-Bromo-6-fluoro-2-methylbenzonitrile

NBS (265 g, 1490 mmol) was added portion wise to a stirred, cooled room temperature mixture of 2-Fluoro-6-methylbenzonitrile (191.8 g, 1419 mmol) in TFA (553 mL, 8500 mmol) and then the mixture was heated at reflux for 48 hours. The reaction was poured into 1 L of ice, diluted with 700 mL 30% EtOAc/Hexanes, and agitated. The aqueous layer was cut, and the organic layers were washed with 1N NaOH twice and with water. The organic layers were dried over Na₂SO₄, concentrated, and then stored in a −10° C. freezer overnight. The resulting crystals were filtered and washed with 5% EtOAc/Hexanes to yield the title product.

Step C: 3-(Bromoacetyl)-6-fluoro-2-methylbenzonitrile

Degassed Reactant Sn reagent (200 ml, 591 mmol) was added to a stirred mixture of 3-Bromo-6-fluoro-2-methylbenzonitrile (115 g, 537 mmol) and PdCl₂(PPh₃)₂ (18.86 g, 26.9 mmol) in dioxane (1149 ml) at RT, then degassed with N₂ and the mixture was stirred at 100° C. for 22 hours. The reaction was cooled to 0° C. and THF (575 mL) and water (230 mL) were added followed by NBS (110 g, 618 mmol) added portionwise over 15 min. After 30 minutes, HPLC showed full consumption of the intermediate ketone. The solution was diluted with MTBE (1000 mL) and washed with 0.5% aqueous HBr (3×500 mL), then washed with water. The organic layers were dried over Na₂SO₄, filtered and concentrated. A precipitate generated. The solid was filtered and washed several times with hexanes to give the title product.

Step D: tert-Butyl 4-[2-{3-cyano-4-fluoro-2-methylphenyl}-2-oxoethyl]-3-oxopiperazine-1-carboxylate To a THF solution of tert-butyl 3-oxopiperazine-1-carboxylate (0.080 g, 0.43 mmol) was added Lithium diisopropylamide (0.20 mL, 0.39 mmol) drop wise at −78° C. After stirring for 15 min., a THF solution of 3-(bromoacetyl)-6-fluoro-2-methylbenzonitrile (0.10 g, 0.39 mmol) was added to the reaction mixture slowly. Analysis of the reaction mixture by LC indicated formation of the desired product. To the reaction mixture was sat. NH₄Cl followed by extraction of the aqueous layer with EtOAc. The extractions were combined and washed with brine, dried with Na₂SO₄, and concentrated under reduced pressure to provide a residue which was then subjected for purification by silica gel column chromatography (10% MeOH in DCM) to provide the title product. LC/MS (IE, m/z): [M+1]⁺=376.

Step E: 6-Fluoro-2-methyl-3-[{2-oxopiperazin-1-yl) acetyl]benzonitrile

A flask charged with tert-Butyl 4-[2-{3-cyano-4-fluoro-2-methylphenyl}-2-oxoethyl]-3-oxopiperazine-1-carboxylate (0.030 g, 0.08 mmol) was treated with TFA (2.0 mL) for 20 minutes. Analysis of the reaction mixture by LC indicated that reaction had gone to completion. The solution was concentrated in vacuo and crude was co-evaporated with dichloroethane (3×8 mL) to furnish the title product. LC/MS (IE, m/z): [M+1]⁺=276.

Intermediate 22

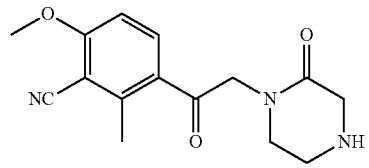 [SMILES: COc1ccc(C(=O)CN2CCNCC2=O)c(C)c1C#N]

6-Methoxy-2-methyl-3-[{2-oxopiperazin-1-yl}acetyl]benzonitrile

Step A: 2-methoxy-6-methylbenzonitrile

To a flask containing a stir bar was added 2-bromo-1-methoxy-3-methylbenzene (7.5 g, 37 mmol), CuCN (6.7 g, 75 mmol) followed by addition of DMF (60 mL); the resulting mixture was then refluxed at 150° C. overnight. When the reaction was complete, as evidenced by LC analysis, the reaction flask was taken out of the oil bath and cooled to room temperature. To the reaction mixture was then poured DCM (20 mL) and a precipitate formed immediately. The solids were filtered, re-dissolved in DCM, absorbed into silica gel and loaded into column with Hexanes:EtOAc (1:1) to afford the title product.

Step B: 3-Bromo-6-methoxy-2-methylbenzonitrile

To a solution of 2-methoxy-6-methylbenzonitrile (3.6 g, 24 mmol) in TFA (25 mL) was added NBS (6.5 g, 36 mmol) and stirred at room temperature for 2 hours. Analysis of the reaction mixture by LC indicated complete bromination of the starting material. The solution was concentrated in vacuo and the resulting crude was dissolved in EtOAc and washed with brine, then dried with Na₂SO₄, filtered and concentrated in vacuo. The crude residue was purified by silica gel column chromatography (Hexanes:EtOAc=1:1) to provide the title product.

Step C: 3-Acetyl-6-methoxy-2-methylbenzonitrile

To a 20 mL microwave tube was added a stir bar, 3-bromo-6-methoxy-2-methylbenzonitrile (4.0 g, 18 mmol), vinyl ethoxy tributyltin (9.5 g, 26 mmol), palladium tetrakis (1.0 g, 0.88 mmol), and anhydrous toluene (15 mL). The tube was capped, degassed and purged with N₂. The reaction mixture was heated to 110° C. for 12 hours. The tube was cooled to room temperature and treated with 4 M HCl (10 mL) and stirred for 1 hour. The crude product was extracted with EtOAc. The extraction was washed with brine, dried with Na₂SO₄, filtered and concentrated in vacuo. The crude residue was purified by silica gel column chromatography (Hexanes:EtOAc=1:1) to afford the title product.

Step D: 3-(Bromoacetyl)-6-methoxy-2-methylbenzonitrile

To a THF solution of 3-acetyl-6-methoxy-2-methylbenzonitrile (1.2 g, 6.3 mmol) was added copper(II) bromide (2.1 g, 9.5 mmol), and a stir bar. The resulting mixture was stirred at room temperature overnight. Analysis of the reaction mixture by LC indicated that reaction had gone to completion. To the reaction mixture was added EtOAc (40 mL) and washed with saturated NH₄OAc, NaCl, dried with Na₂SO₄, filtered and concentrated in vacuo. The crude residue was purified by silica gel column chromatography (Hexanes:EtOAc=1:1) to furnish the title product.

Step E: tert-Butyl 6-methoxy-2-methyl3-[{2-oxopiperazin-1-yl}acetyl]benzonitrile To a THF solution of tert-butyl 3-oxopiperazine-1-carboxylate (0.082 g, 0.41 mmol) was added Lithium diisopropylamide (0.24 mL, 0.39 mmol) dropwise at −78° C. After stirring for 15 minutes, a THF solution of 3-(Bromoacetyl)-6-methoxy-2-methylbenzonitrile (0.10 g, 0.37 mmol) was added to the reaction mixture slowly. Analysis of the reaction mixture by LC indicated formation of the desired product. To the reaction mixture was added saturated NH₄Cl, followed by extraction of the aqueous layer with EtOAc. The combined extracts were washed with brine, dried over Na₂SO₄, and concentrated under reduced pressure to provide a residue which was purified by silica gel column chromatography to provide the title product.

Step F: 6-Methoxy-2-methyl-3-[{2-oxopiperazin-1-yl}acetyl]benzonitrile

To a flask was added tert-Butyl 6-methoxy-2-methyl3-[{2-oxopiperazin-1-yl}acetyl]benzonitrile (0.060 g, 0.15 mmol) followed by addition of TFA (2 mL) and a stir bar; the resulting mixture was stirred for 20 minutes. Analysis of the reaction mixture by LC indicated that reaction had gone to completion. The solution was concentrated in vacuo and the crude was co-evaporated with dichloroethane (3×8 mL) to furnish the title product. LC/MS (IE, m/z): [M+1]⁺=288.

Intermediate 23

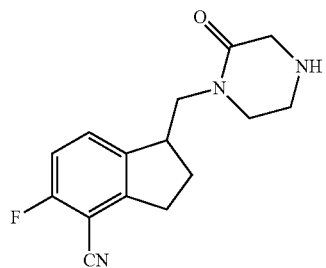 [SMILES: N#Cc1c(F)ccc2c1CCC2CN1CCNCC1=O]

5-Fluoro-1-[(2-oxopiperazin-1-yl)methyl]-2,3-dihydro-1H-indene-4-carbonitrile

Step A: 5-Fluoro-1-oxo-2,3-dihydro-1H-indene-4-carbonitrile

To a flask charged with 4-Bromo-5-fluoro-2,3-dihydro-1H-inden-1-one [made following the procedure described in Intermediate 35, Step B of PCT publication WO 2010/129379) (1.0 g, 4.4 mmol) and a stir bar was added copper(I) cyanide (0.47 g, 5.2 mmol) and DMF (20 ml). The reaction was sealed with a condenser, purged three times with nitrogen, and heated to 150° C. for 16 hours. TLC at that point showed two new spots. The spot right below SM was the title product. LC-MS (IE, m/z): 176 [M+1].

Step B: 5-Fluoro-1-methylidene-2,3-dihydro-1H-indene-4-carbonitrile

To a suspension of methyltriphenylphosphonium bromide (1.6 g, 4.45 mmol) in THF (5 ml) was added n-Butyllithium (1.78 ml, 4.45 mmol) at 0° C. The mixture was stirred for 15 minutes before a THF solution of 4-Bromo-5-fluoro-2,3-dihydro-1H-inden-1-one (260 mg, 1.48 mmol) was added to the reaction. TLC showed formation of the desired product as soon as the addition was done, although not all SM was consumed. The reaction was warmed up to RT slowly, but no significant progress was observed. The reaction was then quenched with NH₄Cl, extracted with EtOAc, washed with brine, dried over Na₂SO₄, and purified by MPLC to obtain the title product.

Step C: 5-Fluoro-1-(piperazin-1-ylmethyl)-2,3-dihydro-1H-indene-4-carbonitrile

To a THF solution of 5-Fluoro-1-methylidene-2,3-dihydro-1H-indene-4-carbonitrile (80 mg, 0.46 mmol) was added BH₃.THF (0.55 ml, 0.55 mmol). The mixture was stirred at 0° C. until there was little SM left. To the reaction was then added hydrogen peroxide (0.101 ml, 1.16 mmol) and NaOH (0.577 ml, 1.16 mmol). After stirring the mixture for an hour, the reaction was diluted with EtOAc, washed with water, dried over Na₂SO₄, and concentrated. The residue was dissolved in DCM, and treated with Dess-Martin reagent (390 mg, 0.92 mmol). When the oxidation was done, the reaction was worked up with Na₂S₂O₃. The crude material was used in the next step without further purification. LC-MS (IE, m/z): 190 [M+1]⁺.

Step D: tert-Butyl [(4-cyano-5-fluoro-2,3-dihydro-1H-inden-1-yl)methyl]prop-2-en-1-ylcarbamate To a flask charged with 5-Fluoro-1-(piperazin-1-ylmethyl)-2,3-dihydro-1H-indene-4-carbonitrile (40 mg, 0.21 mmol) was added allylamine (0.016 mL, 0.21 mmol), sodium cyanoborohydride (13 mg, 0.21 mmol), MeOH (10 mL), and 2 drops of HOAc. The mixture was allowed to stir at RT for 16 hours. LC showed formation of the desired product. The volatiles were removed under vacuum, and the residue was dissolved in DCM and treated with BOC₂O (46 mg, 0.21 mmol). The mixture was adsorbed onto silica gel and purified by MPLC.

Step E: Ethyl N-(2-{(tert-butoxycarbonyl)[(4-cyano-5-fluoro-2,3-dihydro-1H-inden-1-yl)methyl]amino}ethyl)glycinate To a solution of tert-Butyl [(4-cyano-5-fluoro-2,3-dihydro-1H-inden-1-yl)methyl]prop-2-en-1-ylcarbamate (45 mg, 0.14 mmol) in MeOH (5 mL) was bubbled ozone until the solution turned blue. Excess ozone was removed by bubbling nitrogen through. To the reaction was then added DMS (0.50 ml, 6.8 mmol), and it was allowed to warm to RT. The solvent was removed under reduced pressure, and the resulting material was further treated with ethyl aminoacetate hydrochloride (13 mg, 0.090 mmol) and sodium cyanoborohydride (6.0 mg, 0.090 mmol). When LC showed the reaction was done, the reaction was diluted with EtOAc, washed with brine, dried over sodium sulfate, and purified by MPLC to deliver the title product. LC-MS (IE, m/z): 420 [M+1]⁺.

Step F: 5-Fluoro-1-[(2-oxopiperazin-1-yl)methyl]-2,3-dihydro-1H-indene-4-carbonitrile To a flask charged with Ethyl N-(2-{(tert-butoxycarbonyl)[(4-cyano-5-fluoro-2,3-dihydro-1H-inden-1-yl)methyl]amino}ethyl)glycinate (30 mg, 0.072 mmol) was treated with HCl (1.78 ml, 7.2 mmol) to removed the BOC group. The solvent was removed when the deprotection was done. The residue was dissolved in EtOH (10 ml). To this solution was added a few drops of Hunig base. The solution was sealed in a microwave tube and heated to 140° C. for 30 minutes. The resulting title product was purified by MPLC. LC-MS (IE, m/z): 274 [M+1]⁺.

Intermediate 24

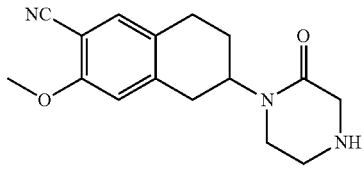 [SMILES: COc1cc2c(cc1C#N)CCC(N1CCNCC1=O)C2]

3-Methoxy-6-(2-oxopiperazin-1-yl)-5,6,7,8-tetrahydronaphthalene-2-carbonitrile

Step A: 6-Bromo-7-methoxy-3,4-dihydronaphthalen-2(1H)-one

To a DCM solution of (4-Bromo-3-methoxyphenyl)acetic acid (900 mg, 3.67 mmol) was added oxalyl chloride (0.64 ml, 7.3 mmol) and a drop of DMF. The solution was allowed to stir at RT for 3 hours, at which point bubbling stopped. The volatiles were removed under vacuum, and the residue was redissolved in DCM. The solution was cooled to 0° C. To this solution was added aluminum trichloride (1.2 g, 9.2 mmol). After stirring the mixture for 15 minutes, ethylene was bubbled into the reaction. The reaction was poured into ice, extracted with DCM, washed with brine, and purified by MPLC. LC-MS (IE, m/z): 255 [M+1]⁺.

Step B: 3-Methoxy-6-oxo-5,6,7,8-tetrahydronaphthalene-2-carbonitrile

To a microwave tube with a stir bar and charged with 6-Bromo-7-methoxy-3,4-dihydronaphthalen-2(1H)-one (25 mg, 0.098 mmol) was added Pd₂(dba)₃ (2.69 mg, 2.94 μmol), S-Phos (2.82 mg, 6.86 μmol), zinc cyanide (17 mg, 0.15 mmol), DMF (1.5 ml) and water (0.015 ml). The tube was sealed and heated to 170° C. for 5 minutes. The reaction was then diluted with EtOAc, washed with NH₄Cl and brine, and the resulting product was purified by MPLC.

Step C: tert-Butyl (6-cyano-7-methoxy-1,2,3,4-tetrahydronaphthalen-2-yl)prop-2-en-1-ylcarbamate To a solution of allylamine (113 mg, 2.0 mmol) and sodium cyanoborohydride (156 mg, 2.5 mmol) in MeOH (20 ml) was added a methanol solution of 3-Methoxy-6-oxo-5,6,7,8-tetrahydronaphthalene-2-carbonitrile (200 mg, 0.99 mmol). The mixture was allowed to stir at RT for 16 hours. The volatiles were then removed under vacuum, and the residue was re-dissolved in DCM. To this solution was added BOC-Anhydride (0.46 ml, 2.0 mmol) and excess triethylamine. The final product was purified by MPLC. LC-MS (IE, m/z): 343 [M+1]⁺.

Step D: Ethyl N-{2-[(tert-butoxycarbonyl)(6-cyano-7-methoxy-1,2,3,4-tetrahydronaphthalen-2-yl)amino]ethyl}glycinate To a solution of tert-Butyl (6-cyano-7-methoxy-1,2,3,4-tetrahydronaphthalen-2-yl)prop-2-en-1-ylcarbamate (150 mg, 0.44 mmol) in MeOH (5 mL) was bubbled ozone until the solution turned blue. Excess ozone was removed by bubbling nitrogen through. To the reaction was then added DMS (0.65 ml, 8.8 mmol), and it was allowed to warm to RT. The solvent was removed under reduced pressure, and the resulting material was further treated with ethyl aminoacetate hydrochloride (65 mg, 0.46 mmol) and sodium triacetoxyborohydride (148 mg, 0.70 mmol). When LC suggested the reaction was done, the reaction was diluted with EtOAc, washed with brine, dried over sodium sulfate, and purified by MPLC to provide the title product. LC-MS (IE, m/z): 432 [M+1]⁺.

Step E: 3-Methoxy-6-(2-oxopiperazin-1-yl)-5,6,7,8-tetrahydronaphthalene-2-carbonitrile To a solution of Ethyl N-{2-[(tert-butoxycarbonyl)(6-cyano-7-methoxy-1,2,3,4-tetrahydronaphthalen-2-yl)amino]ethyl}glycinate (100 mg, 0.232 mmol) in dioxane was added HCl (1.16 ml, 4.6 mmol). The mixture was allowed to stir at RT until there was no SM left. The volatiles were removed, and the residue was dissolved in EtOH (15 ml). To this solution was added Hunig's Base (0.20 ml, 1.16 mmol). The solution was sealed in a microwave tube and heated to 155° C. for 5 hours. The product was then purified by MPLC. LC-MS (IE, m/z): 286 [M+1]⁺.

Intermediate 25

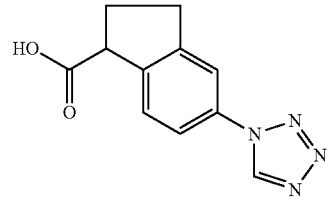 [SMILES: O=C(O)C1CCc2cc(-n3cnnn3)ccc21]

5-(1H-tetrazol-1-yl)indane-1-carboxylic acid

Step A: N-(2,3-dihydro-1H-inden-5-yl)acetamide

A solution of indan-5-amine (43 g, 0.31 mol) and TEA (51.3 mL, 0.370 mol) in 400 mL of anhydrous DCM was added a solution of AcCl (23.6 mL, 0.340 mol) in 100 mL of anhydrous DCM dropwise at 0° C. then and stirred for 0.5 h at RT. After the reaction was completed, 500 mL of DCM was added to the reaction mixture, and the mixture was washed with water, 10% HCl solution, 10% NaHCO₃ and brine. The organic phase was dried over anhydrous Na₂SO₄ and concentrated to give the title compound.

Step B: N-(1-oxo-2,3-dihydro-1H-inden-5-yl)acetamide

A solution of N-(2,3-dihydro-1H-inden-5-yl)acetamide (50 g, 0.29 mol) in 150 mL of acetic acid and 40 mL of acetic anhydride was added dropwise to a solution of chromium trioxide in a mixed solution (30 mL of water and 140 mL of acetic acid) at a temperature of 10° C. (achieved by external cooling). After stirring overnight, the solution was poured into 2 L of ice water with vigorous stirring. The resulting solid was filtered and washed with cooled EtOH to give the title compound.

Step C: N-(1-cyano-2,3-dihydro-1H-inden-5-yl)acetamide

To a stirring ice-cooled mixture of N-(1-cyano-2,3-dihydro-1H-inden-5-yl)acetamide (10.00 g, 52.9 mmol), TosMIC (15.50 g, 80.0 mmol) in 100 mL of anhydrous DME was added a solution of NaOMe (1.84 g of Na in 20 mL of anhydrous of MeOH) dropwise. After the addition was completed, the mixture was stirred overnight at ambient temperature. The reaction mixture was quenched with 4 N HCl at 0° C. and extracted with DCM. The extract was washed with bine, dried over anhydrous $Na_2SO_4$ and concentrated. The residue was purified via silica gel column chromatography to give N-(1-cyano-2,3-dihydro-1H-inden-5-yl)acetamide.

Step D: 5-aminoindane-1-carboxylic acid

A mixture of N-(1-cyano-2,3-dihydro-1H-inden-5-yl)acetamide (19.7 g, 0.105 mol) in 175 mL of concentrated hydrogen chloride was refluxed for two days. The reaction mixture was concentrated under reduce pressure, and the residue was basified with saturated NaOH to ph 4-5. The mixture was extracted with EtOAc and the extract was dried over anhydrous $Na_2SO_4$ and concentrated. The residue was purified via silica gel column chromatography to afford 5-aminoindane-1-carboxylic acid.

Step E: 5-(1H-tetrazol-1-yl)indane-1-carboxylic acid

A solution of 5-aminoindane-1-carboxylic acid (2.95 g, 16.7 mmol), sodium azide (1.20 g, 18.3 mmol) and triethyl orthoformate (7.42 g, 50.1 mmol) in 20 mL of acetic acid was heated to 100° C. for 3 hrs. After the reaction was completed, the mixture was cooled to ambient temperature. The solution was removed under vacuum and the residue was diluted with EtOAc, washed with brine, dried over anhydrous $Na_2SO_4$ and concentrated. The residue was purified via silica gel column chromatography to give the crude product, which was recrystallized from DCM to yield 5-(1H-tetrazol-1-yl)indane-1-carboxylic acid. $^1$H-NMR (400 MHz, DMSO) δ ppm 10.0 (s, 1H), 7.75 (s, 1H), 7.66-7.69 (m, 1H), 7.55 (d, J=8.1 Hz, 1H), 4.02-4.06 (m, 1H), 2.88-3.08 (m, 2H), 2.31 (q, J=8.1 Hz, 2H).

Intermediate 26A and 26B

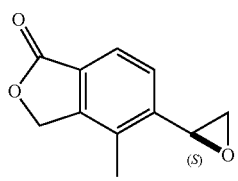

I-26A

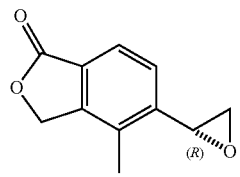

I-26B

I-26A: 4-Methyl-5-[(2R)-oxiran-2-yl]-2-benzofuran-1 (3H)-one and

I-26B: 4-Methyl-5-[(2S)-oxiran-2-yl]-2-benzofuran-1 (3H)-one

Step A: (3-Bromo-2-methylphenyl)methanol

To a solution of 3-bromo-2-methyl benzoic acid (35 g, 163 mmol) in THF (200 mL) was added Borane THF Complex (1.0 M, 212 mL, 212 mmol). The mixture was allowed to stir for 24 h. The reaction was then quenched with water. The THF was removed under reduced pressure. The resulting solid was dissolved in ethyl acetate (500 mL), washed with 1N HCl, sodium carbonate, and brine. The organic layer was dried over sodium sulfate and concentrated to afford (3-bromo-2-methylphenyl)methanol.

Step B: 5-Bromo-4-methyl-2-benzofuran-1(3H)-one

To a flask charged with (3-bromo-2-methylphenyl)methanol (6.0 g, 30 mmol) was added a 1M TFA solution of Thallium Trifluoroacetate (16.2 g, 29.8 mmol). The mixture was stirred at RT overnight. The solvent was removed under vacuum, and the residue was pumped under high vacuum for 30 min to ensure complete removal of TFA. To the residue was then added palladium(II) chloride (529 mg, 2.98 mmol), lithium chloride (2.53 g, 59.7 mmol), magnesium oxide (2.41 g, 59.7 mmol), and MeOH (150 mL). The reaction was flushed with CO twice, and kept under CO at RT. Analysis by LC showed a formation of product within 2 hours. To this solution was added ethyl acetate to precipitate the salts. The solution was filtered through a celite pad, washed with EtOAc, adsorbed onto silica and purified by silica gel chromatography to provide the title compound

Step C: 5-ethenyl-4-methyl-2-benzofuran-1(3H)-one

5-Bromo-4-methyl-2-benzofuran-1(3H)-one (598 mg, 4.47 mmol), potassium vinyl trifluoroborate (507 mg, 2.23 mmol), $PdCl_2(dppf)$-$CH_2Cl_2$ Adduct (182 mg, 0.223 mmol), and TEA (0.622 mL, 4.47 mmol) were added to 10 mL ethanol in a 20 mL microwave tube. The tube was sealed and degassed, then heated to 140° C. for 20 min. Analysis by LC-MS showed product peak. The reaction mixture was diluted with ethyl acetate, washed with brine twice, dried and evaporated to dryness. The crude product was purified by MPLC chromatography using a 120 g Redi-sep column and 0-80% EtOAC/Hexane solvent system to yield the title product. LC-MS: M+1=175 at 2.42 retention time.

Step D: 4-methyl-5-oxiran-2-yl-2-benzofuran-1(3H)-one 5-ethenyl-4-methyl-2-benzofuran-1(3H)-one (1.46 g, 8.38 mmol) was added to DCM (25 mL) at 0° C. then m-CPBA (2.89 g, 16.8 mmol) was added and the mixture was stirred at RT overnight. The reaction mixture was washed once each with saturated aqueous $Na_2S_2O_3$, $NaHCO_3$, and brine. The organic layer was dried over $Na_2SO_4$, filtered, and evaporated to dryness. The crude material was purified by MPLC chromatography through 120 g Redi-sep column eluting with 0-80% EtOAc/hexane solvent system to yield 4-methyl-5-oxiran-2-yl-2-benzofuran-1(3H)-one. $^1$H-NMR (500 MHz, $CDCl_3$): δ ppm 7.77 (d, J=8 Hz, 1H), 7.43 (d, J=8 Hz, 1H), 5.30 (s, 2H), 4.12 (s, 1H), 3.27 (t, J=4 Hz, 1H), 2.735 (dd, J=2.2, 5.5 Hz, 1H), 2.43 (s, 3H).

Step E: I-26A (slower eluting isomer) and I-26B (faster eluting isomer)

Racemic 4-methyl-5-oxiran-2-yl-2-benzofuran-1(3H)-one was resolved on a ChiralPak® AD-H column (5×25 cm) under SFC conditions on a Berger MGIII preparative SFC instrument. The racemate was diluted to 50 mg/ml in 1:1 DCM:MeOH. The separation was accomplished using 10% $EtOH/CO_2$, flow rate 200 ml/min, 100 bar, 25° C. 500 ul Injections were spaced every 2.12 mins. The faster eluting (2R)-epoxide (I-26B) eluted at 5.2 min, and the slower eluting (2S)-epoxide (I-26A) eluted at 5.6 min.

Intermediate 27

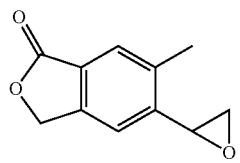

6-Methyl-5-(oxiran-2-yl)-2-benzofuran-1 (3H)-one

Step A: 5-Prop-2-en-1-yl-2-benzofuran-1 (3H)-one

A mixture of 5-bromo-2-benzofuran-1(3H)-one (15.0 g, 70.4 mmol), allyl-tributyl-stannane (25.6 g, 77.5 mmol), LiCl (11.8 g, 282 mmol) and $Pd(PPh_3)_4$ (1.2 g, 1.0 mmol) in 100 mL toluene was heated under $N_2$ at 90-100° C. overnight. After cooling to RT, the mixture was diluted with 250 mL EtOAc and filtered. The filtrate was washed with water and brine, dried over anhydrous $Na_2SO_4$ and concentrated to dryness. The residue was purified via column (DCM/Pet Ether=1:5) to give the title compound.

Step B: 5-(2-hydroxyethyl)-2-benzofuran-1(3H)-one

To a solution of 5-prop-2-en-1-yl-2-benzofuran-1(3H)-one (13.5 g, 45.2 mmol) in 200 mL DCM/MeOH (V/V=1:1) was bubbled $O_3$ at −78° C. for 30 min, and $N_2$ was bubbled for another 15 min at −78° C. Then 20 mL of $Me_2S$ were added, and the mixture was stirred at RT overnight before concentrating to dryness. The residue was dissolved in MeOH (100 mL) and then cooled to 0° C. $NaBH_4$ (5.90 g, 155 mmol) was added in portions. The resulting mixture was stirred at 0° C. for 1 h, then quenched with citric acid (aq.) and extracted three times with EtOAc. The combined organic layers were washed with $NaHCO_3$ (aq.) and brine, dried over anhydrous $Na_2SO_4$ and concentrated to dryness. The residue was purified via column chromatography (EtOAc/Pet Ether=1:5) to give 5-(2-hydroxyethyl)-2-benzofuran-1(3H)-one.

Step C: 5-(2-hydroxyethyl)-6-iodo-2-benzofuran-1 (3H)-one

To a cooled (0° C.) solution of 5-(2-hydroxyethyl)-2-benzofuran-1(3H)-one (9.00 g, 50.6 mmol) in 100 mL of TfOH was added NIS (12.5 g, 55.6 mmol), then the mixture was stirred at 0° C. for 2 hrs and then poured into ice-water (500 mL). The solution was extracted three times with 500 mL of EtOAc and the combined organic layers were washed with saturated $NaHCO_3$ and brine, dried over anhydrous sodium sulfate, filtered and concentrated. The residue was purified by column chromatography (EtOAc/Pet Ether=1:5) to give the title compound.

Step D: 5-(2-hydroxyethyl)-6-methyl-2-benzofuran-1(3H)-one

To a flask charged with 5-(2-hydroxyethyl)-6-iodo-2-benzofuran-1(3H)-one (6.00 g, 19.7 mmol) and a stir bar was added $Pd_2(dba)_3$ (452 mg, 0.493 mmol), $PPh_3$ (1 g, 4 mmol) and NMP (50 mL). The mixture was purged with $N_2$ and heated to 50° C. for 10 min, followed by addition of CuI (375 mg, 1.97 mmol). After the mixture was heated for another 10 min, $Sn(CH_3)_4$ (5.30 g, 29.6 mmol) was added into the reaction, and it was heated to 120° C. for 2 h. After cooling to RT, the mixture was diluted with saturated $NH_4Cl$ (200 mL) and extracted with EtOAc (3×200 mL). The combined organic layers were washed with water and brine, dried over anhydrous sodium sulfate, filtered and concentrated. The residue was purified by prep-HPLC to give the title compound.

Step E: 2-(6-methyl-1-oxo-1,3-dihydro-2-benzofuran-5-yl)ethyl methanesulfonate

To a solution of 5-(2-hydroxyethyl)-6-methyl-2-benzofuran-1(3H)-one (1.20 g, 6.25 mmol) and TEA (2.5 g, 25 mmol) in DCM (100 mL) was added MsCl (1.40 g, 12.5 mmol) at 0° C. The mixture was stirred at ambient temperature overnight, then was washed with water and brine. The organic layer was dried and concentrated to dryness to obtain the title compound.

Step F: 5-ethenyl-6-methyl-2-benzofuran-1(3H)-one

To a mixture of 2-(6-methyl-1-oxo-1,3-dihydro-2-benzofuran-5-yl)ethyl methanesulfonate (2.00 g, 7.41 mmol) and TEA (5 mL) in DCM (50 mL) was added DBU (5 mL) slowly at 0° C. The mixture was stirred at r.t. overnight, and then was diluted with 50 mL of DCM, washed with 2 N HCl three times and brine. The organic layer was dried and concentrated to dryness. The residue was purified by prep-TLC to give 5-ethenyl-6-methyl-2-benzofuran-1(3H)-one.

Step G: 6-methyl-5-oxiran-2-yl-2-benzofuran-1(3H)-one

To a solution of 5-ethenyl-6-methyl-2-benzofuran-1(3H)-one (1.00 g, 5.75 mmol) in 50 mL of DCM was slowly added m-CPBA (3.50 g, 17.4 mmol) in 50 mL of DCM at 0° C. The mixture was warmed to room temperature, and stirred for 2 days. The mixture was washed with aqueous $Na_2SO_3$ until KI indicator paper didn't change color. The organic layer was washed with brine and then concentrated. The residue was purified via silica column to give product 6-methyl-5-oxiran-2-yl-2-benzofuran-1(3H)-one. LC/MS (IE, m/z): [M+1]⁺=191.

Intermediate 28

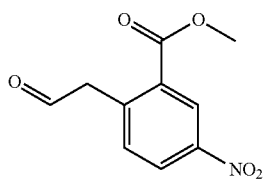 [SMILES: COC(=O)c1cc([N+](=O)[O-])ccc1CC=O]

Methyl 5-nitro-2-(2-oxoethyl)benzoate

Step A: Methyl 5-nitro-2-(prop-2-en-1-yl)benzoate

A mixture of Methyl 2-bromo-5-nitrobenzoate (0.60 g, 2.3 mmol), allyl tri-n-butyltin (0.92 g, 2.8 mmol), lithium chloride (0.29 g, 6.9 mmol), and palladium tetrakis (0.13 g, 0.12 mmol) was heated to reflux for 16 hours in toluene. TLC showed formation of the desired product. The reaction was diluted with EtOAc, washed with brine, and separated. The organic layer was dried over sodium sulfate, filtered and concentrated under reduced pressure. The residue was purified by silica gel chromatography to obtain the title compound.

Step B: Methyl 5-nitro-2-(2-oxoethyl)benzoate

To a solution of Methyl 5-nitro-2-(prop-2-en-1-yl)benzoate (0.20 g, 0.90 mmol) in water (2 mL) and THF (5 mL) was added osmium tetroxide (0.57 mL 2.5% solution, 0.045 mmol) and NMO (0.16 g, 1.4 mmol). The mixture was allowed to stir at RT for 16 hours and monitored by TLC. The reaction was diluted with EtOAc, washed with NH₄Cl and brine, and concentrated. The residue was redissolved in MeOH and water. After cooling the solution to 0° C., an aqueous solution of sodium periodate (0.39 g, 1.8 mmol) was dropped into the reaction and allowed to stir for 2 hours. The reaction was diluted with water, extracted with EtOAc, dried over sodium sulfate, and concentrated. The crude residue was purified by silica gel chromatography to provide Methyl 5-nitro-2-(2-oxoethyl)benzoate. ¹H-NMR (400 MHz, CDCl₃) δ ppm 9.48 (S, 1H), 8.97 (s, 1H), 8.39 (d, J=8.0 Hz, 1H), 7.46 (d, J=8.0 Hz, 1H), 4.31 (s, 2H), 3.98 (s, 3H).

Intermediate 29

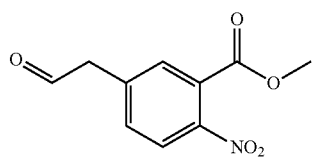 [SMILES: COC(=O)c1cc(CC=O)ccc1[N+](=O)[O-]]

Methyl 2-nitro-5-(2-oxoethyl)benzoate

The title compound was prepared from Methyl 5-chloro-2-nitrobenzoate using essentially the same procedure as described for Intermediate 40. ¹H-NMR (400 MHz, CDCl₃) δ ppm 9.84 (S, 1H), 7.98 (d, J=8.0 Hz, 1H), 7.61 (s, 1H), 7.50 (d, J=8.0 Hz, 1H), 3.98 (s, 3H), 3.94 (s, 2H).

Intermediate 30

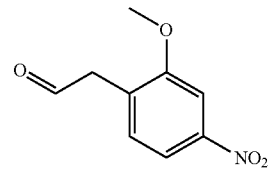

(2-Methoxy-4-nitrophenyl)acetaldehyde

The title compound was prepared from 1-Bromo-2-methoxy-4-nitrobenzene using essentially the same procedure as described for Intermediate 40. ¹H-NMR (500 MHz, CDCl₃) δ ppm 9.78 (S, 1H), 7.89 (d, J=8.0 Hz, 1H), 7.78 (s, 1H), 7.35 (d, J=8.0 Hz, 1H), 3.98 (s, 3H), 3.81 (s, 2H).

Intermediate 31

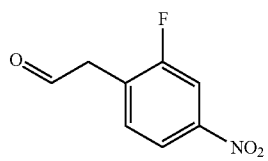

(2-Fluoro-4-nitrophenyl)acetaldehyde

The title compound was prepared from 1-Bromo-2-fluoro-4- using essentially the same procedure as described for Intermediate 40. ¹H-NMR (500 MHz, CDCl₃) δ ppm 9.86 (S, 1H), 8.10 (m, 1H), 8.01 (m, 1H), 7.43 (m, 1H), 3.97 (s, 2H).

Intermediate 32

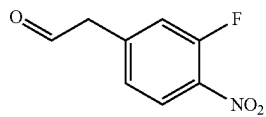 [SMILES: O=CCc1ccc([N+](=O)[O-])c(F)c1]

3-Fluoro-4-nitrophenylacetaldehyde

The title compound was prepared from 4-Bromo-2-fluoro-1-nitrobenzene using essentially the same procedure as described for Intermediate 40. ¹H-NMR (500 MHz, CD₃Cl) δ 9.84 (s, 1H), 8.09-8.08 (m, 1H), 7.21-7.15 (m, 2H), 3.87 (s, 2H)

Intermediate 33

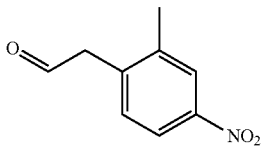

2-Methyl-4-nitrophenylacetaldehyde

The title compound was prepared from 1-Bromo-2-methyl-4-nitrobenzene using essentially the same procedure as described for Intermediate 40. ¹H-NMR (500 MHz, CD₃Cl) δ 9.76 (s, 1H), 8.074 (s, 1H), 7.32-7.30 (m, 2H), 3.86 (s, 2H), 2.61 (s, 3H)

Intermediate 34

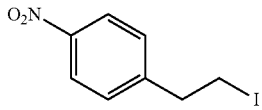 [SMILES: O=[N+]([O-])c1ccc(CCI)cc1]

1-(2-Iodoethyl)-4-nitrobenzene

To a 0° C. solution of triphenylphosphine (1.9 g, 7.2 mmol) and imidazole (489 mg, 7.18 mmol) in DCM (20 ml) was added iodine (1822 mg, 7.18 mmol) to form a solution. Small portions of 2-(4-nitrophenyl)ethanol (1.0 g, 6.0 mmol) was added to the suspension. TLC showed conversion to the desired product quickly. Hexane was added to the reaction to precipitate side products which were filtered off. The filtrate was concentrated in vacuo to obtain crude 1-(2-iodoethyl)-4-nitrobenzene, which was purified by silica gel flash chromatography using Hexane and EtOAc system. ¹H-NMR (500 MHz, CD₃Cl) δ 8.22 (d, J=8.5 Hz, 2H), 7.40 (d, J=8.5 Hz, 2H), 3.41 (t, J=7.0 Hz, 2H), 3.32 (t, J=7.0 Hz, 2H).

Intermediate 35

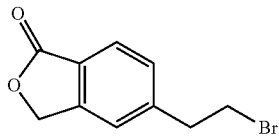 [SMILES: O=C1OCc2cc(CCBr)ccc21]

5-(2-Bromoethyl)-2-benzofuran-1(3H)-one

Step A: 5-Allyl-2-benzofuran-1(3H)-one

A 4-neck, 22-L, round bottom flask equipped with a mechanical stirrer, thermocouple, nitrogen bubbler, and condenser was charged with 5-bromophthalide (650 g, 3.0 mol), allyltri-n-butyltin (1200 g, 3.6 mol), palladium tetrakis triphenylphosphine (100 g, 0.089 mol), lithium chloride (250 g, 5.9 mol) and toluene (8.8 L). The mixture was evacuated and flushed with nitrogen 3 times and then was stirred at 100° C. for 4 hours. After slowly cooling to ambient temperature, the mixture was filtered and concentrated. The resulting solid was purified by silica gel column chromatography (heptane: ethyl acetate, 0→40%) to provide 5-allyl-2-benzofuran-1 (3H)-one.

Step B: 5-(2-Hydroxyethyl)-2-benzofuran-1(3H)-one 5-allyl-2-benzofuran-1(3H)-one (1.53 g, 8.78 mmol) was dissolved in methanol (30 mL). THF was added to solubilize the starting material. The resulting mixture was cooled in a dry ice acetone bath (−78° C.) and ozone was bubbled into the reaction until the color of the mixture changed to orange. Nitrogen was bubbled into the reaction for one minute to remove the excess ozone. Sodium borohydride (0.65 g, 2.9 mmol) was added at −78° C., and the reaction mixture was allowed to warm to ambient temperature. The reaction mixture was concentrated part way and then taken up in ethyl acetate and water. The layers were separated and the organic layer was washed with brine, dried over magnesium sulfate, filtered, and concentrated to provide the title compound.

Step C: 5-(2-Bromoethyl)-2-benzofuran-1 (3H)-one

To a solution of 5-(2-hydroxyethyl)-2-benzofuran-1(3H)-one (1.2 g, 6.8 mmol) in DCM at 0° C. was added carbon tetrabromide (2.3 g, 6.8 mmol), triphenylphosphine (1.8 g, 6.8 mmol), and imidazole (0.46 g, 6.8 mmol). The mixture was allowed to stir at 0° C. for 5 minutes, and then allowed to warm to RT and stir for 1.5 hours. The crude was concentrated and purified by silica gel chromatography (43% EtOAc with Hexanes) to obtain 5-(2-Bromoethyl)-2-benzofuran-1(3H)-one. LC-MS (IE, m/z): 241/243 (M+1)⁺.

Intermediate 36

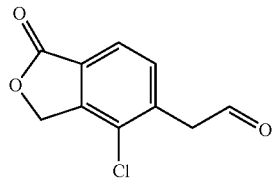 [SMILES: O=CCc1ccc2c(c1Cl)COC2=O]

(4-chloro-1-oxo-1,3-dihydro-2-benzofuran-5-yl) acetaldehyde

Step A: methyl 3-amino-2-chlorobenzoate

To a solution of methyl 2-chloro-3-nitrobenzoate (2.1 g, 9.7 mmol) in methanol (100 mL) and THF (20 mL) was added zinc powder (1.9 g, 29 mmol), ammonium formate (3.1 g, 49 mmol), and a few drops of acetic acid. The mixture was allowed to stir at RT for 18 hours. Most of the volatiles were removed under reduced pressure. The residue was redissolved in EtOAc (200 mL), washed with brine, concentrated and purified by MPLC to provide methyl 3-amino-2-chlorobenzoate.

Step B: methyl 3-bromo-2-chlorobenzoate

To a solution of methyl 3-amino-2-chlorobenzoate (2.0 g, 11 mmol) in 48% HBr (10 mL) and water (20 mL) was added an aqueous solution of sodium nitrite (0.89 g, 13 mmol) at 0° C. The mixture was allowed to stir at 0° C. for 30 minutes before it was added into a suspension of copper(I) bromide (2.3 g, 16 mmol) in water (10 mL) and 48% HBr (5 mL) at 0° C. The reaction was allowed to warm to RT slowly, and then heated to 60° C. for 5 minutes. The product was extracted with DCM (100 mL X 2). The extractions were combined, dried over sodium sulfate, adsorbed onto silica gel, and purified by MPLC to provide methyl 3-bromo-2-chlorobenzoate. LC-MS (IE, m/z): 251 [M+1]$^+$

Step C: (3-bromo-2-chlorophenyl)methanol

To a solution of methyl 3-bromo-2-chlorobenzoate (1.9 g, 7.6 mmol) in THF (30 mL) was added Super Hydride (23 mL, 23 mmol) at 0° C. The reaction was allowed to stir for 16 hours. The reaction was diluted with EtOAc, washed with brine, dried over sodium sulfate, and purified by MPLC to provide (3-bromo-2-chlorophenyl)methanol. LC-MS (IE, m/z): 205 [M-17]$^+$;

Step D: 5-bromo-4-chloro-2-benzofuran-1(3H)-one

To a flask charged with (3-bromo-2-chlorophenyl)methanol (1.1 g, 4.8 mmol) and a stir bar was added thallium trifluoroacetate (2.9 g, 5.3 mmol) and TFA (6 mL). The mixture was allowed to stir at RT for 16 hours. The volatiles were removed under reduced pressure. The residue was pumped under high vacuum for 15 minutes before palladium (II) chloride (0.085 g, 0.48 mmol), magnesium oxide (0.39 g, 9.6 mmol), lithium chloride (0.20 g, 4.8 mmol), and ethanol (30 mL) were added. The mixture was stirred under an atmosphere of carbon mono-oxide until the reaction turned black. The reaction was diluted with DCM. The suspension was filtered through a pad of celite to remove the solids. The filtrate was adsorbed onto silica gel, and purified by MPLC to afford the title compound.

Step E: 5-allyl-4-chloro-2-benzofuran-1(3H)-one

To a flask charged with 5-bromo-4-chloro-2-benzofuran-1(3H)-one (190 mg, 0.77 mmol) and a stir bar was added allyl tri-n-butyltin (0.36 mL, 1.2 mmol), PdCl$_2$(dppf)-DCM complex, lithium chloride (0.098 mg, 2.3 mmol), and toluene (5 mL). The flask was fitted with a condensor, purged three times with nitrogen, and heated to reflux for 6 hours. When LC showed complete reaction, the crude material was purified by MPLC to provide 5-allyl-4-chloro-2-benzofuran-1(3H)-one. LC-MS (IE, m/z): 209 [M+1]$^+$;

Step E: (4-chloro-1-oxo-1,3-dihydro-2-benzofuran-5-yl)acetaldehyde

Ozone was bubbled through a solution of 5-allyl-4-chloro-2-benzofuran-1(3H)-one (80 mg, 0.38 mmol) in MeOH at −78° C. until it turned light blue. After excess ozone was removed by bubbling nitrogen through the solution, dimethyl sulfide (0.57 mL, 7.7 mmol) was added into the reaction. The solution was allowed to warm to RT. The crude material was purified by MPLC to provide (4-chloro-1-oxo-1,3-dihydro-2-benzofuran-5-yl)acetaldehyde. LC-MS (IE, m/z): 211 [M+1]$^+$.

Intermediate 37

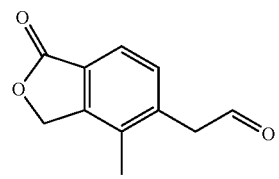

(4-Methyl-1-oxo-1,3-dihydro-2-benzofuran-5-yl)acetaldehyde

Step A: 4-methyl-5-prop-2-en-1-yl-2-benzofuran-1(3H)-one

To a flask charged with 5-Bromo-4-methyl-2-benzofuran-1(3H)-one (320 mg, 1.41 mmol) and a stir bar was added Allyl tri-n-butyltin (0.655 ml, 2.11 mmol), Pd(PPh$_3$)$_4$ (244 mg, 0.211 mmol), lithium chloride (179 mg, 4.23 mmol), and toluene (15 mL). The reaction was purged with nitrogen 2 times then was heated at reflux for 4 hours. The product was purified by silica gel chromatography to give the title compound.

Step B: (4-methyl-1-oxo-1,3-dihydro-2-benzofuran-5-yl)acetaldehyde

A solution of the above olefin (220 mg, 1.2 mmol) in MeOH (20 mL) was cooled to −78° C. To this solution was bubbled ozone until the reaction turned blue. Nitrogen was bubbled through the reaction to drive off excess ozone, followed by addition of DMS (0.870 mL, 11.7 mmol). The reaction was allowed to warm up to RT. The crude product was purified by flash chromatography to afford (4-methyl-1-oxo-1,3-dihydro-2-benzofuran-5-yl)acetaldehyde. $^1$H-NMR (500 MHz, CDCl$_3$) δ ppm 9.78 (s, 1H), 7.75 (d, J=7.5 Hz, 1H), 7.34 (d, J=7.5 Hz, 1H), 5.27 (s, 2H), 3.90 (s, 2H), 2.23 (s, 3H).

Intermediate 38

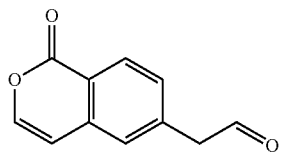 [SMILES: O=CCc1ccc2c(=O)occc2c1]

(1-Oxo-1H-isochromen-6-yl)acetaldehyde

Step A: 6-Bromo-3,4-dihydro-1H-isochromen-1-one

LDA (12 ml, 17 mmol) was dissolved in THF (50 ml) at −78° C. then 4-Bromo-2-methylbenzoic acid (1.0 g, 4.6 mmol) in 10 ml THF was added. The mixture was stirred for 10 minutes then paraformaldehyde (0.56 g, 18.6 mmol) was added. The reaction was stirred at RT for 4 hours. When LC-MS showed the product M+1=229, the reaction was poured into 1N HCl and extracted with ether. The organic layer was washed with brine, dried and evaporated to dryness. The residue was flashed through an Analogix 115 g column and eluted with 0-100% ethyl acetate/hexane to yield 6-bromo-3,4-dihydro-1H-isochromen-1-one.

Step B:
4,6-Dibromo-3,4-dihydro-1H-isochromen-1-one

6-Bromo-3,4-dihydro-1H-isochromen-1-one (3.0 g, 13 mmol) was dissolved in $CCl_4$ (150 ml) then added N-bromosuccinimide (2.4 g, 13 mmol) followed by benzoyl peroxide (0.096 g, 0.40 mmol) and refluxed for 3 hours. Filtered and concentrated then chromatographed through a 120 g ISCO Redi-sep. column and eluted with 0-25% EtOAc/Hexane to yield the title compound. LC-MS (IE, m/z): 306.9 $[M+1]^+$.

Step C: 6-Bromo-1H-isochromen-1-one 4,6-Dibromo-3,4-dihydro-1H-isochromen-1-one (1.8 g, 5.8 mmol) was dissolved in DCM (15 ml) then added TEA (20 mL, 143 mmol) and stirred at room temperature for 72 hours. The mixture was concentrated then took up the residue with DCM and washed with 1N HCl. Repeated the wash with brine then dried over $Na_2SO_4$ and evaporated to dryness. The residue was purified by MPLC with 0-100% EtOAc/hexane to yield 6-Bromo-1H-isochromen-1-one. LC-MS (IE, m/z): 227 $[M+2]^+$.

Step D:
6-(1,3-Dioxolan-2ylmethyl)-1H-isochromen-1-one

A mixture of 6-Bromo-1H-isochromen-1-one (980 mg, 4.4 mmol), tributyl phosphonium tetrafluoroborate (25 mg, 0.087 mmol), palladium (II) acetate (9.8 mg, 0.044 mmol) was suspended in DMF (10 ml) then added bromo(1,3-dioxolan-2-ylmethyl)zinc (9.58 ml, 4.79 mmol) and purged with nitrogen. The reaction was heated to 85° C. for 10 hours and then stirred at RT overnight. Methyl tetrahydrofuran was added and the mixture was washed with brine. The organic layer was dried over $MgSO_4$, filtered and evaporated to dryness. The residue was purified thru a 80 g ISCO Redi-sep column and eluted with 0-100% EtOAc/hexane to yield the title compound.

Step E: (1-Oxo-1H-isochromen-6-yl)acetaldehyde

To a solution of 6-(1,3-dioxolan-2ylmethyl)-1H-isochromen-1-one (410 mg, 1.8 mmol) in dioxane (20 mL) was added HCl (20 ml, 3M), and then stirred for 16 hours. The reaction was extracted with ethyl acetate then separated. The organic layer was washed with brine, dried over $Na_2SO_4$, filtered and concentrated to yield the title product. LC-MS (IE, m/z): 189 $[M+1]^+$.

Intermediate 39

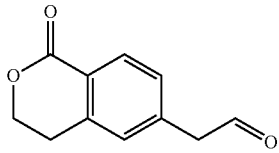 [SMILES: O=CCc1ccc2c(c1)CCOC2=O]

(1-Oxo-3,4-dihydro-1H-isochromen-6-yl)acetaldehyde

Step A: 6-(1,3-dioxolan-2-ylmethyl)-3,4-dihydro-1H-isochromen-1-one 6-bromo-3,4-dihydro-1H-isochromen-1-one (10 g, 44 mmol) was combined with tri-t-butyl phosphonium tetrafluoroborate (256 mg, 0.881 mmol), palladium (II) acetate (99 mg, 0.44 mmol) and commercially available bromo(1,3-dioxolan-2-ylmethyl)zinc solution (0.5 M, 97 mL, 48 mmol) in DMF (100 mL), and the mixture was degassed three times by alternating vacuum and nitrogen purge. The mixture was then heated at 85° C. for 6 h, then was stirred at RT overnight. Ethyl acetate and ether were added and the mixture was washed with water. The aqueous layer was extracted with ethyl acetate, the organic layers were combined, and washed twice with water and once with brine. The organic layer was dried over $MgSO_4$, filtered and concentrated. The crude product was purified by MPLC (silica) eluting with ethyl acetate in hexanes to afford the title compound. LCMS: m/z 235 $(M+1)^+$.

Step B:
(1-oxo-3,4-dihydro-1H-isochromen-6-yl)acetaldehyde 6-(1,3-Dioxolan-2-ylmethyl)-3,4-dihydro-1H-isochromen-1-one (4.42 g, 18.9 mmol) was dissolved in dioxane (25 mL) and treated with 3 M HCl (40 mL). The reaction mixture was stirred at RT over night, and then was warmed to 50° C. for 2 hrs to drive the reaction to completion. Ethyl acetate was added and the layers were separated. The aqueous layer was extracted again with ethyl acetate, and the combined organic layers were washed with brine and dried over $MgSO_4$ to afford the title compound. LCMS: m/z 191 $(M+1)^+$.

Intermediates described above may be referred to by their number preceded by "I-". For example, Intermediate 5 is shortened to I-5.

Example 1

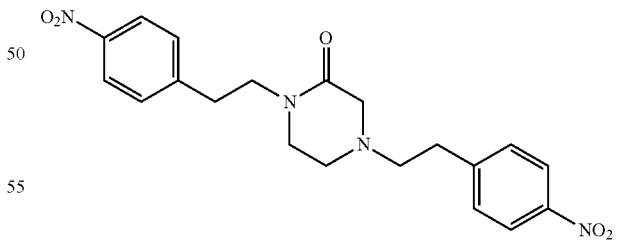

1,4-bis[2-(4-nitrophenyl)ethyl]piperazin-2-one

A mixture of 1-[2-(4-nitrophenyl)ethyl]piperazin-2-one hydrochloride (40 mg, 0.14 mmol) and 1-(2-bromoethyl)-4-nitrobenzene (39 mg, 0.17 mmol) was heated to 60° C. with triethylamine (0.078 mL, 0.56 mmol) for 16 hours. LC showed complete reaction at that point. The desired product Example 2

Mixture of 2 Enantiomers

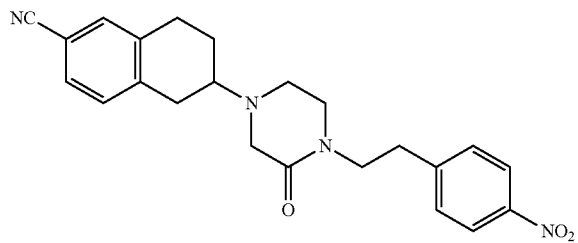 [SMILES: N#Cc1ccc2c(c1)CCC(N1CCN(CCc3ccc([N+](=O)[O-])cc3)C(=O)C1)C2]

6-(4-(4-nitrophenethyl)-3-oxopiperazin-1-yl)-5,6,7,8-tetrahydronaphthalene-2-carbonitrile A mixture of 6-Oxo-5,6,7,8-tetrahydronaphthalene-2-carbonitrile (24 mg, 0.14 mmol) and 1-[2-(4-nitrophenyl)ethyl]piperazin-2-one (20 mg, 0.070 mmol) was treated with titanium(IV) isopropoxide (0.10 ml, 0.35 mmol) for 30 minutes. Then the reaction was diluted with ethanol (5 mL), and sodium cyanoborohydride (44 mg, 0.70 mmol) was added. The reaction was stirred at RT overnight. The reaction was diluted with EtOAc, washed with brine, dried over sodium sulfate, and concentrated to give the crude residue. The desired product was purified by reverse phase HPLC (AcCN-Water with 0.1% TFA). LC-MS (IE, m/z): 405 [M+1]+.

Example 3

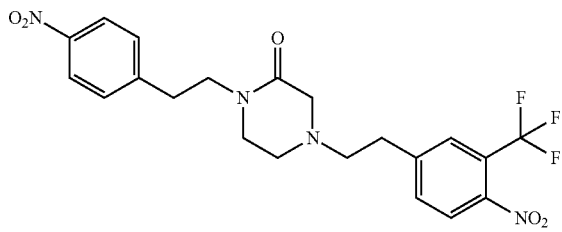 [SMILES: O=C1CN(CCc2ccc([N+](=O)[O-])c(C(F)(F)F)c2)CCN1CCc1ccc([N+](=O)[O-])cc1]

1-[2-(4-Nitrophenyl)ethyl]-4-{2-[4-nitro-3-(trifluoromethyl)phenyl]ethyl}piperazin-2-one Step A: 1-Nitro-4-(prop-2-en-1-yl)-2-(trifluoromethyl)benzene A mixture of 4-bromo-1-nitro-2-(trifluoromethyl)benzene (1.0 g, 3.7 mmol), allyl tri-n-butyltin (1.4 mL, 4.4 mmol), lithium chloride (470 mg, 11 mmol), and palladium tetrakis (210 mg, 0.18 mmol) in toluene (30 mL) was heated to reflux for 16 hours under nitrogen. TLC showed complete reaction at that point. The reaction was diluted with ethyl acetate, adsorbed onto silica gel, and purified by silica gel chromatography to afford the title product.

Step B: 1-[2-(4-nitrophenyl)ethyl]-4-{2-[4-nitro-3-(trifluoromethyl)phenyl]ethyl}piperazin-2-one A solution of 1-nitro-4-(prop-2-en-1-yl)-2-(trifluoromethyl)benzene in methanol and cooled to −78° C. Ozone was bubbled through the solution until it turned blue. Excess ozone was removed by bubbling nitrogen through the solution, followed by addition of triphenylphosphine (1.1 g, 4.3 mmol). The mixture was warmed up naturally. TLC showed formation of the desired product. The crude material was adsorbed onto silica gel, and purified by flash chromatography to afford the desired [4-nitro-3-(trifluoromethyl)phenyl]acetaldehyde. The aldehyde (20 mg, 0.070 mmol) was treated with 1-[2-(4-nitrophenyl)ethyl]piperazin-2-one (16 mg, 0.070 mmol) and titanium(IV) isopropoxide (0.20 mL). After stirring the mixture for 15 minutes, ethanol (2 mL) and sodium cyanoborohydride (44 mg, 0.70 mmol) was added into the reaction. The mixture was allowed to stir for 4 hours. LC showed formation of the desired product. The reaction was diluted with ethyl acetate, washed with brine, dried over sodium sulfate, and concentrated to give the crude product. The crude product was purified by mass-directed reverse phase HPLC (AcCN-Water with 0.1% TFA). LC-MS (IE, m/z): 467 [M+1]+.

Example 4

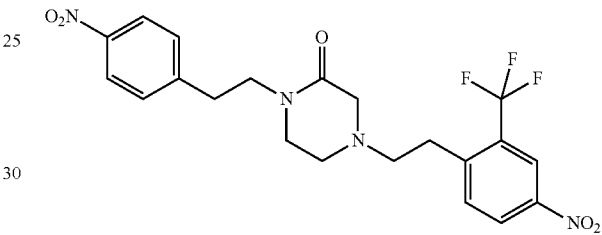

1-[2-(4-Nitrophenyl)ethyl]-4-{2-[4-nitro-2-(trifluoromethyl)phenyl]ethyl}piperazin-2-one Step A: 4-Nitro-1-(prop-2-en-1-yl)-2-(trifluoromethyl)benzene A mixture of 1-bromo-4-nitro-2-(trifluoromethyl)benzene (1.0 g, 3.7 mmol), Allyl Tri-n-butyltin (1.4 mL, 4.4 mmol), Lithium Chloride (470 mg, 11 mmol), and Palladium Tetrakis (210 mg, 0.18 mmol) in toluene (30 mL) was heated to reflux for 16 hours under nitrogen. TLC showed complete reaction at that point. The reaction was diluted with ethyl acetate, adsorbed onto silica gel, and purified by silica gel chromatography to afford the title product.

Step B: 1-[2-(4-nitrophenyl)ethyl]-4-{2-[4-nitro-2-(trifluoromethyl)phenyl]ethyl}piperazin-2-one A solution of 4-Nitro-1-(prop-2-en-1-yl)-2-(trifluoromethyl)benzene (300 mg, 1.3 mmol) in methanol and cooled to −78° C. Ozone was bubbled through the solution until it turned blue. Excess ozone was removed by bubbling nitrogen through the solution, followed by addition of triphenylphosphine (0.68 g, 2.6 mmol). The mixture was warmed up naturally. TLC showed formation of the desired product. The crude material was adsorbed onto silica gel, and purified by flash chromatography to afford [4-nitro-3-(trifluoromethyl)phenyl]acetaldehyde. The aldehyde (20 mg, 0.070 mmol) was treated with 1-[2-(4-nitrophenyl)ethyl]piperazin-2-one (16 mg, 0.070 mmol) and titanium(IV) isopropoxide (0.20 mL). After stirring the mixture for 15 minutes, ethanol (2 mL) and sodium cyanoborohydride (44 mg, 0.70 mmol) was added into the reaction. The mixture was allowed to stir for 4 hours. LC showed formation of the desired product. The reaction was diluted with ethyl acetate, washed with brine, dried over sodium sulfate, and concentrated to give the crude residue. The desired product was purified by mass-directed reverse phase HPLC (AcCN-Water with 0.1% TFA). LC-MS (IE, m/z): 467 [M+1]+.

Example 5

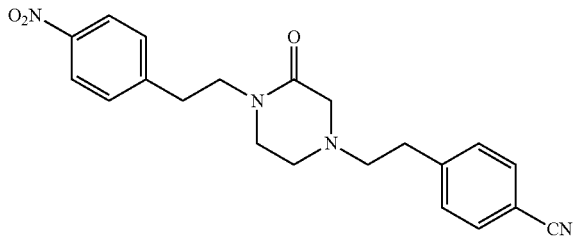 [SMILES: N#Cc1ccc(CCN2CCN(CCc3ccc([N+](=O)[O-])cc3)C(=O)C2)cc1]

4-(2-{4-[2-(4-Nitrophenyl)ethyl]-3-oxopiperazin-1-yl}ethyl)benzonitrile

Step A: 4-(2-Oxoethyl)benzonitrile

To a solution of 4-(2-Hydroxyethyl)benzonitrile (0.38 g, 2.6 mmol) in DCM (5 mL) was added Dess-Martin reagent (1.7 g, 3.9 mmol). The mixture was allowed to stir at RT for 1 hour. TLC showed no starting material at that point. The reaction was diluted with DCM, worked up with $Na_2S_2O_3$, washed with sodium bicarbonate, dried over sodium sulfate, and concentrated. The crude 4-(2-Oxoethyl)benzonitrile was used in the next step without further purification.

Step B: 4-(2-{4-[2-(4-Nitrophenyl)ethyl]-3-oxopiperazin-1-yl}ethyl)benzonitrile

The crude 4-(2-Oxoethyl)benzonitrile (100 mg, 0.69 mmol) was treated with 1-[2-(4-nitrophenyl)ethyl]piperazin-2-one (197 mg, 0.69 mmol) and titanium(IV) isopropoxide (2.0 mL). After stirring the mixture for 15 minutes, ethanol and sodium cyanoborohydride was added into the reaction. The mixture was allowed to stir for 4 hours. The reaction was diluted with ethyl acetate, washed with brine, dried over sodium sulfate, and concentrated to give the crude residue. The desired product was purified by mass-directed reverse phase HPLC (AcCN-Water with 0.1% TFA). LC-MS (IE, m/z): 378 [M+1]+.

Example 6

Mixture of 2 Enantiomers

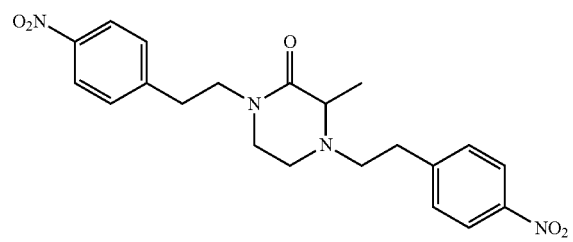 [SMILES: CC1C(=O)N(CCc2ccc([N+](=O)[O-])cc2)CCN1CCc1ccc([N+](=O)[O-])cc1]

3-Methyl-1,4-bis[2-(4-nitrophenyl)ethyl]piperazin-2-one

To a mixture of 3-Methyl-1-[2-(4-nitrophenyl)ethyl]piperazin-2-one hydrochloride (38 mg, 0.13 mmol) and (4-Nitrophenyl)acetaldehyde (31 mg, 0.19 mmol) was added titanium(IV) isopropoxide (0.37 mL, 1.3 mmol). After stirring the mixture at RT for 15 minutes, ethanol (2 mL) and sodium cyanoborohydride (80 mg, 1.3 mmol) were added to the reaction. The mixture was allowed to stir at RT for 16 hours. The reaction was diluted with ethyl acetate, washed with brine, dried over sodium sulfate, and concentrated to give the crude title product. The title product was purified by mass-directed reverse phase HPLC (AcCN-Water with 0.1% TFA). LC-MS (IE, m/z): 413 [M+1]+.

Example 7

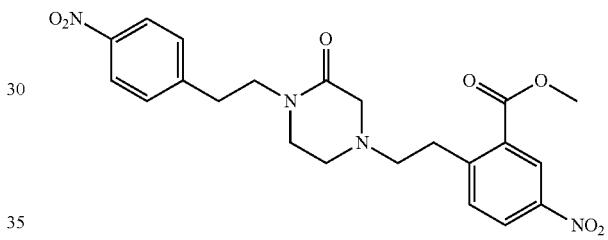

Methyl 5-nitro-2-(2-{4-[2-(4-nitrophenyl)ethyl]-3-oxopiperazin-1-yl}ethyl)benzoate The title compound was prepared from 1-[2-(4-Nitrophenyl)ethyl]piperazin-2-one and Methyl 5-nitro-2-(2-oxoethyl)benzoate following essentially the same procedure as Example 6. The product was purified by mass-directed reverse phase HPLC (AcCN-Water with 0.1% TFA). LC-MS (IE, m/z): 457 [M+1]+.

Example 8

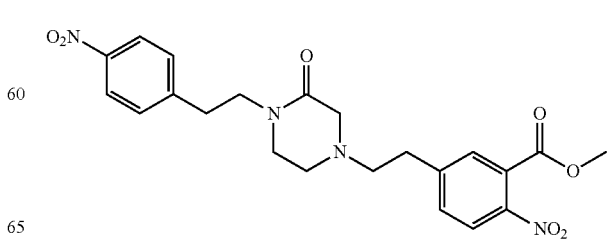

Methyl 2-nitro-5-(2-{4-[2-(4-nitrophenyl)ethyl]-3-oxopiperazin-1-yl}ethyl)benzoate The title compound was prepared from 1-[2-(4-Nitrophenyl)ethyl]piperazin-2-one and Methyl 2-nitro-5-(2-oxoethyl)benzoate following essentially the same procedure as Example 6. The product was purified by mass-directed reverse phase HPLC (AcCN-Water with 0.1% TFA). LC-MS (IE, m/z): 457 [M+1]$^+$.

Example 9

Mixture of 2 Enantiomers

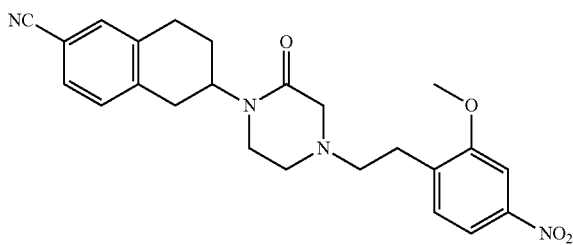 [SMILES: COc1cc([N+](=O)[O-])ccc1CCN1CCN(C2CCc3cc(C#N)ccc3C2)C(=O)C1]

6-{4-[2-(2-Methoxy-4-nitrophenyl)ethyl]-2-oxopiperazin-1-yl}-5,6,7,8-tetrahydronaphthalene-2-carbonitrile The title compound was prepared from 6-(2-Oxopiperazin-1-yl)-5,6,7,8-tetrahydronaphthalene-2-carbonitrile and (2-Methoxy-4-nitrophenyl)acetaldehyde following essentially the same procedure as Example 6. The product was purified by mass-directed reverse phase HPLC (AcCN-Water with 0.1% TFA). LC-MS (IE, m/z): 435 [M+1]$^+$.

Example 10

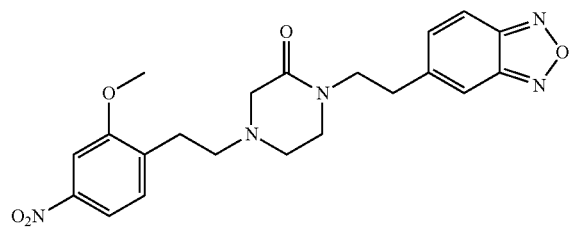 [SMILES: COc1cc([N+](=O)[O-])ccc1CCN1CCN(CCc2ccc3nonc3c2)C(=O)C1]

1-[2-(2,1,3-Benzoxadiazol-5-yl)ethyl]-4-[2-(2-methoxy-4-nitrophenyl)ethyl]piperazin-2-one The title compound was prepared from 1-[2-(2,1,3-Benzoxadiazol-5-yl)ethyl]piperazin-2-one and (2-Methoxy-4-nitrophenyl)acetaldehyde following essentially the same procedure as Example 6. The product was purified by mass-directed reverse phase HPLC (AcCN-Water with 0.1% TFA). LC-MS (IE, m/z): 426 [M+1]$^+$.

Example 11

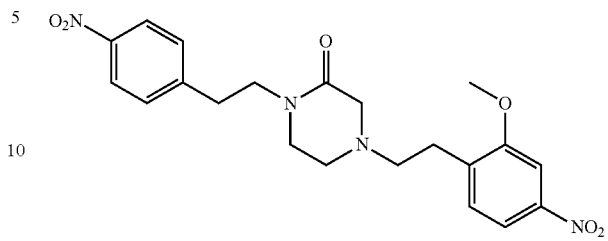

4-[2-(2-Methoxy-4-nitrophenyl)ethyl]-1-[2-(4-nitrophenyl)ethyl]piperazin-2-one

The title compound was prepared from 1-[2-(4-Nitrophenyl)ethyl]piperazin-2-one and (2-Methoxy-4-nitrophenyl)acetaldehyde following essentially the same procedure as Example 6. The product was purified by mass-directed reverse phase HPLC (AcCN-Water with 0.1% TFA). LC-MS (IE, m/z): 429 [M+1]$^+$.

Example 12

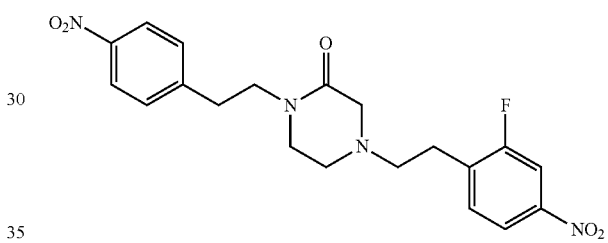

4-[2-(2-Fluoro-4-nitrophenyl)ethyl]-1-[2-(4-nitrophenyl)ethyl]piperazin-2-one

The title compound was prepared from 1-[2-(4-Nitrophenyl)ethyl]piperazin-2-one and (2-Fluoro-4-nitrophenyl)acetaldehyde following essentially the same procedure as Example 6. The product was purified by mass-directed reverse phase HPLC (AcCN-Water with 0.1% TFA). LC-MS (IE, m/z): 417 [M+1]$^+$.

Example 13

Mixture of 2 Enantiomers

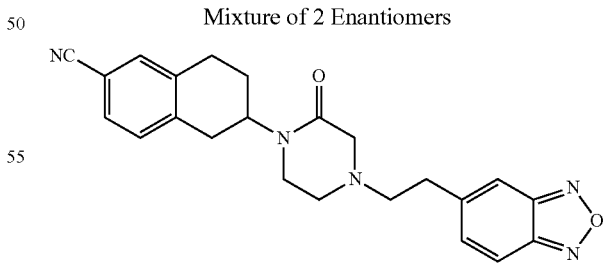

6-{4-[2-(2,1,3-Benzoxadiazol-5-yl)ethyl]-2-oxopiperazin-1-yl}-5,6,7,8-tetrahydronaphthalene-2-carbonitrile The title compound was prepared from 6-(2-Oxopiperazin-1-yl)-5,6,7,8-tetrahydronaphthalene-2-carbonitrile and 2,1, 3-benzoxadiazol-5-ylacetaldehyde following essentially the same procedure as Example 6. The product was purified by mass-directed reverse phase HPLC (AcCN-Water with 0.1% TFA). LC-MS (IE, m/z): 402 [M+1]$^+$.

Example 14

Mixture of 2 Enantiomers

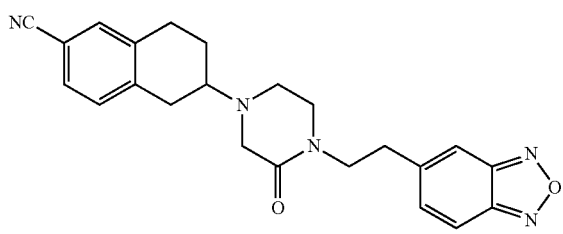 [SMILES: N#Cc1ccc2c(c1)CCC(N1CCN(CCc3ccc4nonc4c3)C(=O)C1)C2]

6-{4-[2-(2,1,3-Benzoxadiazol-5-yl)ethyl]-3-oxopiperazin-1-yl}-5,6,7,8-tetrahydronaphthalene-2-carbonitrile The title compound was prepared from 1-[2-(2,1,3-Benzoxadiazol-5-yl)ethyl]piperazin-2-one and 6-Oxo-5,6,7,8-tetrahydronaphthalene-2-carbonitrile following essentially the same procedure as Example 6. The product was purified by mass-directed reverse phase HPLC (AcCN-Water with 0.1% TFA). LC-MS (IE, m/z): 402 [M+1]$^+$.

Example 15

4 Diastereomers

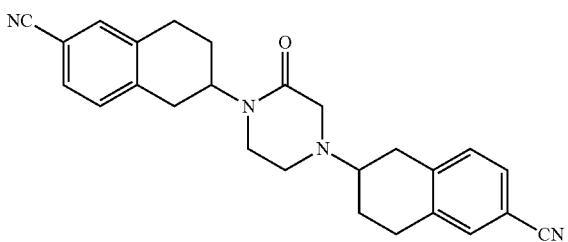 [SMILES: N#Cc1ccc2c(c1)CCC(N1CCN(C3CCc4cc(C#N)ccc4C3)C(=O)C1)C2]

6,6'-(2-Oxopiperazine-1,4-diyl)di(5,6,7,8-tetrahydronaphthalene-2-carbonitrile)

The title compound was prepared from 6-(2-Oxopiperazin-1-yl)-5,6,7,8-tetrahydronaphthalene-2-carbonitrile and 6-Oxo-5,6,7,8-tetrahydronaphthalene-2-carbonitrile following essentially the same procedure as Example 6. The product was purified by mass-directed reverse phase HPLC (AcCN-Water with 0.1% TFA). LC-MS (IE, m/z): 411 [M+1]$^+$.

Example 16

2 Diastereomers

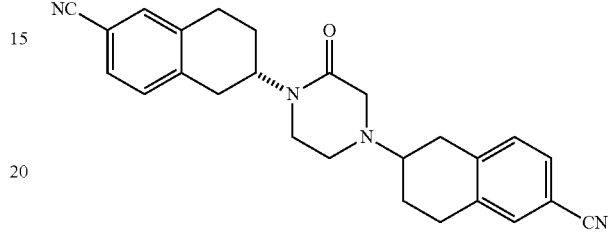

(6S)-6,6'-(2-oxopiperazine-1,4-diyl)-di-(5,6,7,8-tetrahydronaphthalene-2-carbonitrile)

The title compound was prepared from (6S)-6-(2-Oxopiperazin-1-yl)-5,6,7,8-tetrahydronaphthalene-2-carbonitrile and 6-Oxo-5,6,7,8-tetrahydronaphthalene-2-carbonitrile following essentially the same procedure as Example 6. The product was purified by mass-directed reverse phase HPLC (AcCN-Water with 0.1% TFA). LC-MS (IE, m/z): 411 [M+1]$^+$.

Example 17

2 Diastereomers

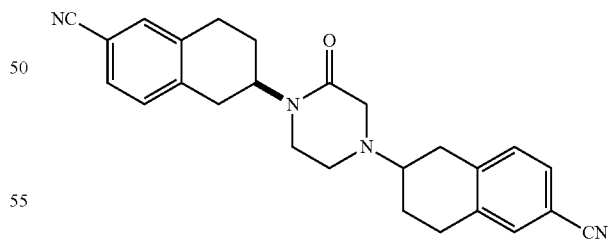

(6R)-6,6'-(2-oxopiperazine-1,4-diyl)-di-(5,6,7,8-tetrahydronaphthalene-2-carbonitrile)

The title compound was prepared from (6R)-6-(2-Oxopiperazin-1-yl)-5,6,7,8-tetrahydronaphthalene-2-carbonitrile and 6-Oxo-5,6,7,8-tetrahydronaphthalene-2-carbonitrile following essentially the same procedure as Example 6. The product was purified by mass-directed reverse phase HPLC (AcCN-Water with 0.1% TFA). LC-MS (IE, m/z): 411 [M+1]+.

Example 18

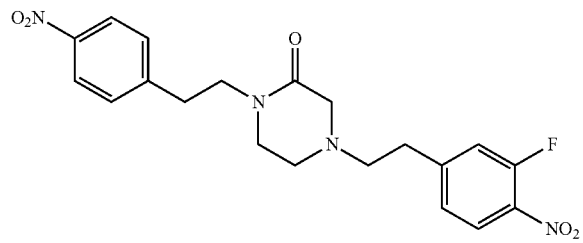 [SMILES: O=C1CN(CCc2ccc([N+](=O)[O-])c(F)c2)CCN1CCc1ccc([N+](=O)[O-])cc1]

4-[2-(3-Fluoro-4-nitrophenyl)ethyl]-1-[2-(4-nitrophenyl)ethyl]piperazin-2-one

The title compound was prepared from 1-[2-(4-Nitrophenyl)ethyl]piperazin-2-one and (3-Fluoro-4-nitrophenyl)acetaldehyde following essentially the same procedure as Example 6. The product was purified by mass-directed reverse phase HPLC (AcCN-Water with 0.1% TFA). LC-MS (IE, m/z): 417 [M+1]+.

Example 19

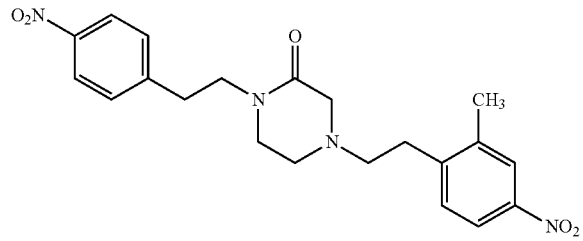 [SMILES: Cc1cc([N+](=O)[O-])ccc1CCN1CCN(CCc2ccc([N+](=O)[O-])cc2)C(=O)C1]

4-[2-(2-Methyl-4-nitrophenyl)ethyl]-1-[2-(4-nitrophenyl)ethyl]piperazin-2-one

The title compound was prepared from 1-[2-(4-Nitrophenyl)ethyl]piperazin-2-one and (2-Methyl-4-nitrophenyl)acetaldehyde following essentially the same procedure as Example 6. The product was purified by mass-directed reverse phase HPLC (AcCN-Water with 0.1% TFA). LC-MS (IE, m/z): 413 [M+1]+.

Example 20

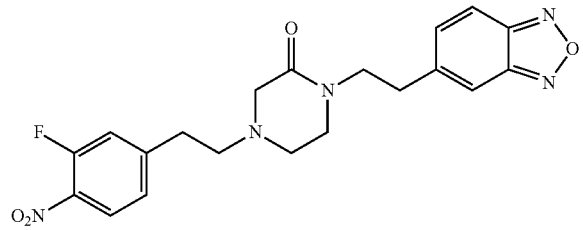 [SMILES: O=C1CN(CCc2ccc([N+](=O)[O-])c(F)c2)CCN1CCc1ccc2nonc2c1]

1-[2-(2,1,3-Benzoxadiazol-5-yl)ethyl]-4-[2-(3-fluoro-4-nitrophenyl)ethyl]piperazin-2-one The title compound was prepared from 1-[2-(2,1,3-Benzoxadiazol-5-yl)ethyl]piperazin-2-one and (3-Fluoro-4-nitrophenyl)acetaldehyde following essentially the same procedure as Example 6. The product was purified by mass-directed reverse phase HPLC (AcCN-Water with 0.1% TFA). LC-MS (IE, m/z): 414 [M+1]+.

Example 21

Mixture of 2 Enantiomers

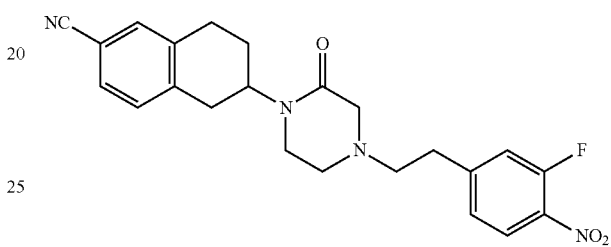

6-{4-[2-(3-Fluoro-4-nitrophenyl)ethyl]-2-oxopiperazin-1-yl}-5,6,7,8-tetrahydronaphthalene-2-carbonitrile The title compound was prepared from 6-(2-Oxopiperazin-1-yl)-5,6,7,8-tetrahydronaphthalene-2-carbonitrile and (3-Fluoro-4-nitrophenyl)acetaldehyde following essentially the same procedure as Example 6. The product was purified by mass-directed reverse phase HPLC (AcCN-Water with 0.1% TFA). LC-MS (IE, m/z): 411 [M+1]+.

Example 22

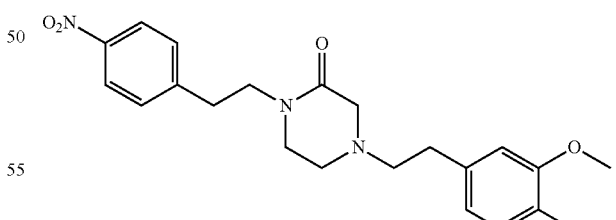

4-[2-(3-Methoxy-4-nitrophenyl)ethyl]-1-[2-(4-nitrophenyl)ethyl]piperazin-2-one

The title compound was prepared from 1-[2-(4-Nitrophenyl)ethyl]piperazin-2-one and (3-Methoxy-4-nitrophenyl)acetaldehyde following essentially the same procedure as Example 6. The product was purified by mass-directed reverse phase HPLC (AcCN-Water with 0.1% TFA). LC-MS (IE, m/z): 429 [M+1]+.

Example 23

Mixture of 2 Enantiomers

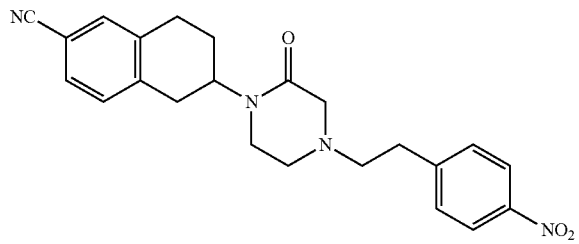 [SMILES: N#Cc1ccc2c(c1)CCC(N1CCN(CCc3ccc([N+](=O)[O-])cc3)CC1=O)C2]

6-{4-[2-(4-Nitrophenyl)ethyl]-2-oxopiperazin-1-yl}-5,6,7,8-tetrahydronaphthalene-2-carbonitrile To a solution of 6-(2-Oxopiperazin-1-yl)-5,6,7,8-tetrahydronaphthalene-2-carbonitrile (20 mg, 0.078 mmol) in DMF (1 mL) was added 1-(2-Iodoethyl)-4-nitrobenzene (26 mg, 0.094 mmol) and K$_2$CO$_3$ (43 mg, 0.31 mmol). The mixture was allowed to stir at RT for 16 hours. LC showed product formation. The desired product was purified by mass-directed reverse phase HPLC (AcCN-Water with 0.1% TFA). LC-MS (IE, m/z): 405 [M+1]+.

Example 24

Mixture of 2 Enantiomers

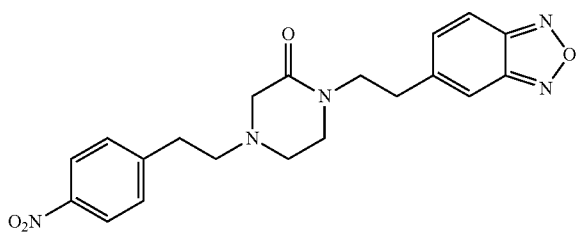 [SMILES: O=C1CN(CCc2ccc([N+](=O)[O-])cc2)CCN1CCc1ccc2nonc2c1]

1-[2-(2,1,3-Benzoxadiazol-5-yl)ethyl]-4-[2-(4-nitrophenyl)ethyl]piperazin-2-one

To a solution of 1-[2-(2,1,3-Benzoxadiazol-5-yl)ethyl]piperazin-2-one (20 mg, 0.081 mmol) in DMF (1 mL) was added 1-(2-Iodoethyl)-4-nitrobenzene (27 mg, 0.097 mmol) and K$_2$CO$_3$ (45 mg, 0.32 mmol). The mixture was allowed to stir at RT for 16 hours. LC showed product formation. The desired product was purified by mass-directed reverse phase HPLC (AcCN-Water with 0.1% TFA). LC-MS (IE, m/z): 396 [M+1]+.

Example 25

Mixture of 2 Enantiomers

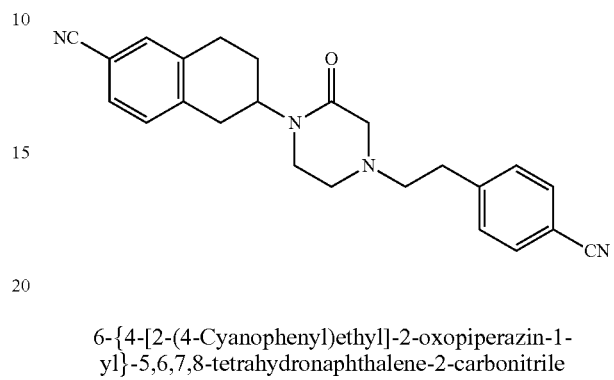

6-{4-[2-(4-Cyanophenyl)ethyl]-2-oxopiperazin-1-yl}-5,6,7,8-tetrahydronaphthalene-2-carbonitrile To a flask charged with 6-(2-Oxopiperazin-1-yl)-5,6,7,8-tetrahydronaphthalene-2-carbonitrile (30 mg, 0.12 mmol) and a stir bar was added 1-(2-Bromoethyl)-4-nitrobenzene (39 mg, 0.19 mmol), K$_2$CO$_3$ (69 mg, 0.50 mmol), Tetrabutylammonium Iodide (12 mg, 0.025 mmol), and DMF (1 mL). The mixture was heated to 50° C. for 16 hours. LC showed product formation. The desired product was purified by mass-directed reverse phase HPLC (AcCN-Water with 0.1% TFA). LC-MS (IE, m/z): 385 [M+1]+.

Example 26

Mixture of 2 Enantiomers

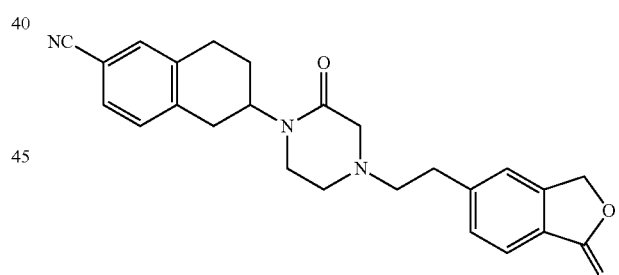

6-{2-Oxo-4-[2-(1-oxo-1,3-dihydro-2-benzofuran-5-yl)ethyl]piperazin-1-yl}-5,6,7,8-tetrahydronaphthalene-2-carbonitrile Step A: 5-(prop-2-en-1-yl)-2-benzofuran-1(3H)-one A 4-neck, 22-L, round bottom flask equipped with a mechanical stirrer, thermocouple, nitrogen bubbler, and condenser was charged with 5-bromophthalide (650 g, 3.0 mol), allyltri-n-butyltin (1200 g, 3.6 mol), palladium tetrakis triphenylphosphine (100 g, 0.089 mol), lithium chloride (250 g, 5.9 mol) and toluene (8.8 L). The mixture was evacuated and flushed with nitrogen 3 times and then was stirred at 100° C. for 4 hours. After slowly cooling to ambient temperature, the mixture was filtered and concentrated. The resulting solid was purified by silica gel column chromatography (heptane: ethyl acetate, 0→40%) to provide 5-(prop-2-en-1-yl)-2-benzofuran-1(3H)-one.

Step B: 6-{2-Oxo-4-[2-(1-oxo-1,3-dihydro-2-benzofuran-5-yl)ethyl]piperazin-1-yl}-5,6,7,8-tetrahydronaphthalene-2-carbonitrile Ozone was bubbled into a solution of 5-(prop-2-en-1-yl)-2-benzofuran-1(3H)-one (102 mg, 0.59 mmol) in DCM until the color changed to orange. Excess ozone was removed by bubbling nitrogen through the reaction, which was followed by addition of 6-(2-Oxopiperazin-1-yl)-5,6,7,8-tetrahydronaphthalene-2-carbonitrile (50 mg, 0.20 mmol) and sodium triacetoxyborohydride (210 mg, 0.98 mmol). The reaction was allowed to stir at RT for 24 hours. The reaction was diluted with DCM, washed with brine, dried over MgSO$_4$, and purified by prep-TLC to afford the title product. LC-MS (IE, m/z): 416 [M+1]$^+$.

Example 27

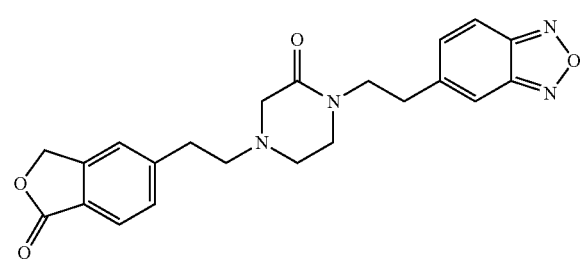 [SMILES: O=C1OCc2cc(CCN3CCN(CCc4ccc5nonc5c4)C(=O)C3)ccc21]

1-[2-(2,1,3-Benzoxadiazol-5-yl)ethyl]-4-[2-(1-oxo-1,3-dihydro-2-benzofuran-5-yl)ethyl]piperazin-2-one A mixture of 1-[2-(2,1,3-Benzoxadiazol-5-yl)ethyl]piperazin-2-one (54 mg, 0.22 mmol), 5-(2-Bromoethyl)-2-benzofuran-1(3H)-one (105 mg, 0.44 mol), Triethylamine (0.15 mL, 1.1 mmol), and DMF (1.5 mL) was heated to 60° C. for 24 hours. The reaction was diluted with EtOAc, washed with water and brine, dried over MgSO$_4$, and purified by prep-TLC (5% MeOH in DCM) to deliver the title product. LC-MS (IE, m/z): 407 [M+1]$^+$.

Example 28

Mixture of 2 Enantiomers

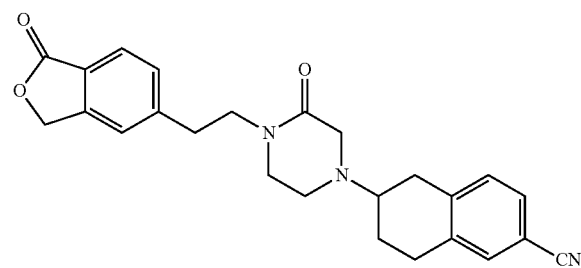 [SMILES: N#Cc1ccc2c(c1)CCC(N1CCN(CCc3ccc4c(c3)COC4=O)C(=O)C1)C2]

6-{3-Oxo-4-[2-(1-oxo-1,3-dihydro-2-benzofuran-5-yl)ethyl]piperazin-1-yl}-5,6,7,8-tetrahydronaphthalene-2-carbonitrile The title compound was prepared from 1-[2-(1-Oxo-1,3-dihydro-2-benzofuran-5-yl)ethyl]piperazin-2-one and 6-Oxo-5,6,7,8-tetrahydronaphthalene-2-carbonitrile following essentially the same procedure as Example 6. The product was purified by mass-directed reverse phase HPLC (AcCN-Water with 0.1% TFA). LC-MS (IE, m/z): 416 [M+1]$^+$.

Example 29

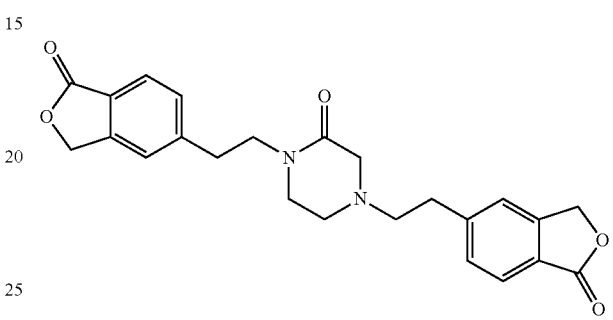

1,4-Bis[2-(1-oxo-1,3-dihydro-2-benzofuran-5-yl)ethyl]piperazin-2-one

To a solution of 1-[2-(1-Oxo-1,3-dihydro-2-benzofuran-5-yl)ethyl]piperazin-2-one (30 mg, 0.12 mmol) and 5-(2-Bromoethyl)-2-benzofuran-1(3H)-one (56 mg, 0.23 mmol) in DMF (2 ml) was added TEA (0.048 ml, 0.35 mmol) and tetrabutylammonium iodide (4.3 mg, 0.012 mmol). The mixture was heated to 55° C. for 16 hours. LC showed formation of the desired product, which was purified by mass-directed reverse phase HPLC (AcCN-Water with 0.1% TFA). LC-MS (IE, m/z): 421 [M+1]$^+$.

Example 30

Mixture of 2 Enantiomers

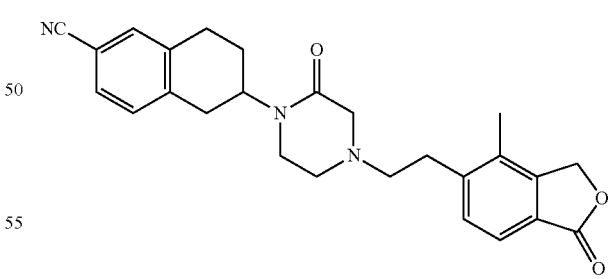

6-{4-[2-(4-Methyl-1-oxo-1,3-dihydro-2-benzofuran-5-yl)ethyl]-2-oxopiperazin-1-yl}-5,6,7,8-tetrahydronaphthalene-2-carbonitrile The title compound was prepared from 6-(2-Oxopiperazin-1-yl)-5,6,7,8-tetrahydronaphthalene-2-carbonitrile and (4-Methyl-1-oxo-1,3-dihydro-2-benzofuran-5-yl)acetaldehyde following essentially the same procedure as Example 6.

The product was purified by mass-directed reverse phase HPLC (AcCN-Water with 0.1% TFA). LC-MS (IE, m/z): 430 [M+1]+.

Example 31

Mixture of 2 Enantiomers

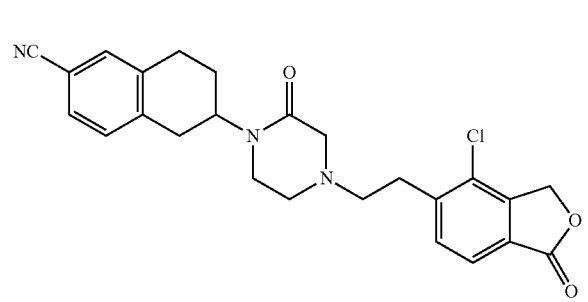 [SMILES: N#Cc1ccc2c(c1)CCC(N1CCN(CCc3ccc4c(c3Cl)COC4=O)CC1=O)C2]

6-{4-[2-(4-Chloro-1-oxo-1,3-dihydro-2-benzofuran-5-yl)ethyl]-2-oxopiperazin-1-yl}-5,6,7,8-tetrahydronaphthalene-2-carbonitrile The title compound was prepared from 6-(2-Oxopiperazin-1-yl)-5,6,7,8-tetrahydronaphthalene-2-carbonitrile and (4-Chloro-1-oxo-1,3-dihydro-2-benzofuran-5-yl)acetaldehyde following essentially the same procedure as Example 6. The product was purified by mass-directed reverse phase HPLC (AcCN-Water with 0.1% TFA). LC-MS (IE, m/z): 450 [M+1]+.

Example 32

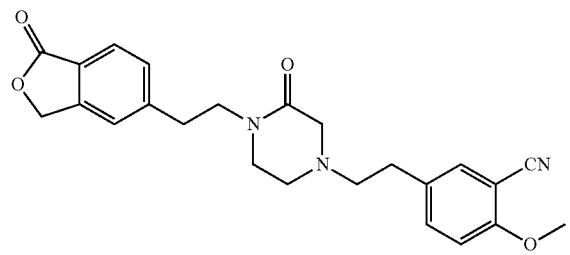 [SMILES: COc1ccc(CCN2CCN(CCc3ccc4c(c3)COC4=O)C(=O)C2)cc1C#N]

2-Methoxy-5-(2-{3-oxo-4-[2-(1-oxo-1,3-dihydro-2-benzofuran-5-yl)ethyl]piperazin-1-yl}ethyl)benzonitrile The title compound was prepared from 1-[2-(1-Oxo-1,3-dihydro-2-benzofuran-5-yl)ethyl]piperazin-2-one and 2-Methoxy-5-(2-oxoethyl)benzonitrile following essentially the same procedure as Example 6. The product was purified by mass-directed reverse phase HPLC (AcCN-Water with 0.1% TFA). LC-MS (IE, m/z): 420 [M+1]+.

Example 33

Mixture of 2 Enantiomers

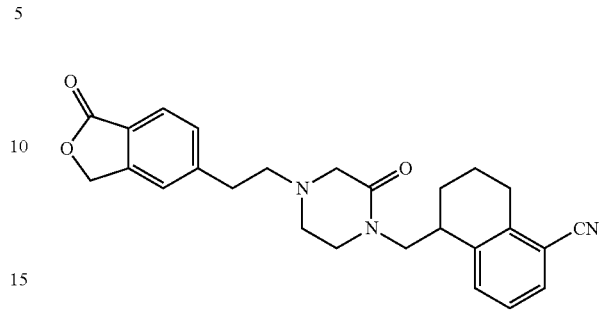

5-((2-oxo-4-(2-(1-oxo-1,3-dihydroisobenzofuran-5-yl)ethyl)piperazin-1-yl)methyl)-5,6,7,8-tetrahydronaphthalene-1-carbonitrile A solution of 5-(Piperazin-1-ylmethyl)-5,6,7,8-tetrahydronaphthalene-1-carbonitrile (30 mg, 0.11 mmol) in 2 mL DCM/MeOH (1/1) was added (1-Oxo-1,3-dihydro-2-benzofuran-5-yl)acetaldehyde (0.11 mmol), AcOH (6.6 mg, 0.11 mmol) and the reaction mixture was stirred for 2 hours, and then NaBH$_3$CH (14 mg, 0.22 mmol) was added. The resulting mixture was stirred overnight at ambient temperature. The product was purified by prep-TLC (DCM/MeOH=20:1) to afford the desired product. $^1$H-NMR (400 MHz, MeOD) δ ppm 7.76 (d, J=8.0 Hz, 1H), 7.44-7.51 (m, 4H), 7.24 (t, J=8.0 Hz, 1H), 5.33 (s, 2H), 3.74-3.80 (m, 1H), 3.32-3.45 (m, 3H), 3.22-3.27 (m, 1H), 3.20 (d, J=2.4 Hz, 2H), 2.96-3.03 (m, 3H), 2.73-2.85 (m, 5H), 1.93-2.02 (m, 1H), 1.75-1.84 (m, 3H).

Example 34

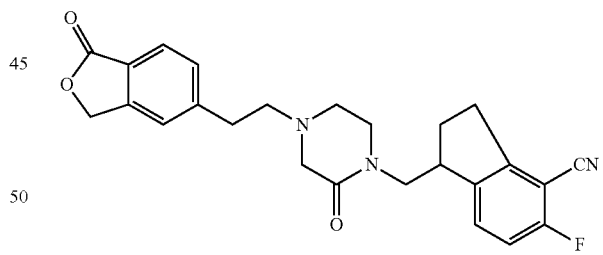

5-Fluoro-1-({2-oxo-4-[2-(1-oxo-1,3-dihydro-2-benzofuran-5-yl)ethyl]piperazin-1-yl}methyl)-2,3-dihydro-1H-indene-4-carbonitrile To a flask containing 5-Fluoro-1-[(2-oxopiperazin-1-yl)methyl]-2,3-dihydro-1H-indene-4-carbonitrile (5 mg, 0.018 mmol) and a stir bar was added (1-Oxo-1,3-dihydro-2-benzofuran-5-yl)acetaldehyde (16 mg, 0.091 mmol), Sodium Triacetoxyborohydride (19 mg, 0.091 mmol), and DCM (1 mL). The mixture was allowed to stir at RT for 16 hours. LC-MS indicated formation of the desired product. The solvent was removed, and the residue was redissolved in MeOH (1 mL). The sample was subjected to purification by reverse phase HPLC to afford the title compound. LC-MS (IE, m/z): 434 [M+1]⁺.

Example 35

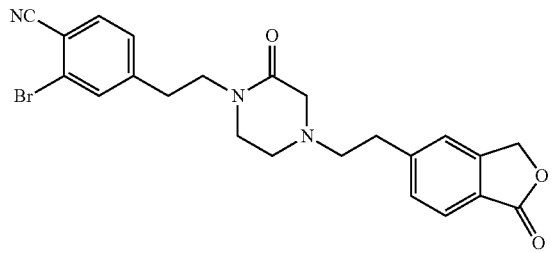 [SMILES: N#Cc1ccc(CCN2CCN(CCc3ccc4c(c3)COC4=O)CC2=O)cc1Br]

2-Bromo-4-(2-{2-oxo-4-[2-(1-oxo-1,3-dihydro-2-benzofuran-5-piperazin-1-yl}ethyl)benzonitrile A mixture of 2-Bromo-4-[2-(2-oxopiperazin-1-yl)ethyl]benzonitrile (100 mg, 0.32 mmol), (1-Oxo-1,3-dihydro-2-benzofuran-5-yl)acetaldehyde (100 mg, 0.57 mmol), NaBH₃CN (54 mg, 0.86 mmol) and AcOH (34 mg, 0.032 mmol) was dissolved in methanol and DCM (2 mL). The mixture was stirred at RT for 2 hours and the mixture was purified by Prep-HPLC to give the title product. ¹H-NMR (MeOD, 400 MHz) δ ppm 7.83 (d, J=7.8 Hz, 1H), 7.75 (d, J=1.2 Hz, 1H), 7.69 (d, J=7.8 Hz, 1H), 7.49-7.53 (m, 2H), 7.42-7.44 (m, 1H). 5.36 (s, 2H), 3.65-3.72 (m, 4H), 3.50-3.53 (m, 2H), 3.23-3.25 (m, 3H), 3.10-3.18 (m, 3H), 2.96 (t, J=7.2 Hz, 2H).

Example 36

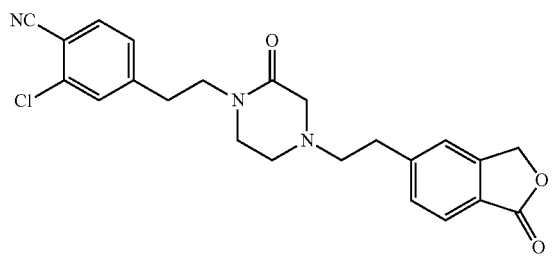 [SMILES: N#Cc1ccc(CCN2CCN(CCc3ccc4c(c3)COC4=O)CC2=O)cc1Cl]

2-Chloro-4-(2-{2-oxo-4-[2-(1-oxo-1,3-dihydro-2-benzofuran-5-yl)ethyl]piperazin-1-yl}ethyl)benzonitrile A mixture of 2-Chloro-4-[2-(2-oxopiperazin-1-yl)ethyl]benzonitrile (70 mg, 0.265 mmol), (1-Oxo-1,3-dihydro-2-benzofuran-5-yl)acetaldehyde (82 mg, 0.466 mmol), NaBH₃CN (43 mg, 0.68 mmol) and acetic acid (28 mg, 0.466 mmol) in methanol (2 mL) and DCM (2 mL) was stirred at RT for 3 hours. Then the mixture was purified by prep-TLC to give the title product. ¹H-NMR (MeOD, 400 MHz) δ ppm 7.83 (d, J=7.6 Hz, 1H), 7.71 (d, J=7.6 Hz, 1H), 7.58 (d, J=1.6 Hz, 1H), 7.54 (s, 1H), 7.50 (d, J=7.6 Hz, 1H), 7.38 (dd, J=1.6, 7.6 Hz, 1H), 5.36 (s, 2H), 3.78 (s, 2H), 3.68 (t, J=7.2 Hz, 2H), 3.56 (t, J=5.6 Hz, 2H), 3.40-3.42 (m, 2H), 3.30-3.33 (m, 2h), 3.13-3.18 (m, 2H), 2.98 (t, J=7.6 Hz, 2H).

Example 37

Mixture of 2 Enantiomers

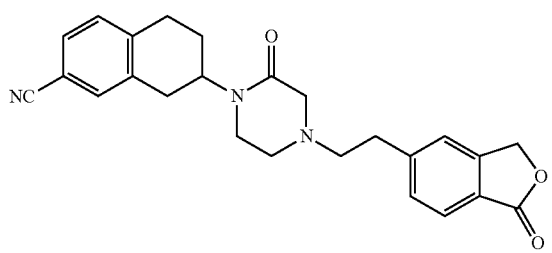 [SMILES: N#Cc1ccc2c(c1)CC(N1CCN(CCc3ccc4c(c3)COC4=O)CC1=O)CC2]

7-{2-Oxo-4-[2-(1-oxo-1,3-dihydro-2-benzofuran-5-yl)ethyl]piperazin-1-yl}-5,6,7,8-tetrahydronaphthalene-2-carbonitrile A solution of 7-(2-Oxopiperazin-1-yl)-5,6,7,8-tetrahydronaphthalene-2-carbonitrile (100 mg, 0.39 mmol) in 10 mL of anhydrous DCM was added (1-Oxo-1,3-dihydro-2-benzofuran-5-yl)acetaldehyde (69 mg, 0.39 mmol), NaBH(OAc)₃ (330 mg, 1.56 mmol) and the mixture was stirred at room temperature overnight. DCM was added, and the mixture was washed with brine. The organic layer was dried over anhydrous Na₂SO₄ and concentrated. The residue was purified by prep-TLC to give the desired product. ¹H-NMR (400 MHz, CDCl3) δ ppm 7.79 (d, J=7.5 Hz, 1H), 7.27-7.35 (m, 4H), 7.12 (d, J=8.3 Hz, 1H), 5.23 (s, 2H), 4.74-4.85 (m, 1H), 3.17-3.34 (m, 4H), 2.64-2.95 (m, 10H), 1.74-1.95 (m, 2H).

Example 38

Mixture of 2 Enantiomers

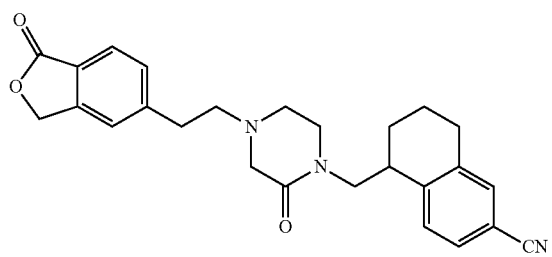 [SMILES: N#Cc1ccc2c(c1)CCCC2CN1CCN(CCc2ccc3c(c2)COC3=O)CC1=O]

5-({2-Oxo-4-[2-(1-oxo-1,3-dihydro-2-benzofuran-5-yl)ethyl]piperazin-1-yl}methyl)-5,6,7,8-tetrahydronaphthalene-2-carbonitrile To a mixture of 5-[(2-Oxopiperazin-1-yl)methyl]-5,6,7,8-tetrahydronaphthalene-2-carbonitrile (40 mg, 0.15 mmol), NaBH₃CN (19 mg, 0.30 mmol) and HOAc (18 mg, 0.298 mmol) in 20 mL MeOH was added (1-Oxo-1,3-dihydro-2-benzofuran-5-yl)acetaldehyde (52 mg, 0.30 mmol) and the mixture was stirred at RT overnight. Then saturated Na₂CO₃ (50 mL) was added and stirred for 30 min and extracted with EtOAc (3×50 mL). The combined organic layers were washed with water and brine, dried over anhydrous sodium sulfate, and concentrated. The residue was purified by prep-TLC to give the desired product. ¹H-NMR (400 MHz, MeOD) δ ppm 7.78 (d, J=7.8 Hz, 1H), 7.39~7.51 (m, 4H), 7.31 (d, J=7.8 Hz, 1H), 5.34 (s, 2H), 3.74~3.80 (m, 1H), 3.32~3.43 (m, 3H), 3.25~3.28 (m, 1H), 3.21 (s, 2H), 2.97~3.01 (m, 2H), 2.74~2.84 (m, 6H), 1.89~1.96 (m, 1H), 1.71~1.79 (m, 3H).

Example 39

Mixture of 2 Enantiomers

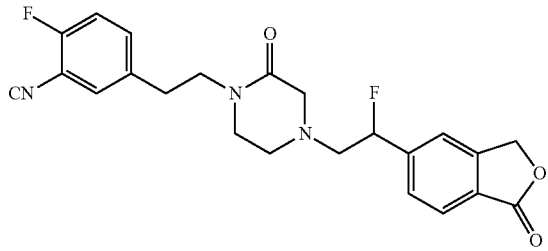

2-Fluoro-5-(2-{4-[2-fluoro-2-(1-oxo-1,3-dihydro-2-benzofuran-5-yl)ethyl]-2-oxopiperazin-1-yl}ethyl)benzonitrile Step A: (2E)-3-(1-oxo-1,3-dihydro-2-benzofuran-5-yl)prop-2-enal To a stirred solution of 5-Bromo-2-benzofuran-1(3H)-one (20 g, 94 mmol) in DMF (500 mL) was added Acrolein diethyl acetal (37 g, 282 mmol), Bu₄NOAc (57 g, 188 mmol), K₂CO₃ (19.5 g, 141 mmol), KCl (7.0 g, 94 mmol) and Pd(OAc)₂ (200 mg). The mixture was stirred for 2.5 hours at 90° C. After the mixture was cooled, 2 N HCl was slowly added and the resulting reaction mixture was stirred at room temperature for 10 min, and diluted with EtOAc, washed with water. The organic layer was dried over Na₂SO₄ and concentrated in vacuo. The residue was purified with silica gel chromatography (petrol ether/EtOAc=2:1) to give title product.

Step B: 5-[(1E)-3-hydroxyprop-1-en-1-yl]-2-benzofuran-1(3H)-one

To an ice-bath cooled flask containing a solution of (2E)-3-(1-oxo-1,3-dihydro-2-benzofuran-5-yl)prop-2-enal (5 g, 26.6 mmol) in THF (20 mL) and methanol (20 mL) was added NaBH₄ (1 g, 26.3 mmol), and the mixture was stirred for 1 hour at 0° C. The reaction mixture was then diluted with HCl (2 N, 20 mL) and extracted with EtOAc (300 mL). The organic layer was washed with water (30 mL) and brine (30 mL), dried over Na₂SO₄, and concentrated in vacuo. The residue was purified with silica gel chromatography (pet ether/EtOAc=2:1) to give the title product.

Step C: 5-[3-(Hydroxymethyl)oxiran-2-yl]-2-benzofuran-1 (3H)-one

A solution of 5-[(1E)-3-hydroxyprop-1-en-1-yl]-2-benzofuran-1(3H)-one (2.0 g, 10.5 mmol) in 50 mL of DCM was cooled to 0° C. and meta-chlorobenzoic acid (2.14 g, 10.53 mmol) in DCM (100 mL) was added dropwise. The temperature of the reaction mixture was then allowed to rise to RT. After 2 hours, the mixture was filtered and the filtrate was partitioned between DCM and water. The organic layer was washed with water (20 mL) and brine (20 mL), dried over Na₂SO₄, and concentrated in vacuo. The residue was purified with silica gel chromatography (petrol ether/EtOAc=2:1) to give the title product.

Step D: 5-(1-Fluoro-2,3-dihydroxypropyl)-2-benzofuran-1(3H)-one

A solution of 5-[3-(Hydroxymethyl)oxiran-2-yl]-2-benzofuran-1(3H)-one (1.2 g, 5.8 mmol) in TEA.3HF (triethylamine trihydrofluoride) (10 mL) was warmed to 110° C. for 8 hours, and then cooled to RT. The reaction mixture was extracted with EtOAc (200 mL), washed with NaHCO₃ (30 mL) and brine (30 mL). The organic layer was dried over Na₂SO₄, and then concentrated in vacuo. The residue was separated and purified with prep-TLC to give product the title product.

Step E: Fluoro(1-oxo-1,3-dihydro-2-benzofuran-5-yl)acetaldehyde

NaIO₄ (71 mg, 0.33 mmol) was added to a stirring solution of 5-(1-Fluoro-2,3-dihydroxypropyl)-2-benzofuran-1(3H)-one (30 mg, 0.13 mmol) in 5:2:2 CCl₄-H₂O-t-BuOH (5 mL) (the starting material was dissolved in CCl₄-t-BuOH, and H₂O was added last). After stirring 1.5 hours, the suspension was diluted with H₂O (3 mL) and extracted with CH₂Cl₂ (50 mL). The combined organic extracts were washed with 10% aqueous NaHSO₃ (8 mL) and water (8 mL), dried over Na₂SO₄ and evaporated. The residue was purified by prep-TLC to give the title product Step F: 2-Fluoro-5-(2-{4-[2-fluoro-2-(1-oxo-1,3-dihydro-2-benzofuran-5-yl)ethyl]-2-oxopiperazin-1-yl}ethyl)benzonitrile To a flask charged with 2-Fluoro-5-[2-(2-oxopiperazin-1-yl)ethyl]benzonitrile (53 mg, 0.25 mmol) and Fluoro(1-oxo-1,3-dihydro-2-benzofuran-5-yl)acetaldehyde (20 mg, 0.10 mmol) was added NaBH(OAc)₃ (153 mg, 0.72 mmol). The mixture was stirred at RT for 12 hours. Then the reaction was diluted with DCM (120 mL), washed with brine (15 mL), dried over Na₂SO₄ and concentrated. The residue was purified with prep-TLC (MeOH/DCM=1:15) to obtain the title product. ¹H-NMR (400 MHz, MeOD) δ ppm 7.88 (d, J=8.0 Hz, 1H), 7.55-7.65 (m, 4H), 7.25 (t, J=9.0 Hz, 1H), 5.90 (dd, J=7.6, 3.2 Hz, 1H), 5.78 (dd, J=7.6, 3.2 Hz, 1H), 5.39 (s, 2H), 3.59 (d, J=7.6, 7.0 Hz, 2H), 2.80-2.95 (m, 6H).

Example 40

Mixture of 2 Enantiomers

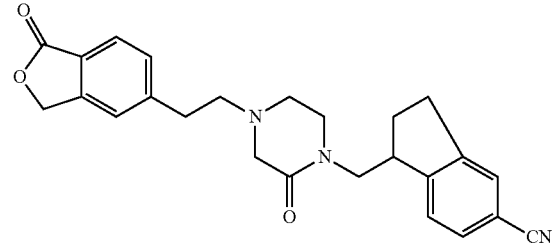 [SMILES: N#Cc1ccc2c(c1)CCC2CN1CCN(CCc2ccc3c(c2)COC3=O)CC1=O]

1-({2-Oxo-4-[2-(1-oxo-1,3-dihydro-2-benzofuran-5-yl)ethyl]piperazin-1-yl}methyl)-2,3-dihydro-1H-indene-5-carbonitrile To a mixture of 1-[(2-Oxopiperazin-1-yl)methyl]-2,3-dihydro-1H-indene-5-carbonitrile (42 mg, 0.16 mmol), NaBH₃CN (40 mg, 0.66 mmol) and HOAc (40 mg, 0.66 mmol) in 20 mL DCM was added (1-Oxo-1,3-dihydro-2-benzofuran-5-yl)acetaldehyde (29 mg, 0.16 mmol) and the mixture was stirred at RT overnight. Then saturated Na₂CO₃ (50 mL) was added and stirred for 30 min and extracted with EtOAc (3×50 mL). The combined organic layers were washed with water and brine, dried over anhydrous sodium sulfate, and concentrated. The residue was purified by prep-TLC to give the title product. ¹H-NMR (400 MHz, CDCl3) δ ppm 7.84 (d, J=8.6 Hz, 2H), 7.50 (s, 1H), 7.44 (d, J=7.8 Hz, 1H), 7.37 (d, J=7.8 Hz, 1H), 7.32 (s, 1H), 7.27 (d, J=7.8 Hz, 1H), 5.28 (s, 2H), 3.50~3.61 (m, 3H), 3.20~3.32 (m, 4H), 2.99~3.08 (m, 1H), 2.84~2.95 (m, 3H), 2.67~2.77 (m, 4H), 2.21~2.30 (m, 1H), 1.87~1.95 (m, 1H).

Example 41

Mixture of 2 Enantiomers

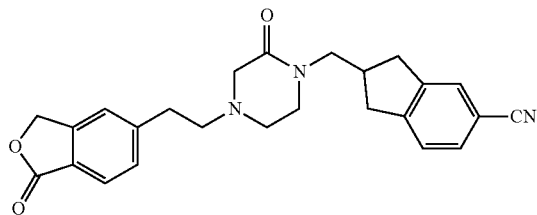 [SMILES: N#Cc1ccc2c(c1)CC(CN1CCN(CCc3ccc4c(c3)COC4=O)CC1=O)C2]

2-({2-Oxo-4-[2-(1-oxo-1,3-dihydro-2-benzofuran-5-yl)ethyl]piperazin-1-yl}methyl)-2,3-dihydro-1H-indene-5-carbonitrile To a mixture of 2-[(2-Oxopiperazin-1-yl)methyl]-2,3-dihydro-1H-indene-5-carbonitrile (170 mg, 0.70 mmol), NaBH₃CN (84 mg, 1.3 mmol) and HOAc (80 mg, 1.3 mmol) in 50 mL MeOH was added (1-Oxo-1,3-dihydro-2-benzofuran-5-yl)acetaldehyde (235 mg, 1.3 mmol) and the mixture was stirred at RT overnight. Then saturated Na₂CO₃ (50 mL) was added and stirred for 30 min and extracted with EtOAc (3×50 mL). The combined organic layers were washed with water and brine, dried over anhydrous sodium sulfate, and concentrated. The residue was purified by prep-TLC to give the title product. ¹H-NMR (400 MHz, MeOD) δ ppm 7.78 (d, J=7.8 Hz, 1H), 7.46~7.51 (m, 4H), 7.34 (d, J=7.8 Hz, 1H), 5.34 (s, 2H), 3.48 (d, J=7.0 Hz, 2H), 3.43 (t, J=5.5 Hz, 2H), 3.21 (s, 2H), 2.69~3.09 (m, 11H).

Example 42

Mixture of 2 Enantiomers

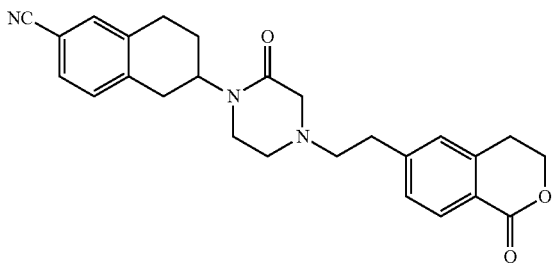 [SMILES: N#Cc1ccc2c(c1)CCC(N1CCN(CCc3ccc4c(c3)CCOC4=O)CC1=O)C2]

6-{2-Oxo-4-[2-(1-oxo-3,4-dihydro-1H-isochromen-6-yl)ethyl]piperazin-1-yl}-5,6,7,8-tetrahydronaphthalene-2-carbonitrile A mixture of 6-(2-Oxopiperazin-1-yl)-5,6,7,8-tetrahydronaphthalene-2-carbonitrile (51 mg, 0.17 mmol) and triethylamine (65 mg, 0.64 mmol) was dissolved in dichloroethane then (1-oxo-3,4-dihydro-1H-isochromen-6-yl)acetaldehyde (60 mg, 0.26 mmol) was added followed by sodium triacetoxyborohydride (270 mg, 1.28 mmol). The reaction mixture was stirred at RT for 16 hours. The reaction mixture was poured into water then extracted with dichloromethane. The organic layer was washed with brine then dried over Na₂SO₄, filtered and concentrated. The compound was purified by preparative TLC plate to yield the title product. ¹H-NMR (500 MHz, CDCl₃) δ ppm 8.07 (d, J=7.8 Hz, 1H), 7.43 (s, 1H), 7.42 (d, J=7.5 Hz, 1H), 7.28 (d, J=8.0 Hz, 1H), 7.18 (d, J=7.61 Hz, 1H), 7.14 (s, 1H), 4.90 (b, 1H), 4.57 (t, J=5.7 Hz, 2H), 3.27-3.36 (m, 4H), 3.08 (t, J=5.8 Hz, 2H), 3.02-2.74 (m, 10H), 2.01 (b, 1H), 1.92-1.95 (m, 1H).

Example 43

Mixture of 2 Enantiomers

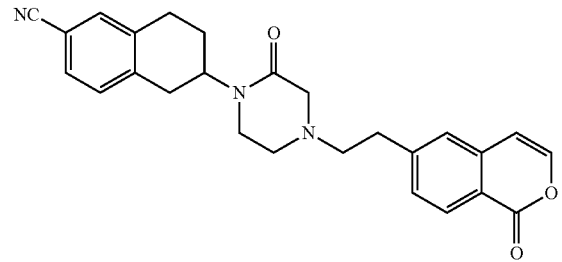 [SMILES: N#Cc1ccc2c(c1)CCC(N1CCN(CCc3ccc4c(=O)occc4c3)CC1=O)C2]

6-{2-Oxo-4-[2-(1-oxo-1H-isochromen-6-yl)ethyl]piperazin-1-yl}-5,6,7,8-tetrahydronaphthalene-2-carbonitrile A mixture of 6-(2-Oxopiperazin-1-yl)-5,6,7,8-tetrahydronaphthalene-2-carbonitrile (26 mg, 0.089 mmol) and triethylamine (12.1 mg, 0.12 mmol) was dissolved in dichloroethane (10 ml) then (1-Oxo-1H-isochromen-6-yl)acetaldehyde (15 mg, 0.080 mmol) followed by sodium triacetoxyborohydride (51 mg, 0.24 mmol) was added. The reaction mixture was stirred at RT for 16 hrs. The reaction mixture was poured into water and extracted with DCM. The organic layer was washed with brine then dried over Na₂SO₄, filtered and concentrated. The compound was purified by preparative TLC plate to yield the title product. ¹H-NMR (500 MHz, CDCl₃) δ ppm 8.27 (d, J=8.1 Hz, 1H), 7.43 (s, 1H), 7.42 (d, J=8.5 Hz, 2H), 7.32 (d, J=5.7 Hz, 1H), 7.19 (d, J=7.8 Hz, 1H), 6.50 (d, J=5.8 Hz, 1H), 4.90 (b, 1H), 3.28-3.39 (m, 4H), 2.92-3.03 (m, 6H), 2.76-2.86 (m, 4H), 2.04 (b, 1H), 1.89-1.98 (m, 1H).

Example 44

Mixture of 2 Enantiomers

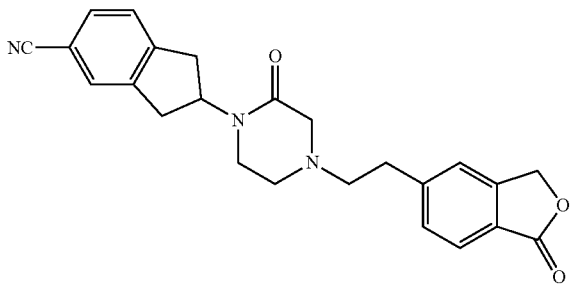 [SMILES: N#Cc1ccc2c(c1)CC(N1CCN(CCc3ccc4c(c3)COC4=O)CC1=O)C2]

2-{2-Oxo-4-[2-(1-oxo-1,3-dihydro-2-benzofuran-5-yl)ethyl]piperazin-1-yl}-2,3-dihydro-1H-indene-5-carbonitrile

Step A: tert-Butyl {2-[(5-bromo-2,3-dihydro-1H-inden-2-yl)amino]ethyl}carbamate To a solution of 5-Bromo-2,3-dihydro-1H-inden-2-amine (0.21 g, 1.0 mmol) in 16 mL of DCM/MeOH (7/1, v/v) was added tert-Butyl(2-oxoethyl)carbamate (160 mg, 1.0 mmol) and NaBH(OAc)$_3$ (297 mg, 1.4 mmol), and the mixture was stirred at RT for 3 hours. DCM was added to the mixture, and then washed with brine. The organic layer was dried over anhydrous Na$_2$SO$_4$ and concentrated. The residue was purified by prep-TLC to give the title product.

Step B: tert-Butyl {2-[(5-bromo-2,3-dihydro-1H-inden-2-yl)-(chloroacetyl)amino]ethyl}carbamate To a solution of tert-Butyl {2-[(5-bromo-2,3-dihydro-1H-inden-2-yl)amino]ethyl}carbamate (140 mg, 0.39 mmol) in 10 mL of DCM was added TEA (159 mg, 1.58 mmol) and chloroacetyl chloride (49 mg, 0.43 mmol) at 0° C. The mixture was stirred at RT for 2 hours. DCM was added to the mixture, and then washed 1N HCl and brine. The organic layer was dried over anhydrous Na$_2$SO$_4$ and concentrated. The residue was used directly in next step.

Step C: 1-(5-Bromo-2,3-dihydro-1H-inden-2-yl)piperazin-2-one

To a solution of the product from Step B (0.17 g, 0.39 mmol) in 10 mL of DCM was added 5 mL of HCl/Et$_2$O and the mixture was stirred at RT for 2 hours and then concentrated. The residue was dissolved in 20 mL of EtOH and added K$_2$CO$_3$ (163 mg, 1.18 mmol), and then the mixture was refluxed for 4 hours. The reaction mixture was filtered and concentrated and the residue was used directly for next step.

Step D: 1-(5-Bromo-2,3-dihydro-1H-inden-2-yl)-4-[2-(1-oxo-1,3-dihydro-2-benzofuran-5-yl)ethyl]piperazin-2-one To a solution of product from Step C (0.39 mmol) in 20 mL of DCM/MeOH (3/1, v/v) was added HOAc (47 mg, 0.78 mmol), (1-oxo-1,3-dihydro-2-benzofuran-5-yl)acetaldehyde (68 mg, 0.39 mmol) and NaBH$_3$CN (49 mg, 0.78 mmol), and the mixture was stirred at RT for 2 hours. The reaction was diluted with DCM, washed with brine. The organic layer was dried over anhydrous Na$_2$SO$_4$ and concentrated. The residue was purified by prep-TLC to give the title product.

Step E: 2-{2-Oxo-4-[2-(1-oxo-1,3-dihydro-2-benzofuran-5-yl)ethyl]piperazin-1-yl}-2,3-dihydro-1H-indene-5-carbonitrile To a solution of 1-(5-Bromo-2,3-dihydro-1H-inden-2-yl)-4-[2-(1-oxo-1,3-dihydro-2-benzofuran-5-yl)ethyl]piperazin-2-one (60 mg, 0.132 mmol) in 2 mL of DMF was added Zn(CN)$_2$ (15 mg, 0.132 mmol), Pd$_2$(dba)$_3$ (20 mg), TMEDA (10 mg), Xantphos (10 mg), and the mixture was stirred under microwave irradiation for 3 min at 100° C. The mixture was diluted with EtOAc and then filtrated. The filtrate was washed with brine, dried over anhydrous Na$_2$SO$_4$ and concentrated. The residue was purified by prep-TLC to give the title product. $^1$H-NMR (400 MHz, CDCl$_3$) δ ppm 7.81 (d, J=7.8 Hz, 1H), 7.44-7.48 (m, 2H), 7.28~7.34 (m, 3H), 5.49~5.57 (m, 1H), 5.26 (s, 2H), 3.19~3.28 (m, 4H), 2.88~3.1 (m, 6H), 2.65~2.7 (m, 4H).

Example 45

2 Diastereomers

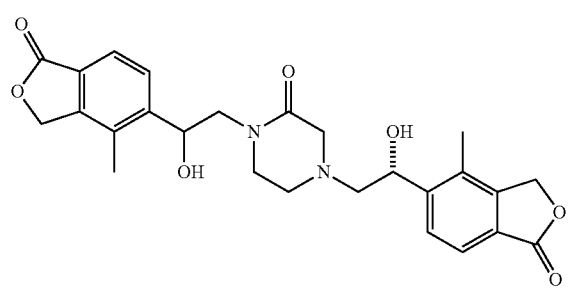 [SMILES: Cc1c(C(O)CN2CCN(C[C@H](O)c3ccc4c(c3C)COC4=O)CC2=O)ccc2c1COC2=O]

4-[(2R)-2-Hydroxy-2-(4-methyl-1-oxo-1,3-dihydro-2-benzofuran-5-yl)ethyl]-1-[2-hydroxy-2-(4-methyl-1-oxo-1,3-dihydro-2-benzofuran-5-yl)ethyl]piperazin-2-one A mixture of 1-[2-Hydroxy-2-(4-methyl-1-oxo-1,3-dihydro-2-benzofuran-5-yl)ethyl]piperazin-2-one (49 mg, 0.17 mmol) and 4-methyl-5-[(2R)-oxiran-2-yl]-2-benzofuran-1 (3H)-one (64 mg, 0.34 mmol) in EtOH (2 mL) in a 5 mL microwave tube was heated to 150° C. for 2 hours. LC showed formation of the product, which was purified by mass-directed reverse phase HPLC (AcCN-Water with 0.1% TFA). LC-MS (IE, m/z): 481 [M+1]$^+$.

Example 46

2 Diastereomers

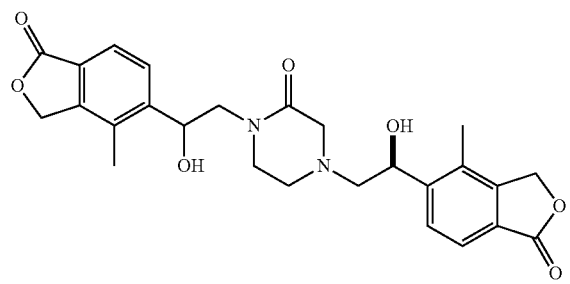 [SMILES: Cc1c(C(O)CN2CCN(C[C@@H](O)c3ccc4c(c3C)COC4=O)CC2=O)ccc2c1COC2=O]

4-[(2S)-2-Hydroxy-2-(4-methyl-1-oxo-1,3-dihydro-2-benzofuran-5-yl)ethyl]-1-[2-hydroxy-2-(4-methyl-1-oxo-1,3-dihydro-2-benzofuran-5-yl)ethyl]piperazin-2-one A mixture of 1-[2-Hydroxy-2-(4-methyl-1-oxo-1,3-dihydro-2-benzofuran-5-yl)ethyl]piperazin-2-one (49 mg, 0.17 mmol) and 4-methyl-5-[(2S)-oxiran-2-yl]-2-benzofuran-1(3H)-one (64 mg, 0.34 mmol) in EtOH (2 mL) in a 5 mL microwave tube was heated to 150° C. for 2 hours. LC showed formation of the product, which was purified by mass-directed reverse phase HPLC (AcCN-Water with 0.1% TFA). LC-MS (IE, m/z): 481 [M+1]$^+$.

Example 47

2 Diastereomers

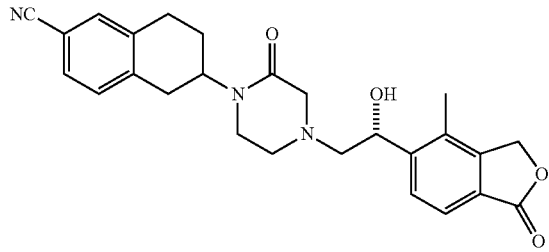 [SMILES: Cc1c([C@@H](O)CN2CCN(C3CCc4cc(C#N)ccc4C3)C(=O)C2)ccc2c1COC2=O]

6-{4-[(2R)-2-Hydroxy-2-(4-methyl-1-oxo-1,3-dihydro-2-benzofuran-5-yl)ethyl]-2-oxopiperazin-1-yl}-5,6,7,8-tetrahydronaphthalene-2-carbonitrile A mixture of 6-(2-Oxopiperazin-1-yl)-5,6,7,8-tetrahydronaphthalene-2-carbonitrile (70 mg, 0.27 mmol) and 4-methyl-5-[(2R)-oxiran-2-yl]-2-benzofuran-1(3H)-one (73 mg, 0.38 mmol) in EtOH (2 mL) in a 5 mL microwave tube was heated to 148° C. for 1.5 hours. LC showed formation of the product, which was purified by mass-directed reverse phase HPLC (AcCN-Water with 0.1% TFA). LC-MS (IE, m/z): 481 [M+1]$^+$.

Example 48

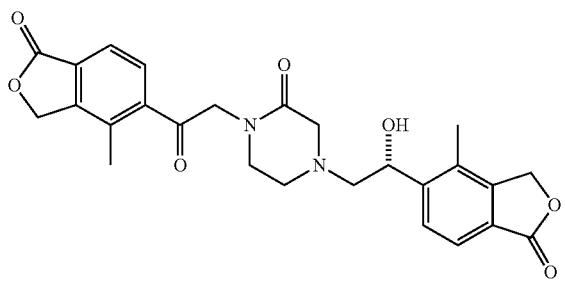 [SMILES: Cc1c(C(=O)CN2CCN(C[C@H](O)c3ccc4c(c3C)COC4=O)CC2=O)ccc2c1COC2=O]

4-[(2R)-2-Hydroxy-2-(4-methyl-1-oxo-1,3-dihydro-2-benzofuran-5-yl)ethyl]-1-[2-(4-methyl-1-oxo-1,3-dihydro-2-benzofuran-5-yl)-2-oxoethyl]piperazin-2-one A mixture of 1-[2-(4-methyl-1-oxo-1,3-dihydro-2-benzofuran-5-yl)-2-oxoethyl]piperazin-2-one (30 mg, 0.10 mmol) and 4-methyl-5-[(2R)-oxiran-2-yl]-2-benzofuran-1(3H)-one (40 mg, 0.21 mmol) in EtOH (2 mL) was heated to 140° C. in a microwave tube for 1 hour. The solution was concentrated to dryness, re-dissolved in MeOH, filtered and shot into Mass-directed HPLC for separation to give the title product. LC-MS (IE, m/z): 479 [M+1]$^+$.

Example 49

4 Diastereomers

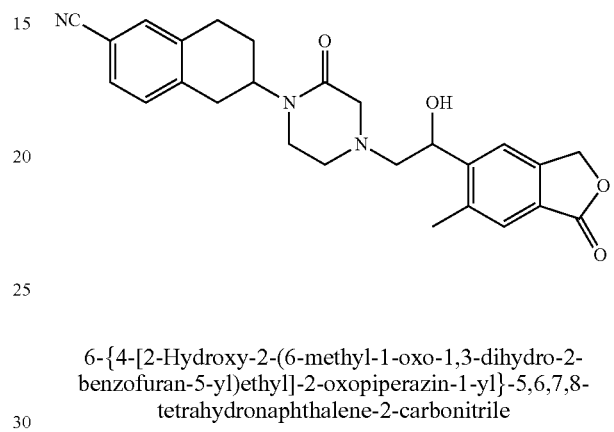

6-{4-[2-Hydroxy-2-(6-methyl-1-oxo-1,3-dihydro-2-benzofuran-5-yl)ethyl]-2-oxopiperazin-1-yl}-5,6,7,8-tetrahydronaphthalene-2-carbonitrile A mixture of 6-methyl-5-(oxiran-2-yl)-2-benzofuran-1(3H)-one (22 mg, 0.12 mmol) and 6-(2-Oxopiperazin-1-yl)-5,6,7,8-tetrahydronaphthalene-2-carbonitrile (30 mg, 0.12 mmol) in EtOH (2 mL) was heated to 140° C. for 1 hour. The reaction mixture was concentrated to dryness, and dissolved in MeOH, filtered and shot into Mass-directed HPLC for separation to give the title product. LC-MS (IE, m/z): 446 [M+1]$^+$.

Example 50

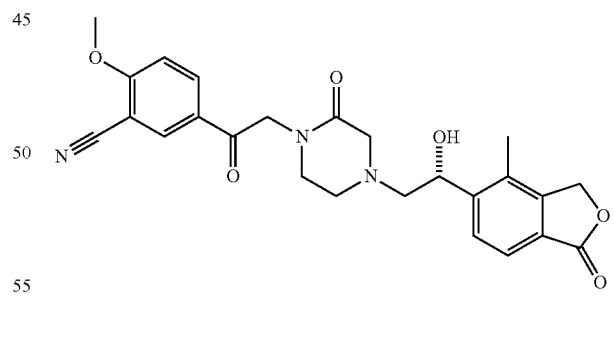

3-({4-[(2R)-2-Hydroxy-2-(4-methyl-1-oxo-1,3-dihydro-2-benzofuran-5-yl)ethyl]-2-oxopiperazin-1-yl}acetyl)-6-methoxy-2-methylbenzonitrile A mixture of 6-Methoxy-2-methyl-3-[(2-oxopiperazin-1-yl)acetyl]benzonitrile (40 mg, 0.14 mmol) and 4-methyl-5-[(2R)-oxiran-2-yl]-2-benzofuran-1(3H)-one (40 mg, 0.21 mmol) in EtOH (2 mL) was heated to 140° C. for 1 hour. The reaction mixture was concentrated to dryness, and dissolved in MeOH, filtered and shot into Mass-directed HPLC for separation to give the title product. LC-MS (IE, m/z): 478 [M+1]⁺.

Example 51

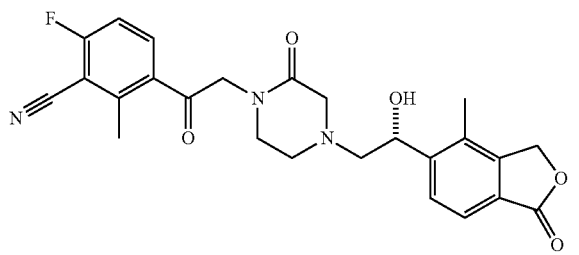 [SMILES: Cc1c(C(=O)CN2CCN(C[C@H](O)c3ccc4c(c3C)COC4=O)CC2=O)ccc(F)c1C#N]

6-Fluoro-3-({4-[(2R)-2-hydroxy-2-(4-methyl-1-oxo-1,3-dihydro-2-benzofuran-5-yl)ethyl]-2-oxopiperazin-1-yl}acetyl)-2-methylbenzonitrile A mixture of 6-Fluoro-2-methyl-3-[(2-oxopiperazin-1-yl)acetyl]benzonitrile (40 mg, 0.14 mmol) and 4-methyl-5-[(2R)-oxiran-2-yl]-2-benzofuran-1(3H)-one (42 mg, 0.22 mmol) in EtOH (2 mL) was heated to 140° C. for 1 hour. The reaction mixture was concentrated to dryness, and dissolved in MeOH, filtered and shot into Mass-directed HPLC for separation to give the title product. LC-MS (IE, m/z): 466 [M+1]⁺.

Example 52

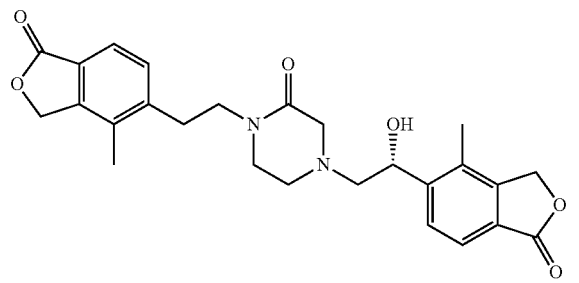 [SMILES: Cc1c(CCN2CCN(C[C@H](O)c3ccc4c(c3C)COC4=O)CC2=O)ccc2c1COC2=O]

4-[(2R)-2-hydroxy-2-(4-methyl-1-oxo-1,3-dihydro-2-benzofuran-5-yl)ethyl]-1-[2-(4-methyl-1-oxo-1,3-dihydro-2-benzofuran-5-yl)ethyl]piperazin-2-one A sealed tube containing 1-[2-(4-Methyl-1-oxo-1,3-dihydro-2-benzofuran-5-yl)ethyl]piperazin-2-one (60 mg, 0.19 mmol) and 4-methyl-5-[(2R)-oxiran-2-yl]-2-benzofuran-1(3H)-one dissolved in 1 mL of EtOH was heated to 100° C. overnight. After 16 hrs the solvent was removed and the material purified via flash chromatography to give the title product. LC-MS (IE, m/z): 465 [M+1]⁺.

Example 53

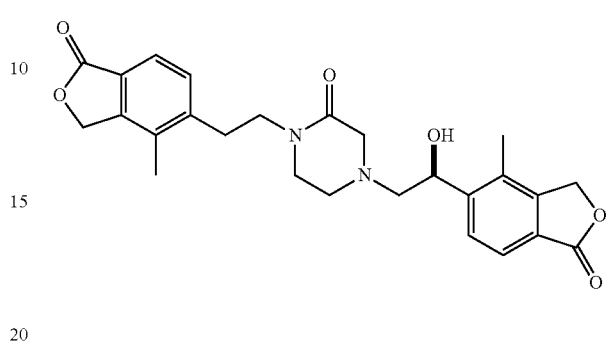

4-[(2S)-2-hydroxy-2-(4-methyl-1-oxo-1,3-dihydro-2-benzofuran-5-yl)ethyl]-1-[2-(4-methyl-1-oxo-1,3-dihydro-2-benzofuran-5-yl)ethyl]piperazin-2-one A sealed tube containing 1-[2-(4-Methyl-1-oxo-1,3-dihydro-2-benzofuran-5-yl)ethyl]piperazin-2-one (60 mg, 0.19 mmol) and 4-methyl-5-[(2S)-oxiran-2-yl]-2-benzofuran-1(3H)-one dissolved in 1 mL of EtOH was heated to 100° C. overnight. After 16 hrs the solvent was removed and the material purified via flash chromatography to give desired product. LC-MS (IE, m/z): 465 [M+1]⁺.

Example 54

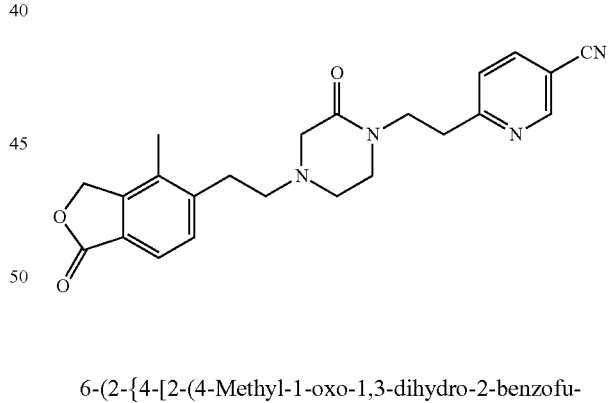

6-(2-{4-[2-(4-Methyl-1-oxo-1,3-dihydro-2-benzofuran-5-yl)ethyl]-2-oxopiperazin-1-yl}ethyl)pyridine-3-carbonitrile A mixture of 6-[2-(2-Oxopiperazin-1-yl)ethyl]pyridine-3-carbonitrile [I-14](1 eq), (4-Methyl-1-oxo-1,3-dihydro-2-benzofuran-5-yl)acetaldehyde (1 eq) and NaBH(OAc)₃ in 10 mL of DCM was stirred overnight at RT. The mixture was diluted with 50 mL of DCM and washed with brine, concentrated and the residue was purified by prep-TLC (DCM:MeOH=15:1) to afford the title product. ¹H-NMR (400 MHz, CDCl3) δ ppm 8.73 (s, 1H), 7.82 (d, J=7.6 Hz, 1H), 7.63 (d, J=8.0 Hz, 1H), 7.31 (d, J=7.6 Hz, 1H), 7.25 (d, J=8.0 Hz, 1H), 5.18 (s, 2H), 3.71 (t, J=7.2 Hz, 2H), 3.26 (s, 2H), 3.08-3.14 (m, 4H), 2.85 (t, J=7.6 Hz, 2H), 2.65 (s, 2H), 2.54 (t, J=7.6 Hz, 2H), 2.21 (s, 3H).

Example 55

Isomer B

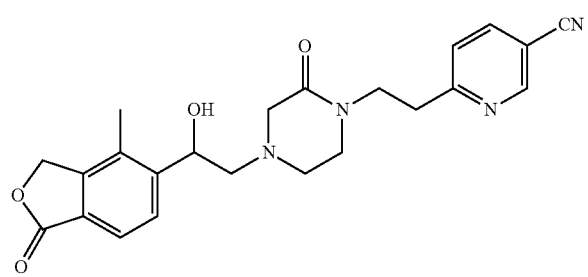 [SMILES: Cc1c(C(O)CN2CCN(CCc3ccc(C#N)cn3)C(=O)C2)ccc2c1COC2=O]

6-(2-{4-[2-Hydroxy-2-(4-methyl-1-oxo-1,3-dihydro-2-benzofuran-5-yl)ethyl]-2-oxopiperazin-1-yl}ethyl)pyridine-3-carbonitrile A mixture of 6-[2-(2-Oxopiperazin-1-yl)ethyl]pyridine-3-carbonitrile (1 eq) and 4-Methyl-5-(oxiran-2-yl)-2-benzofuran-1(3H)-one (1 eq) in 4 mL of EtOH was microwaved at 140° C. for 90 minutes. The solution was cooled, condensed, and the residue was first purified by prep-TLC (DCM:MeOH=10:1, larger Rf), then the two stereo-isomers were separated by SFC (AS 250 mm×30 mm, 5 µM, A (supercritical $CO_2$): B (EtOH with 0.05% DEA)=55:45 at 30 mL/min) to afford the separated stereo-isomers A (faster eluting) and B (slower eluting). Isomer B was more potent in the Thallium Flux Assay than Isomer A. LC-MS (IE, m/z): 421 $[M+1]^+$. Isomer A had an $IC_{50}$ greater than 1 uM in the Thallium Flux Assay.

Example 56

Mixture of 2 Enantiomers

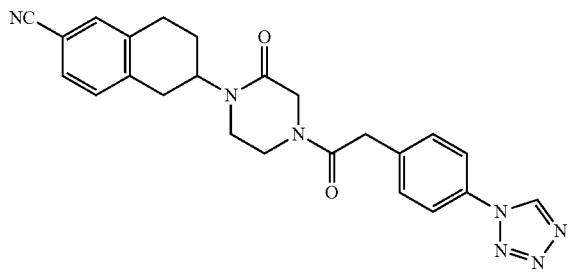 [SMILES: N#Cc1ccc2c(c1)CCC(N1CCN(C(=O)Cc3ccc(-n4cnnn4)cc3)CC1=O)C2]

6-(2-Oxo-4-{[4-(1H-tetrazol-1-yl)phenyl]acetyl}piperazin-1-yl)-5,6,7,8-tetrahydronaphthalene-2-carbonitrile To a solution of 6-(2-Oxopiperazin-1-yl)-5,6,7,8-tetrahydronaphthalene-2-carbonitrile (40 mg, 0.16 mmol) and [4-(1H-tetrazol-1-yl)phenyl]acetic acid (38 mg, 0.19 mmol) in DCM (3 ml) was added DMAP (25 mg, 0.20 mmol) and EDC (39 mg, 0.20 mmol). The mixture was allowed to stir at RT for 4 hours. LC showed formation of the desired product. The solvent was removed under vacuum, and the residue was redissolved in methanol, and purified by reverse phase HPLC to give the title product. LC-MS (IE, m/z): 442 $[M+1]^+$.

Example 57

Mixture of 2 Enantiomers

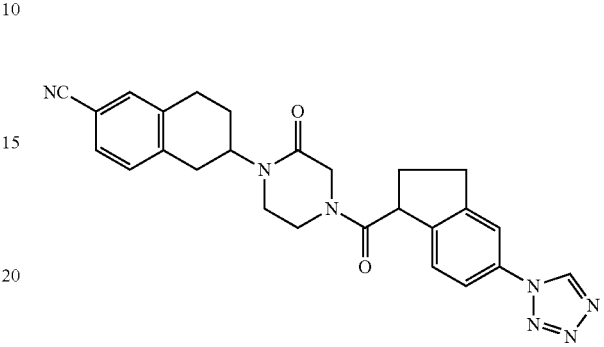

6-(2-Oxo-4-{[5-(1H-tetrazol-1-yl)-2,3-dihydro-1H-inden-1-yl]carbonyl}piperazin-1-yl)-5,6,7,8-tetrahydronaphthalene-2-carbonitrile A mixture of 6-(2-Oxopiperazin-1-yl)-5,6,7,8-tetrahydronaphthalene-2-carbonitrile (40 mg, 0.16 mmol) (20 mg, 0.078 mmol), 5-(1H-tetrazol-1-yl)-2,3-dihydro-1H-indene-1-carboxylic acid (18 mg, 0.078 mmol), DMAP (14 mg, 0.12 mmol), and EDC (23 mg, 0.12 mmol) was stirred in dichloroethane (2 mL) for 2 hours. The solvent was removed under vacuum, and the residue was redissolved in methanol, and purified by reverse phase HPLC to give the title product. LC-MS (IE, m/z): 468 $[M+1]^+$.

Several assays may be used to measure functional inhibition of the ROMK channel by compounds of the instant invention. One assay that was used to test the activity of compounds in the Examples is the functional $^{86}Rb^+$ efflux assay described below, that measures the ability of ROMK to permeate $^{86}Rb^+$, in the absence or presence of test compound. Under control conditions, cells loaded with $^{86}Rb^+$ and incubated in $Rb^+$-free medium display a time-dependent efflux of the isotope, the rate of which depends on number of functional channels. When cells are incubated in the presence of a channel inhibitor, efflux of $^{86}Rb^+$ is prevented in a concentration-dependent manner, and $IC_{50}$ values of inhibition by compounds can be accurately determined. This assay has been established with cell lines expressing either human, rat or dog ROMK channels, and can operate in 96- or 384-well format. Importantly, the human, rat, and dog $^{86}Rb^+$ efflux assays can be carried out in the presence of up to 100% serum allowing, therefore, an accurate estimation of the effect of protein binding on the inhibitory activity of compounds of interest. Another ROMK functional assay used to test the activity of compounds in the Examples (described below) makes use of the ability of thallium to permeate through open ROMK channels and increase the fluorescence of a dye previously loaded into the cells. Under control conditions, cells loaded with dye and exposed to thallium-containing medium display a time-dependent increase in fluorescence, the rate of which depends on number of functional channels. When cells are incubated in the presence of a channel inhibitor, the increase in fluorescence is attenuated in a concentration-dependent manner, and $IC_{50}$ values of inhibition by compounds can be accurately determined. This assay has been established with cell lines expressing either human, or rat ROMK channels, and operates in 384-well format.

$^{86}Rb^+$ Efflux Assay

Cell Culture Conditions—
CHO-DHFR-cells stably expressing hROMK1 ($K_{ir}1.1$) are grown at 37° C. in a 10% $CO_2$ humidified incubator in Iscove's Modified Dulbecco's Medium (Gibco 12440) supplemented with HT Supplement, Penicillin/Streptomycin/Glutamine, G418 (500 µg/ml) and 10% FBS. Cells are seeded in Sterile and Tissue Culture Treated Packard Cultur-Plate White Opaque Microplates at a concentration of 5.0E5-7.0E5 cells/ml-PerkinElmer 6005680 (96-well); Corning 3707 (384 well) in complete media containing 1.5 µCi/ml Rubidium-86. Cells are incubated in 37° C.-10% $CO_2$ incubator overnight. On the day of the experiment, the media is removed and cells are washed with low K assay buffer. $^{86}Rb^+$ efflux is initiated after addition of assay buffer±test compound followed by 35 min incubation at room temperature. ROMK-sensitive component of efflux is defined in the presence of 10 mM $BaCl_2$. Assay buffer is removed and transferred to a plate and cells are solubilized in the presence of SDS. Radioactivity associated with assay and cell plate is determined.

Step Protocol
1. Remove cell media and wash cells with low K assay buffer (126.9 mM NaCl, 4.6 mM KCl, 2 mM $CaCl_2$, 1 mM $MgCl_2$, 10 mM Hepes/NaOH; pH 7.4)
   200 µl for 96-well plate; 70 µl for 384-well plate
2. Add assay buffer (121.5 mM NaCl, 10 mM KCl, 2 mM $CaCl_2$, 1 mM $MgCl_2$, 10 mM Hepes/NaOH; pH 7.4) ±test compound to cells
   100 µl for 96-well plate; 50 µl for 384-well plate
3. Incubate at ambient temperature (22-24° C.) for 35 min
4. Remove assay buffer add it to a 96- or 384-well plate containing Microscint-20
   96-well Plate: 100 µl buffer, 170 µl MicroScint 20 (for TopCount)
   384-well plate: 20 µl buffer, 50 µl Optiphiase (for MicroLux)
5. Completely remove remaining assay buffer from cell plate
6. Solubilize cells with 1% SDS; than add MicroScint or Optiphase
   96-well Plate: 30 µl SDS, 170 µl MicroScint 20 (for TopCount)
   384-well plate: 20 µl SDS, 50 µl Optiphiase (for MicroLux)
7. Seal both cell and supernatant plates and count Data Calculation—
Radioactivity associated with the assay plate is normalized to the total radioactivity (assay+cell plates) to provide % efflux, under each condition. % efflux in the presence of 10 mM $BaCl_2$ is subtracted from each experimental point to provide the ROMK-sensitive component of $^{86}Rb^+$ efflux. In the absence of test compound, this number corresponds to 100% control efflux. $IC_{50}$ values represent the concentration of compound that inhibits 50% of ROMK efflux. Normally, a control compound is included to support that the assay is giving consistent results compared to previous measurements, although the control is not required to obtain the results for the test compounds. The control can be any compound of Formula I of the present invention, preferably with an $IC_{50}$ potency of less than 1 µM in this assay. Alternatively, the control could be another compound (outside the scope of Formula I) that has an $IC_{50}$ potency in this assay of less than 1 µM.

Thallium Flux Assay

Cell Culture Conditions—
HEK293 cells stably expressing hROMK (h$K_{ir}1.1$) were grown at 37° C. in a 10% $CO_2$ humidified incubator in complete growth media: Dulbecco's Modified Eagle Medium supplemented with non-essential amino acids, Penicillin/Streptomycin/Glutamine, G418 and FBS. At >80% confluency, aspirate the media from the flask and rinse with 10 mL Calcium/Magnesium-free PBS. Add 5 mL of 1× trypsin (prepared in Ca/Mg Free PBS) to T-225 flask and return flask to 37° C./$CO_2$ incubator for 2-3 minutes. To dislodge the cell, gently bang the side of the flask with your hand. Triturate the cells completely and then transfer the cells to 25 mL complete media. Centrifuge at 1,500 rpm for 6 min followed by resuspension in complete growth media and determine cell concentration. For typical re-seeding, 4E6 cells/T-225 flask will attain >80% confluency in 4 days. Under ideal growth conditions and appropriate tissue culture practices, this cell line is stable for 40-45 passages.

FluxOR Kit Components (Invitrogen F10017)
   FluxOR™ Reagent (Component A)
   FluxOR™ Assay Buffer (Component B)—10× Concentrate
   PowerLoad™ Concentrate (Component C)—100× Concentrate
   Probenecid (Component D)—Lyophilized sample is kept at −20° C. Water soluble, 100× after solubilization in 1 mL water. Store at 4° C.
   FluxOR™ Chloride-free Buffer (Component E)—5× Concentrate
   Potassium sulfate ($K_2SO_4$) Concentrate (Component F)—125 mM in water. Store at 4° C.
   Thallium sulfate ($Tl_2SO_4$) Concentrate (Component G)—50 mM in water. Store at 4° C.
   DMSO (dimethyl sulfoxide, Component H)—1 mL (100%)

Reagent Preparation: FluxOR Working Solutions
   1000× FluxOR™ Reagent: Reconstitute a vial of component A in 100 µl DMSO; Mix well; Store 10 µl aliquots at −20° C.
   1× FluxOR™ Assay Buffer: Dilute Component B 10-fold with water; Adjust pH to 7.4 with Hepes/NaOH; Filter and store at 4° C.
   Probenecid/Assay Buffer: 100 mL of 1× FluxOR™ Assay Buffer; 1 mL of reconstituted component D; Store at 4° C.
   Loading Buffer (per microplate): 10 µl 1000× FluxOR™ Reagent; 100 µl component C; 10 mL Probenecid/Assay Buffer
   Compound Buffer (per microplate): 20 mL Probenecid/Assay Buffer; 0.3 mM ouabain (10 mM ouabain in water can be stored in amber bottle/aluminum foil at room temperature); Test compound
   1× FluxOR™ Chloride-Free Buffer: Prepare 1× working solution in water. Can be stored at room temperature
   Stimulant Buffer (prepared at 5× final concentration in 1× FluxOR™ Chloride-Free Buffer): 7.5 mM Thallium sulfate and 0.75 mM Potassium sulfate (to give a final assay concentration of 3 mM Thallium/0.3 mM Potassium). Store at 4° C. when not in use. If kept sterile, this solution is good for months.

Assay Protocol—

The ROMK channel functional thallium flux assay is performed in 384 wells, using the FLIPR-Tetra instrument. HEK-hKir1.1 cells are seeded in Poly-D-Lysine microplates and kept in a 37° C.-10% $CO_2$ incubator overnight. On the day of the experiment, the growth media is replaced with the FluxOR™ reagent loading buffer and incubated, protected from light, at ambient temperature (23-25° C.) for 90 min. The loading buffer is replaced with assay buffer±test compound followed by 30 min incubation at ambient temperature, where the Thallium/Potassium stimulant is added to the microplate.

Step Protocol
1. Seed HEK-hKir1.1 cells (50 µl at 20,000 cells/well) in 384-well PDL coated Microplates
2. Allow cells to adhere overnight in humidified 37° C./10% $CO_2$ incubator
3. Completely remove cell growth media from microplate and replace with 25 µl loading buffer
4. Incubate Microplate at room temperature, protected form light, for 90 min
5. Remove loading buffer and replace with 25 µl 1× Assay Buffer±test compound.
6. Incubate microplate at room temperature, protected form light, for 30 min
7. At FLIPR-Tetra 384: Add stimulant (Thallium/Potassium) solution to microplate and monitor fluorescence. Excitation=400 nm, Emission=460 & 580 nm. Collect data for ~10 min.

Data Calculation—

The fluorescence intensity of wells containing 3 µM of a standard control ROMK inhibitor of the present invention is used to define the ROMK-sensitive component of thallium flux. Fluorescence in the presence of test compounds is normalized to control values to provide % fluorescence change. $IC_{50}$ values represent the concentration of compound that inhibits 50% of the ROMK thallium flux signal.

Assay Standard—

Normally, a control compound is included to support that the assay is giving consistent results compared to previous measurements, although the control is not required to obtain the results for the test compounds. The control can be any compound of Formula I of the present invention, preferably with an $IC_{50}$ potency of less than 1 µM in this assay. Alternatively, the control could be another compound (outside the scope of Formula I) that has an $IC_{50}$ potency in this assay of less than 1 µM.

All of the final product compounds in the Examples were tested in the $^{86}Rb^+$ Efflux Assay or the Thallium Flux Assay, and each compound had $IC_{50}$ results of 1 µM or less in the $^{86}Rb^+$ Efflux Assay or the Thallium Flux Assay unless otherwise noted in the Examples section. Representative examples of data collected using the $^{86}Rb^+$ Efflux Assay or the Thallium Flux Assay for the noted compound Examples are shown in Table 1.

TABLE 1

| EXAMPLE | $^{86}Rb^+$ Efflux $IC_{50}$ (µM) | Thallium Flux $IC_{50}$ (µM) |
|---|---|---|
| 1 | 0.07 | |
| 2 | 0.04 | |
| 3 | 0.74 | |
| 4 | 0.31 | |
| 5 | 0.12 | |
| 6 | 0.27 | |
| 7 | 0.39 | |
| 8 | 0.25 | |
| 9 | 0.08 | |
| 10 | 0.37 | |
| 11 | 0.14 | |
| 12 | 0.14 | |
| 13 | 0.31 | |
| 14 | 0.82 | |
| 15 | 0.051 | |
| 16 | 0.10 | |
| 17 | 0.07 | |
| 18 | 0.04 | |
| 19 | 0.05 | |
| 20 | 0.17 | |
| 21 | 0.12 | |
| 22 | 0.17 | |
| 23 | 0.06 | |
| 24 | 0.55 | |
| 25 | 0.24 | |
| 26 | 0.03 | |
| 27 | 0.87 | |
| 28 | 0.41 | |
| 29 | 0.42 | |
| 30 | 0.31 | |
| 31 | 0.41 | |
| 32 | 0.46 | |
| 33 | 0.15 | |
| 34 | 0.36 | |
| 35 | 0.17 | |
| 36 | 0.11 | |
| 37 | 0.28 | |
| 38 | 0.14 | |
| 39 | 0.91 | |
| 40 | 0.12 | |
| 41 | 0.38 | |
| 42 | 0.30 | |
| 43 | 0.21 | |
| 44 | 0.13 | |
| 45 | | 0.68 |
| 46 | | 0.27 |
| 47 | | 0.06 |
| 48 | | 0.08 |
| 49 | | 0.09 |
| 50 | | 0.197 |
| 51 | | 0.125 |
| 52 | | 0.235 |
| 53 | | 0.66 |
| 54 | | 0.78 |
| 55 | | 0.31 |
| 56 | 0.72 | |
| 57 | 0.80 | |

While the invention has been described with reference to certain particular embodiments thereof, numerous alternative embodiments will be apparent to those skilled in the art from the teachings described herein. Recitation or depiction of a specific compound in the claims (i.e., a species) without a specific stereoconfiguration designation, or with such a designation for less than all chiral centers, is intended to encompass the racemate, racemic mixtures, each individual enantiomer, a diastereoisomeric mixture and each individual diastereomer of the compound where such forms are possible due to the presence of one or more asymmetric centers. All patents, patent applications and publications cited herein are incorporated by reference in their entirety.

What is claimed is:

1. A compound having structural Formula I:

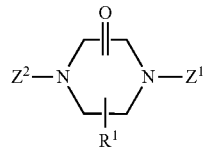

I or a pharmaceutically acceptable salts thereof wherein:

$Z^1$ is

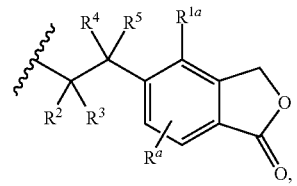

z1-a

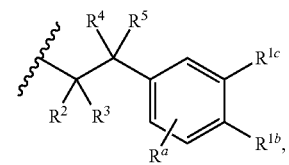

z1-b

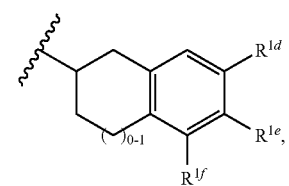

z1-c

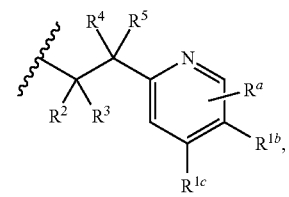

z1-d

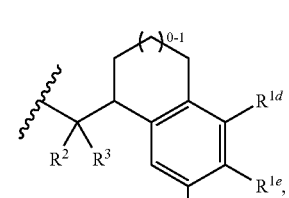

z1-e z1-f

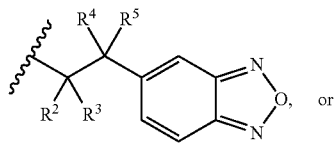

z1-g

, or

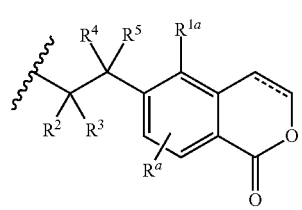

z1-h wherein the dashed line represents an optional double bond;

$Z^2$ is z2-a z2-b or z2-c

;

$R^1$ is —H, —CH$_3$, —CF$_3$, —CHF$_2$, —CH$_2$F or —CH$_2$OH;

$R^2$ is —H, oxo or —C$_{1-6}$alkyl;

$R^4$ is —H, —OH, oxo, —F or —C$_{1-6}$alkyl;
  provided that when $R^4$ is —OH, oxo or —F, then $R^2$ is not oxo;

$R^6$ is —H, —OH, oxo, —F or —C$_{1-6}$alkyl;

$R^8$ is —H, oxo or —C$_{1-6}$alkyl;
  provided that when $R^6$ is —OH, oxo or —F, then $R^8$ is not oxo;

$R^3$, $R^5$, $R^7$, and $R^9$ are each independently —H or —C$_{1-6}$alkyl;
  provided that $R^3$ is absent when $R^2$ is oxo, $R^5$ is absent when $R^4$ is oxo, $R^7$ is absent when $R^6$ is oxo, and $R^9$ is absent when $R^8$ is oxo;

$R^{1a}$ is —H, halo or —C$_{1-3}$alkyl optionally substituted with one to three of —F;

one of $R^{1b}$ and $R^{1c}$ is —CN, —NO$_2$ or tetrazolyl, and the other is —H, halo, —O—C$_{1-3}$alkyl, —COOC$_{1-3}$alkyl or —C$_{1-3}$alkyl optionally substituted with one to three of —F;

one of $R^{1d}$, $R^{1e}$ and $R^{1f}$ is —CN, —NO$_2$ or tetrazolyl, and each of the others is independently —H, halo, —O—C$_{1-3}$alkyl, —COOC$_{1-3}$alkyl or —C$_{1-3}$alkyl optionally substituted with one to three of —F;

$R^{2a}$ is —H, halo or —C$_{1-3}$alkyl optionally substituted with one to three of —F;

one of $R^{2b}$ and $R^{2c}$ is —CN, —NO$_2$ or tetrazolyl, and the other is —H, halo, —O—C$_{1-3}$alkyl, —COOC$_{1-3}$alkyl or —C$_{1-3}$alkyl optionally substituted with one to three of —F;

one of $R^{2d}$, $R^{2e}$ and $R^{2f}$ is —CN, —NO$_2$ or tetrazolyl, and each of the others is independently —H, halo, —O—C$_{1-3}$alkyl, —COOC$_{1-3}$alkyl or —C$_{1-3}$alkyl optionally substituted with one to three of —F; and $R^a$ and $R^b$ are each independently —H, halo, —O—C$_{1-3}$alkyl, —COOC$_{1-3}$alkyl or —C$_{1-3}$alkyl optionally substituted with one to three of —F.

2. The compound of claim 1 or a pharmaceutically acceptable salt thereof having structural Formula II:

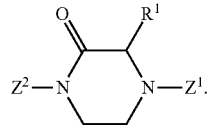

II

3. The compound of claim 1 or a pharmaceutically acceptable salt thereof wherein $Z^1$ is z1-a, z1-b, z1-d, z1-g or z1-h.

4. The compound of claim 1 or a pharmaceutically acceptable salt thereof wherein $Z^1$ is z1-c, z1-e or z1-f.

5. The compound of claim 1 or a pharmaceutically acceptable salt thereof wherein $Z^1$ is z1-a, z1-b, z1-d, z1-g or z1-h and $Z^2$ is z2-a or z2-b, and (1) $R^2$, $R^3$, $R^4$, $R^5$, $R^6$, $R^7$, $R^8$ and $R^9$ are each —H; or (2) one or both of $R^4$ and $R^6$ are independently —OH, oxo or —F, and $R^1$, $R^2$, $R^3$, $R^5$, $R^7$ and $R^8$ are each —H.

6. The compound of claim 1 or a pharmaceutically acceptable salt thereof wherein $Z^1$ is z1-e or z1-f and $R^2$ is —H or oxo and $R^3$ is —H.

7. The compound of claim 1 or a pharmaceutically acceptable salt thereof wherein $Z^1$ is z1-a, z1-b, z1-d, z1-g or z1-h and $Z^2$ is z2-c, and (1) $R^2$, $R^3$, $R^4$ and $R^5$ are each —H; or (2) $R^4$ is —OH, oxo or —F, and $R^2$, $R^3$ and $R^5$ are each —H.

8. The compound of claim 1 or a pharmaceutically acceptable salt thereof which is:

1,4-bis[2-(4-nitrophenyl)ethyl]piperazin-2-one;

6-(4-(4-nitrophenethyl)-3-oxopiperazin-1-yl)-5,6,7,8-tetrahydronaphthalene-2-carbonitrile;

6-{4-[2-(4-Nitrophenyl)ethyl]-2-oxopiperazin-1-yl}-5,6,7,8-tetrahydronaphthalene-2-carbonitrile;

6-{2-Oxo-4-[2-(1-oxo-1,3-dihydro-2-benzofuran-5-yl)ethyl]piperazin-1-yl}-5,6,7,8-tetrahydronaphthalene-2-carbonitrile;

2-{2-Oxo-4-[2-(1-oxo-1,3-dihydro-2-benzofuran-5-yl)ethyl]piperazin-1-yl}-2,3-dihydro-1H-indene-5-carbonitrile; or 6-{4-[(2R)-2-Hydroxy-2-(4-methyl-1-oxo-1,3-dihydro-2-benzofuran-5-yl)ethyl]-2-oxopiperazin-1-yl}-5,6,7,8-tetrahydronaphthalene-2-carbonitrile.

9. A pharmaceutical composition comprised of a compound of claim 1 and a pharmaceutically acceptable carrier.

10. The pharmaceutical composition of claim 9 further comprising one or more additional active agent selected from losartan, valsartan, candesartan, olmesartan, telmesartan, eprosartan, irbesartan, azilsartan, hydrochlorothiazide, amlodipine, alacepril, benazepril, captopril, ceronapril, cilazapril, delapril, enalapril, enalaprilat, fosinopril, imidapril, lisinopril, moveltipril, perindopril, quinapril, ramipril, spirapril, temocapril, trandolapril, amiloride, spironolactone, eplerenone, triamterene or acetazolamide or a pharmaceutically acceptable salt thereof.

11. A method for causing diueresis, natriuresis or both, comprising administering a compound of claim 1 in a therapeutically effective amount to a patient in need thereof.

12. A method for the treatment of one or more disorders selected from hypertension, acute heart failure, chronic heart failure, and pulmonary arterial hypertension comprising administering a compound of claim 1 in a therapeutically effective amount as appropriate, to a patient in need thereof.

* * * * *